(12) United States Patent
Wang et al.

(10) Patent No.: US 9,771,330 B2
(45) Date of Patent: Sep. 26, 2017

(54) PYRIMIDINE COMPOUNDS FOR THE TREATMENT OF CANCER

(71) Applicant: The University of North Carolina at Chapel Hill, Chapel Hill, NC (US)

(72) Inventors: Xiaodong Wang, Chapel Hill, NC (US); Weihe Zhang, Vestavia, AL (US); Stephen V. Frye, Chapel Hill, NC (US); Dmitri Kireev, Chapel Hill, NC (US); Andrew Louis McIver, Durham, NC (US); Jing Liu, Carrboro, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/647,733

(22) PCT Filed: Nov. 22, 2013

(86) PCT No.: PCT/US2013/071409
§ 371 (c)(1),
(2) Date: May 27, 2015

(87) PCT Pub. No.: WO2014/085225
PCT Pub. Date: Jun. 5, 2014

(65) Prior Publication Data
US 2015/0322019 A1 Nov. 12, 2015

Related U.S. Application Data

(60) Provisional application No. 61/730,179, filed on Nov. 27, 2012.

(51) Int. Cl.
C07D 513/08 (2006.01)
C07D 239/48 (2006.01)
C07D 487/08 (2006.01)
C07D 487/06 (2006.01)

(52) U.S. Cl.
CPC ......... *C07D 239/48* (2013.01); *C07D 487/06* (2013.01); *C07D 487/08* (2013.01)

(58) Field of Classification Search
None
See application file for complete search history.

(56) References Cited

U.S. PATENT DOCUMENTS

| | | | |
|---|---|---|---|
| 5,958,930 A | 9/1999 | Gangjee et al. | |
| 7,217,710 B2 | 5/2007 | Adams et al. | |
| 7,589,086 B2 | 9/2009 | Bondavalli et al. | |
| 7,897,607 B2 | 3/2011 | Gyorkos et al. | |
| 7,956,060 B2 | 6/2011 | Arai et al. | |
| 7,998,978 B2 | 8/2011 | Huang et al. | |
| 8,324,225 B2 | 12/2012 | Brain et al. | |
| 8,362,023 B2 | 1/2013 | Liu et al. | |
| 8,415,361 B2 | 4/2013 | Lemke et al. | |
| 8,513,242 B2 | 8/2013 | Chiang et al. | |

| | | |
|---|---|---|
| 2004/0209895 A1 | 10/2004 | Luecking et al. |
| 2006/0025383 A1 | 2/2006 | Wishart et al. |
| 2007/0078140 A1 | 4/2007 | Borzilleri et al. |
| 2007/0105874 A1 | 5/2007 | Zhang et al. |
| 2007/0225306 A1 | 9/2007 | Choi et al. |
| 2007/0275984 A1 | 11/2007 | Imogai et al. |
| 2008/0248046 A1 | 10/2008 | Ni et al. |
| 2008/0267887 A1 | 10/2008 | Yuan et al. |
| 2009/0012060 A1 | 1/2009 | Arai et al. |
| 2010/0137313 A1 | 6/2010 | Boriack-Sjodin et al. |
| 2010/0247554 A1 | 9/2010 | Lemke et al. |
| 2010/0266604 A1 | 10/2010 | Rothlin et al. |
| 2011/0281867 A1 | 11/2011 | Kalman et al. |
| 2011/0319267 A1 | 12/2011 | Ekwuribe |
| 2012/0035194 A1 | 2/2012 | Huang et al. |

(Continued)

FOREIGN PATENT DOCUMENTS

| | | | | |
|---|---|---|---|---|
| CA | 2492319 | * | 4/2004 | ........... C07D 513/08 |
| EP | 1710246 A1 | | 10/2006 | |

(Continued)

OTHER PUBLICATIONS

Verma. Molecular Cancer Therapeutics, 2011, 10(10), 1763-73.*
U.S. Appl. No. 13/641,729, filed Nov. 9, 2012, The University of North Carolina at Chapel Hill.
U.S. Appl. No. 14/348,805, filed Mar. 31, 2014, The University of North Carolina at Chapel Hill.
U.S. Appl. No. 14/384,789, filed Sep. 12, 2014, The University of North Carolina at Chapel Hill.
U.S. Appl. No. 14/436,356, filed Apr. 16, 2015, The University of North Carolina at Chapel Hill.
U.S. Appl. No. 14/678,905, filed May 27, 2015, The University of North Carolina at Chapel Hill.

(Continued)

*Primary Examiner* — Noble Jarrell
(74) *Attorney, Agent, or Firm* — Alston & Bird LLP

(57) ABSTRACT

Compounds of Formula I or II:

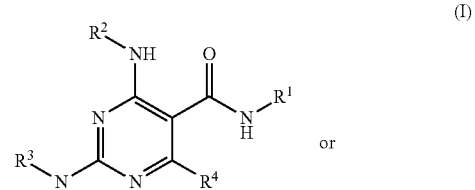

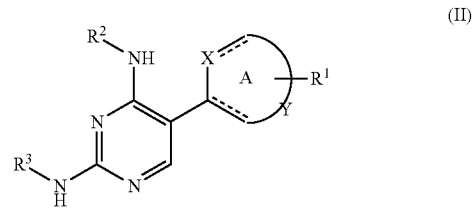

are described, along with pharmaceutical compositions containing the same and methods of using such compounds for the treatment of cancer.

3 Claims, No Drawings

(56) References Cited

U.S. PATENT DOCUMENTS

| | | |
|---|---|---|
| 2012/0207763 A1 | 8/2012 | Brain et al. |
| 2012/0207764 A1 | 8/2012 | Terrett et al. |
| 2012/0219559 A1 | 8/2012 | Chen et al. |
| 2012/0230991 A1 | 9/2012 | Graham et al. |
| 2013/0029993 A1 | 1/2013 | Stadtmueller |
| 2013/0034862 A1 | 2/2013 | Fantl et al. |
| 2013/0059836 A1 | 3/2013 | Wang et al. |
| 2013/0072382 A1 | 3/2013 | Trullinger et al. |
| 2013/0102587 A1 | 4/2013 | Evans et al. |
| 2013/0137708 A1 | 5/2013 | Garske et al. |
| 2013/0150368 A1 | 6/2013 | Ashcraft et al. |
| 2013/0266563 A1 | 10/2013 | Gokaraju et al. |

FOREIGN PATENT DOCUMENTS

| | | |
|---|---|---|
| EP | 1803723 A1 | 7/2007 |
| EP | 2133095 A1 | 12/2009 |
| EP | 2489663 A1 | 8/2012 |
| EP | 2840080 A1 | 2/2015 |
| WO | WO 97/49706 A1 | 12/1997 |
| WO | WO 03/029209 A2 | 4/2003 |
| WO | WO 2005/009443 A1 | 2/2005 |
| WO | WO 2005/028434 A2 | 3/2005 |
| WO | WO 2005/095382 A1 | 10/2005 |
| WO | WO 2006/035067 A2 | 4/2006 |
| WO | WO 2006/071819 A1 | 7/2006 |
| WO | WO 2007/032445 A1 | 3/2007 |
| WO | WO 2007/035963 A2 | 3/2007 |
| WO | WO 2007/041379 A1 | 4/2007 |
| WO | WO 2007/044426 A2 | 4/2007 |
| WO | WO 2007/075554 A2 | 7/2007 |
| WO | WO 2007/113254 A1 | 10/2007 |
| WO | WO 2007/134828 A1 | 11/2007 |
| WO | WO 2009/032694 A1 | 3/2009 |
| WO | WO 2009/047359 A1 | 4/2009 |
| WO | WO 2010/043865 A1 | 4/2010 |
| WO | WO 2010/085597 A1 | 7/2010 |
| WO | WO 2010/117425 A1 | 10/2010 |
| WO | WO 2010/129802 A1 | 11/2010 |
| WO | WO 2011/029915 A1 | 3/2011 |
| WO | PCT/US2011/036215 | 5/2011 |
| WO | WO 2011/065800 A2 | 6/2011 |
| WO | WO 2011/090760 A1 | 7/2011 |
| WO | WO 2011/103441 A1 | 8/2011 |
| WO | WO 2011/146313 A1 | 11/2011 |
| WO | WO 2012/053606 A1 | 4/2012 |
| WO | WO 2012/158795 A1 | 11/2012 |
| WO | WO 2013/032591 A1 | 3/2013 |
| WO | WO 2013/042006 A1 | 3/2013 |
| WO | WO 2013/052417 A1 | 4/2013 |
| WO | PCT/US2013/042033 | 5/2013 |
| WO | WO 2013/124324 A1 | 8/2013 |
| WO | PCT/US2013/065192 | 10/2013 |
| WO | WO 2013/157022 A1 | 10/2013 |
| WO | PCT/US2013/071409 | 11/2013 |
| WO | WO 2013/177168 A1 | 11/2013 |
| WO | WO 2014/062774 A1 | 4/2014 |
| WO | WO 2014/085225 A1 | 6/2014 |
| WO | PCT/US2015/024258 | 4/2015 |
| WO | PCT/US2015/024301 | 4/2015 |
| WO | PCT/US2015/024328 | 4/2015 |
| WO | PCT/US2015/024380 | 4/2015 |
| WO | PCT/US2015/024381 | 4/2015 |
| WO | PCT/US2015/024393 | 4/2015 |
| WO | PCT/US2015/024395 | 4/2015 |
| WO | PCT/US2015/024396 | 4/2015 |

OTHER PUBLICATIONS

U.S. Appl. No. 14/678,830, filed Apr. 3, 2015, The University of North Carolina at Chapel Hill.

U.S. Appl. No. 14/678,678, filed Apr. 3, 2015, The University of North Carolina at Chapel Hill.

U.S. Appl. No. 14/678,879, filed Apr. 3, 2015, The University of North Carolina at Chapel Hill.

U.S. Appl. No. 14/678,898, filed Apr. 3, 2015, The University of North Carolina at Chapel Hill.

U.S. Appl. No. 14/678,540, filed Apr. 3, 2015, The University of North Carolina at Chapel Hill.

Aly et al. "Heteroannelations with o-amino aldehyde and o-amino cyano of some pyrazole derivatives" *Afinidad*, Barcelona, ES (2004) 61:510-515.

Angelillo-Scherrer et al. "Role of Gas6 receptors in platelet signaling during thrombus stabilization and implications for antithrombotic therapy", *J. Clin. Invest.* (2005) 115(2):237-246.

Bernsmeier, et al. "Patients with Acute-on-Chronic Liver Failure Have Increased Numbers of Regulatory Immune Cells Expressing the Receptor Tyrosine Kinase MERTK", *Gastroenterology* (2015), 1-13.

Bhattacharayya, et al. "Enveloped viruses disable innate immune responses in dendritic cells by direct activation of TAM receptors", *Cell Host & Microbe* (2013) 14:136-147.

Brindley, et al. "Tyrosine kinase receptor Axl enhances entry of Zaire ebolavirus without direct interactions with the viral glycoprotein", *Virology* (2011) 415:83-84.

Cavasotto et al. "In silico identification of novel EGFR inhibitors with antiproliferative activity against cancer cells" *Bioorg. Med. Chem. Lett.* (2006) 16:1969-1974.

Chen, et al. "Identification of Gas6 as a ligand for Mer, a neural cell adhesion molecule related receptor tyrosine kinase implicated in cellular transformation", *Oncogene* (1997) 14:2033-2039.

Chen, et al, "Mer Receptor tyrosine Kinase Signaling Participates in Platelet Function", *Arterioscler. Thromv Vasc. Biol.* (2004) 24:1118-1123.

Christoph, S. et al. "UNC569, a novel small-molecule Mer inhibitor with efficacy against acute lymphoblastic leukemia in vitro and in vivo", *Mol Cancer Ther.* (2013) 12(11):2367-77.

Cook, et al. "MerTK inhibition in tumor leukocytes decreases tumor growth and metastasis" *J. Clin. Invest.* (2013) 123:3231-3242.

Earp, S. "Chemical Biology Consortium: Mer Kinase Inhibitor Studies" Presentation at the Chemical Biology Consortium, Jan. 26, 2012.

Frye, S. "Academic Drug Discovery: US Perspective and Examples" Presentation at the NCI Translational Science Meeting, Washington DC, Jul. 29, 2011.

Frye, S. "Academic Drug Discovery and Chemical Biology", Presentation at the Northwestern 18th Annual Drug Discovery Symposium. Nov. 13, 2013.

Graham, et al. "Cloning and mRNA expression analysis of a novel human protooncogene, c-mer", *Cell Growth Differ.* (1994) 5:647-657.

Lee-Sherick, et al. "Efficacy of a Mer and Flt3 tyrosine kinase small molecule inhibitor, UNC1666, in acute myeloid leukemia", *Oncotarget*, Advance Publications, Feb. 10, 2015.

Linger et al. "Mer receptor tyrosine kinase is a therapeutic target in pre-B-cell acute lymphoblastic leukemia" *Blood* (2013) 122(9):1599-1609.

Liu, J. et al. "Discovery of Novel Small Molecule Mer Kinase Inhibitors for the Treatment of Pediatric Acute Lymphoblastic Leukemia" *ACS Med. Chem. Lett.* (2012) 3(2):129-134.

Liu, J, et al. "UNC1062, a new and potent Mer inhibitor", *Eur J Med Chem.* (2013) 65:83-93.

Meertens, L. et al. "The TIM and TAM families of phosphatidylserine receptors mediate dengue virus entry", *Cell Host Microbe* (2012) 12:544-557.

Mercer, J. & Helenius, A. "Vaccinia virus uses macropinocytosis and apoptotic mimicry to enter host cells", *Science* (2008) 320:531-535.

Morizono, et al, "The Soluble Serum Protein Gas6 Bridges Virion Envelope Phosphatidylserine to the TAM Receptor Tyrosine Kinase Axl to mediate Viral Entry", *Cell Host & Microbe* (2011) 9:286-298.

Morizono and Chen, "Role of Phosphatidyl Receptors in Enveloped Virus Infection", *J. Virology* (2014) 88(8):4275-4290.

(56) References Cited

OTHER PUBLICATIONS

Paolino, M., et al. "The E3 ligase Cbl-b and TAM receptors regulate cancer metastasis via natural killer cells", *Nature* (2014) 507:508-512.
Powell et al. "Highly selective 2,4-diaminopyridine-5-carboxamide inhibitors of Sky kinase", *Bioorg. Med. Chem. Lett.* (2013) 23:1046-1050.
Powell et al. "Optimization of highly selective 2,4-diaminopyridine-5-carboxamide inhibitors of Sky kinase", *Bioorg. Med. Chem. Lett.* (2013) 23:1051-1055.
Sather, et al. "A soluble form of the Mer receptor tyrosine kinase inhibits macrophage clearance of apoptotic cells and platelet aggregation", *Blood* (2007) 109(3):1026-1033.
Schlegel et al. "MER receptor tyrosine kinase is a therapeutic target in melanoma" *J. Clin. Invest.* (2013) 123(5): 2257-67.
Shimojima, et al. "Tyro3 Family-mediated Cell Entry of Ebola and Marburg Viruses", *Journal of Virology* (2006) 80(20):10109-10116.
Zhang, W., et al. "Discovery of Mer specific tyrosine kinase inhibitors for the treatment and prevention of thrombosis", *J. Med. Chem.* (2013) 56:9693-9700.
Zhang, W., et al. "Pseudo-cyclization through intramolecular hydrogen bond enables discovery of pyridine substituted pyrimidines as new Mer kinase inhibitors", *J. Med. Chem.* (2013) 56:9683-9692.
Extended European Search Report, EP 11783985.2, mailed Oct. 15, 2013.
Extended European Search Report, EP 12839069.7, mailed May 4, 2015.
International Search Report and Written Opinion, PCT/US2011/036215, mailed Aug. 16, 2011.
International Preliminary Report on Patentability, PCT/US2011/036215, mailed Nov. 29, 2012.
International Search Report and Written Opinion, PCT/US2012/058298, mailed Dec. 7, 2012.
International Search Report and Written Opinion, PCT/US2013/042033, mailed Aug. 27, 2013.
International Preliminary Report on Patentability, PCT/US2013/042033, mailed Dec. 4, 2014.
International Search Report and Written Opinion, PCT/US2013/065192, mailed Jan. 24, 2014.
International Preliminary Report on Patentability, PCT/US2013/065192, Apr. 30, 2015.
International Search Report and Written Opinion, PCT/US2013/071409, mailed Mar. 31, 2014.
International Preliminary Report on Patentability, PCT/US2013/071409, mailed Jun. 11, 2015.
International Search Report and Written Opinion, PCT/US2015/24258, mailed Jun. 24, 2015.
International Search Report and Written Opinion, PCT/US2015/24301, mailed Jun. 25, 2015.
International Search Report and Written Opinion, PCT/US2015/24328, mailed Jun. 25, 2015.
International Search Report and Written Opinion, PCT/US2015/24362, mailed Jun. 26, 2015.
International Search Report and Written Opinion, PCT/US2015/24373, mailed Jul. 7, 2015.
International Search Report and Written Opinion, PCT/US2015/24380, mailed Jul. 1, 2015.
International Search Report and Written Opinion, PCT/US2015/24381, mailed Jul. 1, 2015.
European Search Report corresponding to European Application No. 13793925.2 dated Nov. 30, 2015.
Banker et al. *Modern Pharmaceuticals* p. 596 (1996).
Wolff et al. "Burger's Medicinal Chemistry and Drug Discovery", John Wiley & Sons, Inc. 5$^{th}$ Ed. vol. 1:975-977 (1995).
Database CAPLUS in STN, Ace. No. 2007:1144983, Guillemont et al. WO 2007/113254 A 1 (Oct. 11, 2007) (abstract).
European Search Report corresponding to European Application No. 13858929.6 dated May 3, 2016.
European Search Report corresponding to European Application No. 13847985.2 dated May 24, 2016.
Ishida et al. "Novel and orally active 5-(1,3,4-oxadiazol-2-yl)pyrimidine derivatives as selective FLT3 inhibitors", *Biooroanic & Medicinal Chemistry Letters* 18:5472-5477 (2008).
Kiyoi et al. "A Novel FLT3 Inhibitor FI-700 Selectively Suppresses the Growth of Leukemia Cells with FLT3 Mutations", *Clin Cancer Res* 13(15):4575-4582 (2007).
Pawar et al. "Synthesis of 2,4,5-Trisubstituted Pyrimidines", *Indian Journal of Heterocyclic Chemistry* 20(12):133-136 (2010).
Aso et al. "Discovery of pyrrolo[2,3-d]pyrimidin-4-ones as corticotropin-releasing factor 1 receptor antagonists with a carbonyl-based hydrogen bonding acceptor", *Bioorganic & Medicinal Chemistry Letters* 21(8):2365-2371 (2011) (Abstract Only).
Database CAPLUS [Online]—Chemical Abstracts Service, Columbus, Ohio, US; 2004, Ismail, M.A.: "Efficient synthesis of 5-(5-aryl-2-furyl)pyrimidine derivatives", Database accession No. 2004:551368; & Ismail, M.A.: "Efficient synthesis of 5-(5-aryl-2-furyl)pyrimidine derivatives", Mansoura Science Bulletin, A: Chemistry, vol. 30, No. 2, 2003, pp. 157-172 (Abstract Only).
Cancer Drug Design and Discovery Neidle, Stephen, ed. (Elsevier/Academic Press, 2008) pp. 427-431.
Notification Concerning Transmittal of International Preliminary Report on Patentability corresponding to International Application No. PCT/US2015/024381 mailed Oct. 20, 2016.
Notification Concerning Transmittal of International Preliminary Report on Patentability corresponding to International Application No. PCT/US2015/024362 mailed Oct. 20, 2016.
Notification Concerning Transmittal of International Preliminary Report on Patentability corresponding to International Application No. PCT/US2015/024328 mailed Oct. 20, 2016.
Notification Concerning Transmittal of International Preliminary Report on Patentability corresponding to International Application No. PCT/US2015/024328 mailed Oct. 13, 2016.
Notification Concerning Transmittal of International Preliminary Report on Patentability corresponding to International Application No. PCT/US2015/024373 mailed Oct. 20, 2016.
Notification Concerning Transmittal of International Preliminary Report on Patentability corresponding to International Application. No. PCT/US2015/024380 mailed Oct. 20, 2016.
Notification Concerning Transmittal of International Preliminary Report on Patentability corresponding to International Application No. PCT/US2015/024301 mailed Oct. 20, 2016.
Yu et al. "3D-QSAR modeling and molecular docking study on Mer kinase inhibitors of pyridine-substituted pyrimidines", *Mol Divers* 19:135-147 (2015).
Zhang et al. "Pseudo-Cyclization through Intramolecular Hydrogen Bond Enables Discovery of Pyridine Substituted Pyrimidines as New Mer Kinase", *J. Med. Chem.* 56:9683-9692 (2013).

\* cited by examiner

PYRIMIDINE COMPOUNDS FOR THE TREATMENT OF CANCER

RELATED APPLICATIONS

This application is a 35 U.S.C. §371 national stage application of PCT Application No. PCT/US2013/071409, filed on Nov. 22, 2013, which claims priority from U.S. Provisional Application No. 61/730,179, filed on Nov. 27, 2012, the contents of which are incorporated herein by reference in their entireties. The above-referenced PCT International Application was published as International Publication No. WO 2014/085225 A1 on Jun. 5, 2014. This application is related to PCT Application Nos. PCT/US2011/036215 filed May 12, 2011; PCT/US2012/058298 filed Oct. 1, 2012; and PCT/US2013/042033, filed May 21, 2013.

STATEMENT OF FEDERAL SUPPORT

This invention was made with government support under Grant No. HHSN261200800001E awarded by the National Institutes of Health. The government has certain rights in the invention.

FIELD OF THE INVENTION

The present invention concerns compounds, compositions and methods for the treatment of cancer.

BACKGROUND OF THE INVENTION

Acute Lymphoblastic Leukemia (ALL) is the most common malignancy in children and common varieties are cured by chemotherapy in 75%-85% of the cases. Collectively the less common T cell and rare 13 cell subsets represent less than 2000 cases yearly and thus can be classified as a rare disease; these subsets have a poorer prognosis. Unfortunately with either subset, resistance to and relapse from therapy is a major cause of pediatric cancer death. In addition, ALL chemotherapies can cause late complications that are increasingly recognized in pediatric survivor populations. In fact, in pediatric cancer survivors, the incidence of severe late effects (neurocognitive sequelae, auditory complications, cardiovascular dysfunction, gastrointestinal/hepatic dysfunction, growth delay, secondary malignancies, and infertility) directly related to therapy is approximately 25%. A better understanding of therapeutic resistance and its reversal could not only help those who relapse but may help lower the dose of chemotherapy needed in ALL patients thus reducing long-term toxicity for future survivors.

SUMMARY OF THE INVENTION

A first aspect of the invention is active compounds of Formula I or II:

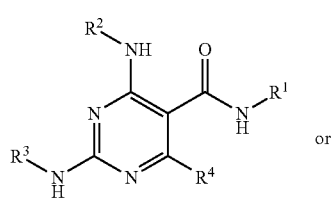

(I)

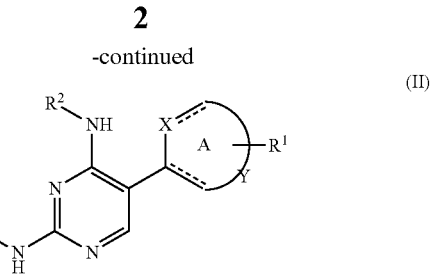

(II)

wherein:
Ring A is a 5- or 6-membered heteroaryl group such as pyridyl, pyrimidyl, thiazol, furanyl, pyridazinyl, pyrazinyl, imidazol, etc. The dashed line is an optional double bond. X is N or O. Y is C, S or N and can move on the ring.

$R^1$ is —$R^5R^6$, where $R^5$ is a covalent bond or C1 to C3 alkyl or a linker group (for example, sulfonamide, amide, etc.) and $R^6$ is cycloalkyl, heterocycloalkyl, aryl, heteroaryl alkylcycloalkyl, alkylheterocycloalkyl, alkylaryl, alkylheteroaryl, or alkyl, and wherein $R^6$ is optionally substituted one, two or three times with independently selected polar groups;

$R^2$ is —$R^7R^8$, where $R^7$ is a covalent bond or C1 to C3 alkyl and $R^8$ is cycloalkyl, heterocycloalkyl, aryl, heteroaryl or alkyl, and wherein $R^8$ is optionally substituted one, two or three times with independently selected polar groups;

$R^3$ is selected from the group consisting of H, alkyl, arylalkyl; cycloalkylalkyl, heterocycloalkylalkyl, heteroarylalkyl, and alkoxyalkyl, each of which is optionally substituted one, two or three times with independently selected polar groups;

or $R^2$ and $R^3$ together form a linking group;

$R^4$ is H, loweralkyl, halo, or loweralkoxy;

or a pharmaceutically acceptable salt thereof.

A further aspect of the invention is an active compound as described herein in a pharmaceutically acceptable carrier.

A further aspect of the invention is a method of treating cancer in a subject in need thereof, comprising administering said subject an active compound as described herein in an amount effective to treat the cancer.

A further aspect of the invention is an active compound as described herein for use in treating cancer, and/or for the preparation of a medicament for the treatment of cancer.

DETAILED DESCRIPTION OF PREFERRED EMBODIMENTS

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" or "loweralkyl" is intended to include both substituted and unsubstituted alkyl or loweralkyl unless otherwise indicated and these groups may be substituted with groups selected from halo (e.g., haloalkyl), alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S (O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralkynyl unless otherwise indicated and these groups may be substituted with the same groups as set forth in connection with alkyl and loweralkyl above.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Heteroaryl" as used herein is as described in connection with heterocyclo above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Halo" as used herein refers to any suitable halogen, including —F, —Cl, —Br, and —I.

"Mercapto" as used herein refers to an —SH group.

"Azido" as used herein refers to an —N$_3$ group.

"Cyano" as used herein refers to a —CN group.

"Formyl" as used herein refers to a —C(O)H group.

"Carboxylic acid" as used herein refers to a —C(O)OH group.

"Hydroxyl" as used herein refers to an —OH group.

"Nitro" as used herein refers to an —NO$_2$ group.

"Acyl" as used herein alone or as part of another group refers to a —C(O)R radical, where R is any suitable substituent such as aryl, alkyl, alkenyl, alkynyl, cycloalkyl or other suitable substituent as described herein.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Amino" as used herein means the radical —$NH_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —$NR_aR_b$, where $R_a$ and $R_b$ are independently selected from the groups alkyl, haloalkyl, alkenyl, alkynyl, cycloalkyl, cycloalkylalkyl, aryl, arylalkyl, heterocyclo, heterocycloalkyl.

"Acylamino" as used herein alone or as part of another group means the radical —$NR_aR_b$, where $R_a$ is an acyl group as defined herein and $R_b$ is selected from the groups hydrogen, alkyl, haloalkyl, alkenyl, alkynyl, cycloalkyl, cycloalkylalkyl, aryl, arylalkyl, heterocyclo, heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Amide" as used herein alone or as part of another group refers to a —C(O)$NR_aR_b$ radical, where $R_a$ and $R_b$ are any suitable substituent such as alkyl, cycloalkyl, alkenyl, alkynyl or aryl.

"Sulfoxyl" as used herein refers to a compound of the formula —S(O)R, where R is any suitable substituent such as alkyl, cycloalkyl, alkenyl, alkynyl or aryl.

"Sulfonyl" as used herein refers to a compound of the formula —S(O)(O)R, where R is any suitable substituent such as amino, alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid" as used herein refers to a compound of the formula —S(O)(O)OH.

"Sulfonamide" as used herein alone or as part of another group refers to a —S(O)$_2NR_aR_b$ radical, where $R_a$ and $R_b$ are any suitable substituent such as H, alkyl, cycloalkyl, alkenyl, alkynyl or aryl.

"Urea" as used herein alone or as part of another group refers to an —N(R)C(O)$NR_aR_b$ radical, where $R_a$, $R_b$ and $R_c$ are any suitable substituent such as H, alkyl, cycloalkyl, alkenyl, alkynyl or aryl.

"Alkoxyacylamino" as used herein alone or as part of another group refers to an —N($R_a$)C(O)$OR_b$ radical, where $R_a$, $R_b$ are any suitable substituent such as H, alkyl, cycloalkyl, alkenyl, alkynyl or aryl.

"Aminoacyloxy" as used herein alone or as part of another group refers to an —OC(O)$NR_aR_b$ radical, where $R_a$ and $R_b$ are any suitable substituent such as H, alkyl, cycloalkyl, alkenyl, alkynyl or aryl.

"Polar group" as used herein refers to a group wherein the nuclei of the atoms covalently bound to each other to form the group do not share the electrons of the covalent bond(s) joining them equally; that is the electron cloud is denser about one atom than another. This results in one end of the covalent bond(s) being relatively negative and the other end relatively positive; i.e., there is a negative pole and a positive pole. Examples of polar groups include, without limitations, halo, hydroxy, alkoxy, carboxy, nitro, cyano, amino (primary, secondary and tertiary), amido, ureido, sulfonamido, sulfinyl, sulfhydryl, silyl, S-sulfonamido, N-sulfonamido, C-carboxy, O-carboxy, C-amido, N-amido, sulfonyl, N-tert-butoxycarbonyl (or "t-BOC") groups, phosphono, morpholino, piperazinyl, tetrazolo, and the like. See, e.g., U.S. Pat. No. 6,878,733, as well as alcohol, thiol, polyethylene glycol, polyol (including sugar, aminosugar, uronic acid), sulfonamide, carboxamide, hydrazide, N-hydroxycarboxamide, urea, metal chelates (including macrocyclic ligand or crown ether metal chelates). The polar group can be an ionic group.

"Ionic group" as used herein includes anionic and cationic groups, and includes groups (sometimes referred to as "ionogenic" groups) that are uncharged in one form but can be easily converted to ionic groups (for example, by protonation or deprotonation in aqueous solution). Examples include but are not limited to carboxylate, sulfonate, phosphate, amine, N-oxide, and ammonium (including quaternized heterocyclic amines such as imidazolium and pyridinium) groups. See, e.g., U.S. Pat. Nos. 6,478,863; 6,800,276; and 6,896,246. Additional examples include uronic acids, carboxylic acid, sulfonic acid, amine, and moieties such as guanidinium, phosphoric acid, phosphonic acid, phosphatidyl choline, phosphonium, borate, sulfate, etc.

"Deuterium" as used herein alone or as part of another group, refers to a safe, non-radioactive relative of hydrogen. Any hydrogen in a group or substituent described above may be replaced with deuterium to provide a "deuterated" compound, in some embodiments to modify and/or improve metabolic stability, resulting in better safety, tolerability and/or efficacy.

"Linking group" or "linker group" as used herein are generally bivalent aromatic, aliphatic, or mixed aromatic and aliphatic groups. Thus linking groups include linear or branched, substituted or unsubstituted aryl, alkyl, alkylaryl, or alkylarylalkyl linking groups, where the alkyl groups are saturated or unsaturated, and where the alkyl and aryl groups optionally containing independently selected heteroatoms such as 1, 2, 3 or 4 heteroatoms selected from the group consisting of N, O, and S. In some embodiments, linking groups containing from 2 to 20 carbon atoms are preferred. Numerous examples of suitable linking groups are known, including but not limited to those described in, U.S. Pat. Nos. 8,247,572; 8,097,609; 6,624,317; 6,613,345; 6,596,935; and 6,420,377, the disclosures of which are incorporated by reference herein in their entirety.

"Treat" as used herein refers to any type of treatment that imparts a benefit to a patient afflicted with a disease, including improvement in the condition of the patient (e.g., in one or more symptoms), delay in the progression of the disease, delay in onset of the disease, etc.

"Pharmaceutically acceptable" as used herein means that the compound or composition is suitable for administration to a subject to achieve the treatments described herein, without unduly deleterious side effects in light of the severity of the disease and necessity of the treatment.

Active compounds of the present invention may optionally be administered in conjunction with other compounds useful in the treatment of cancer. The other compounds may optionally be administered concurrently. As used herein, the word "concurrently" means sufficiently close in time to produce a combined effect (that is, concurrently may be simultaneously, or it may be two or more events occurring within a short time period before or after each other).

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes. Subjects may be of any age, including infant, juvenile, adolescent, adult, and geriatric subjects.

1. Active Compounds.

As noted above, the present invention provides active compounds of Formula I or II:

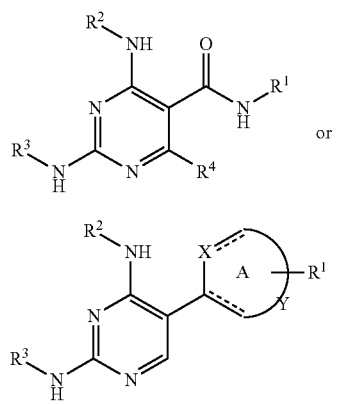

wherein:

$R^1$ is —$R^5R^6$, where $R^5$ is a covalent bond, C1 to C3 alkyl or a linker group (for example, sulfonamide, amide, etc.) and $R^6$ is cycloalkyl, heterocycloalkyl, aryl, heteroaryl, alkylcycloalkyl, alkylheterocycloalkyl, alkylaryl, alkylheteroaryl or alkyl, and wherein $R^6$ is optionally substituted one, two or three times with independently selected polar groups;

$R^2$ is —$R^7R^8$, where $R^7$ is a covalent bond or C to C3 alkyl and $R^8$ is cycloalkyl, heterocycloalkyl, aryl, heteroaryl or alkyl, and wherein $R^8$ is optionally substituted one, two or three times with independently selected polar groups;

$R^3$ is selected from the group consisting of H, alkyl, arylalkyl; cycloalkylalkyl, heterocycloalkylalkyl, heteroarylalkyl, and alkoxyalkyl, each of which is optionally substituted one, two or three times with independently selected polar groups;

or $R^2$ and $R^3$ together form a linking group;

$R^4$ is H, loweralkyl, halo, or loweralkoxy;

or a pharmaceutically acceptable salt thereof.

In some embodiments of the foregoing, $R^5$ is a covalent bond; in other embodiments, $R^5$ is C1 to C3 alkylene such as —$CH_2$— or $R^5$ is a linker group (for example, sulfonamide, amide, etc.).

In some embodiments of the foregoing, $R^7$ is a covalent bond; in other embodiments, $R^7$ is C1 to C3 alkylene such as —$CH_2$—.

In some embodiments, $R^6$ is phenyl, piperidyl, or C1-C8 alkyl, or C3 to C8 cycloalkyl, which phenyl, pipyridyl, alkyl, or cycloalkyl alkyl is unsubstituted or substituted from 1 to 3 times with sulfono, halo, amino, nitro, alkyl, alkoxyl, haloalkyl, cycloalkyl, heterocycloalkyl, aryl, or heteroaryl.

In some embodiments, wherein $R^8$ is C1-C8 alkyl or cyclohexyl, which alkyl or cyclohexyl is unsubstituted or substituted from 1 to 3 times with hydroxyl or amino.

In some embodiments, $R^3$ is C1-C8 alkyl, C3-C8 cycloalkyl, C4-C12 cycloalkylalkyl, C3-C8 heterocycloalkyl, C4-C12 heterocycloalkylalkyl, C4-C12 arylalkyl, C4-C12 heteroarylalkyl, each of which is unsubstituted or substituted from one to three times with hydroxyl, halo, or alkoxy.

In some embodiments, $R^4$ is H.

Specific examples of linking groups include, but are not limited to:

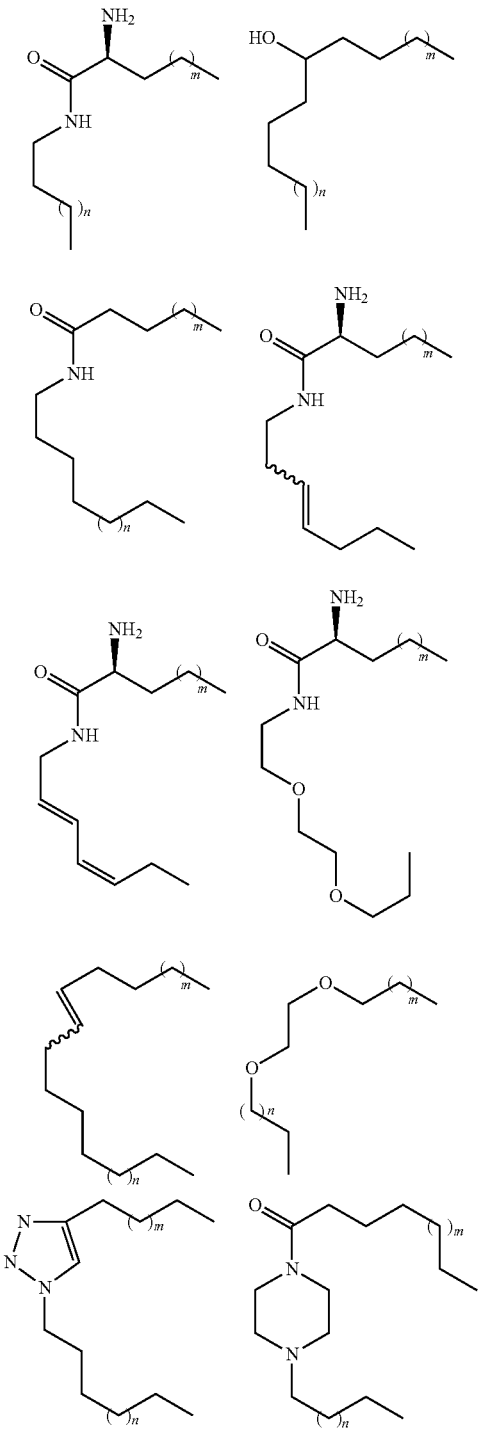

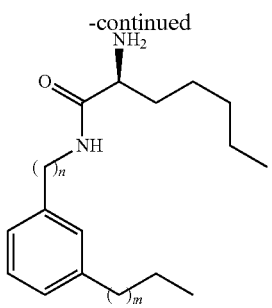

where each n and m is independently 0, 1, 2, 4, 5, or 6; and where each of the linking group structures illustrated above may optionally be substituted, e.g., substituted one, two, or three times with independently selected polar groups.

Particular examples of compounds of the present invention include but are not limited to those set forth in Tables 1-7 below.

The active compounds disclosed herein can, as noted above, be provided in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

Active compounds as described herein can be prepared in accordance with known procedures, or variations thereof that will be apparent to those skilled in the art.

2. Pharmaceutical Formulations.

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces), transdermal administration, and intraventricular injection (injection into a ventricle of the brain, e.g., by an implanted catheter or omman reservoir, such as in the case of morbid obesity) and although the most suitable route in any given case will depend on the nature and severity of the condition being treated and on the nature of the particular active compound which is being used.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds of formula (I) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration.

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. In some embodiments, a dosage from about 0.5 mg/kg to 5 mg/kg may be employed for intramuscular injection. In some embodiments, dosages are 1 µmol/kg to 50 µmol/kg, and more preferably 22 µmol/kg and 33 µmol/kg of the compound for intravenous or oral administration. The duration of the treatment can be once per day for a period of two to three weeks or until the condition is essentially controlled.

Active compounds may be administered as pharmaceutically acceptable prodrugs, which are those prodrugs of the active compounds of the present invention which are, within the scope of sound medical judgment, suitable for use in contact with the tissues of humans and lower animals without undue toxicity, irritation, allergic response and the like, commensurate with a reasonable risk/benefit ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein. See also U.S. Pat. No. 6,680,299 Examples include a prodrug that is metabolized in vivo by a subject to an active drug having an activity of active compounds as described herein, wherein the prodrug is an ester of an alcohol or carboxylic acid group, if such a group is present in the compound; an acetal or ketal of an alcohol group, if such a group is present in the compound; an N-Mannich base or an imine of an amine group, if such a group is present in the compound; or a Schiff base, oxime, acetal, enol ester, oxazolidine, or thiazolidine of a carbonyl group, if such a group is present in the compound, such as described in U.S. Pat. No. 6,680,324 and U.S. Pat. No. 6,680,322.

As noted above, the active compounds described herein are useful for the treatment of cancer. Example cancers that may be treated by the compounds and methods of the invention include, but are not limited to, myeloid leukemia, lymphoblastic leukemia, melanoma, breast, lung, colon, liver, gastric, kidney, ovarian, uterine, and brain cancer.

The present invention is explained in greater detail in the following non-limiting Examples.

EXAMPLES 1-11

General Structure I

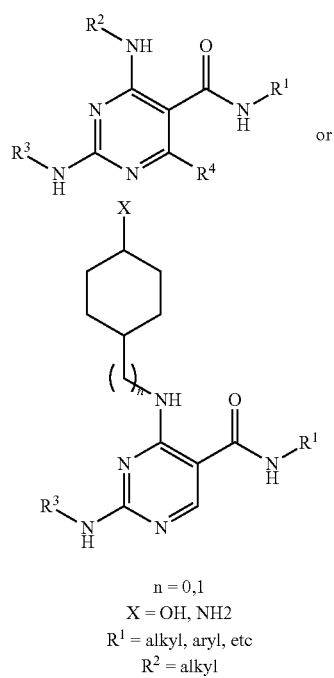

n = 0,1
X = OH, NH2
R¹ = alkyl, aryl, etc
R² = alkyl

Example 1

2-(Butylamino)-4-(((1r,4r)-4-hydroxycyclohexyl)amino)-N-(4-(morpholinosulfonyl)phenyl)pyrimidine-5-carboxamide General Procedure A

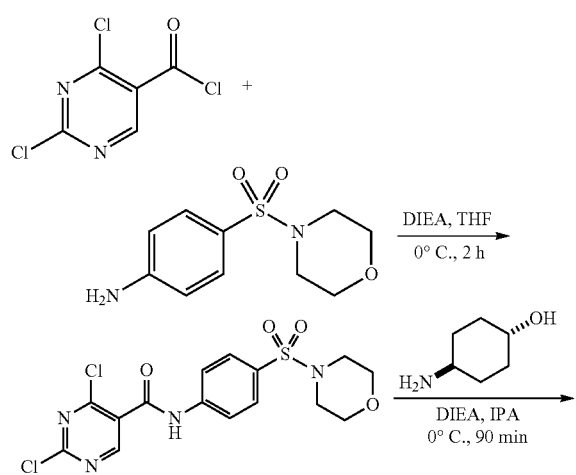

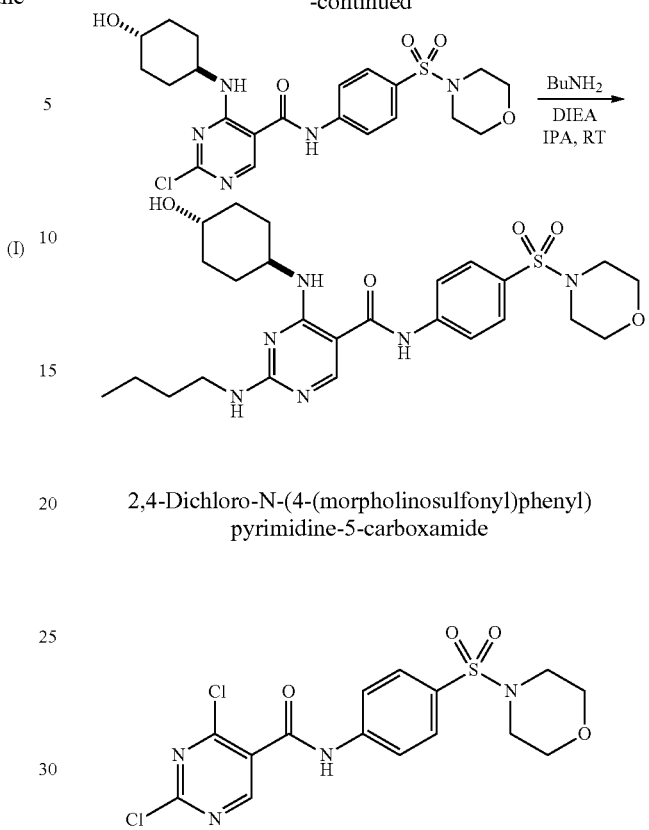

2,4-Dichloro-N-(4-(morpholinosulfonyl)phenyl)pyrimidine-5-carboxamide

A solution of 2,4-dichloropyrimidine-5-carbonyl chloride (422 mg, 2.0 mmol) in dichloromethane (10 mL) was added 4-(morpholinosulfonyl)aniline (508 mg, 2.1 mmol) and DIEA (387 mg, 3.0 mmol) at 0° C. The resulting mixture was stirred at 0° C. for 1 h. Then, water was added. The resulting mixture was extracted with EtOAc (3×). The combined organic layers were dried (Na$_2$SO$_4$), filtered and concentrated. The residue was purified on ISCO to give the title compound as a white solid (701.2 mg, 84%). $^1$H NMR (400 MHz, DMSO-d$^6$) δ 11.98-11.90 (m, 1H), 8.29 (d, J=6.4 Hz, 1H), 7.89 (d, J=8.8 Hz, 2H), 7.69 (d, J=8.8 Hz, 2H), 3.65-3.56 (m, 41H), 2.87-2.78 (m, 4H); MS m/z 418.30 [M+H]$^+$.

2-Chloro-4-(((1r,4r)-4-hydroxycyclohexyl)amino)-N-(4-(morpholinosulfonyl)phenyl) pyrimidine-5-carboxamide A solution of 2,4-dichloro-N-(4-(morpholinosulfonyl)phenyl)pyrimidine-5-carboxamide (700 mg, 1.68 mmol) in IPA (15 mL) was added trans-4-aminocyclohexanol (231.4 mg, 2.2 mmol) and DIEA (387 mg, 3.0 mmol) at 0° C. The resulting mixture was stirred at 0° C. for 50 min and warmed to room temperature and stirred for another 50 min. Then the solvent was removed, the residue was dissolved in a mixture of CH2CL2 and methanol (20 mL, 3:2, v/v), the suspension was filtered though a filter paper to give the title compound as a white solid (683.4 mg, 82%). $^1$H NMR (400 MI-Hz, DMSO-d$^6$) δ 10.71 (s, 1H), 8.69 (s, 1H), 7.96-7.89 (m, 2H), 7.76-7.70 (m, 2H), 4.57 (s, 1H), 3.93-3.81 (m, 1H), 3.64-3.57 (m, 4H), 3.49-3.40 (m, 1H), 2.88-2.78 (m, 4H), 1.95-1.86 (m, 2H), 1.85-1.76 (m, 2H), 1.38-1.20 (m, 4H); MS m/z 496.20 [M+H]$^+$.

2-(Butylamino)-4-(((1r,4r)-4-hydroxycyclohexyl)amino)-N-(4-(morpholinosulfonyl)phenyl)pyrimidine-5-carboxamide

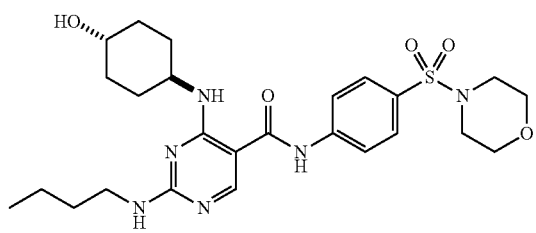

A solution of 2-chloro-4-(((1r,4r)-4-hydroxycyclohexyl)amino)-N-(4-(morpholinosulfonyl)phenyl) pyrimidine-5-carboxamide (86 mg, 0.17 mmol) in IPA (10 mL) was added butylamine (59.6 mg, 0.81 mmol) and DIEA (124.7 mg, 0.96 mmol) at room temperature. The resulting mixture was stirred for 3 h at room temperature. Water was then added. The resulting mixture was extracted with EtOAc (3×). The combined organic layers were dried (Na$_2$SO$_4$), filtered and concentrated. The residue was purified on ISCO to give the title compound as a white solid (59.3 mg, 64%). $^1$H NMR (400 MHz, CD$_3$OD+CDCl$_3$) δ 8.21 (s, 1H), 7.71-7.64 (m, 2H), 7.59-7.53 (m, 2H), 3.93-3.77 (m, 1H), 3.74-3.64 (m, 4H), 3.63-3.58 (m, 4H), 3.56-3.46 (m, 1H), 3.26 (t, J=7.1 Hz, 2H), 2.91-2.81 (m, 4H), 2.05-1.95 (m, 2H), 1.93-1.82 (m, 2H), 1.50-1.41 (m, 2H), 1.33-1.17 (m, 6H), 0.83 (t, J=7.3 Hz, 3H); $^{13}$C NMR (101 MHz, CD$_3$OD+CDCl$_3$) δ 166.8, 156.4, 143.5, 128.8, 128.6, 120.3, 120.2, 69.2, 66.0, 45.9, 41.0, 33.4, 31.6, 30.2, 20.0, 13.7; MS m/z 533.30 [M+H]$^+$.

Example 2

2-(Butylamino)-N-(4-fluorobenzyl)-4-(((trans-4-hydroxycyclohexyl)amino)pyrimidine-5-carboxamide General Procedure B

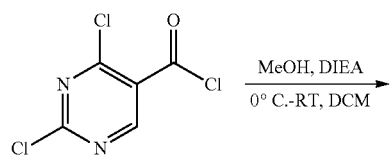

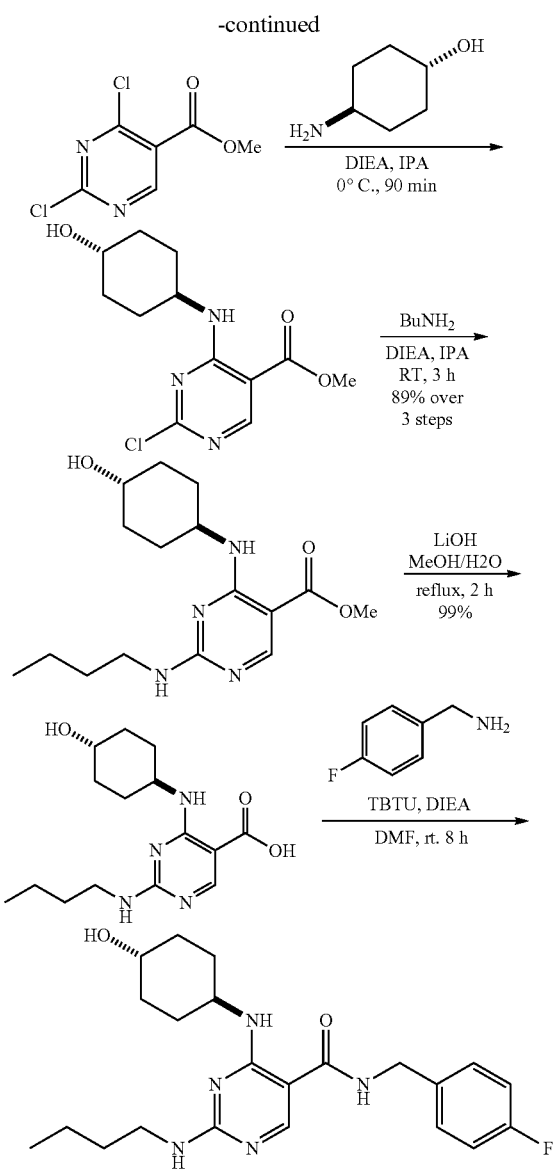

Methyl 2-(butylamino)-4-(((trans)-4-hydroxycyclohexyl)amino)pyrimidine-5-carboxylate

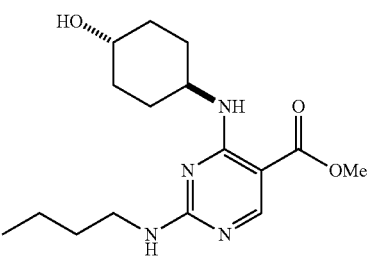

To a solution of 2,4-dichloropyrimidine-5-carbonyl chloride (500 mg, 2.38 mmol) in dichloromethane (30 mL) was added methanol (87.6 mg, 2.73 mmol) and diisopropylethylamine (369 mg, 2.86 mmol) at 0° C. The resulting mixture was stirred for 1 h at 0° C. Then the solvent was removed.

The residue (461 mg, 94%) was dissolved in IPA (20 mL) and followed by the addition of trans-4-aminocyclohexanol (301.6 mg, 2.62 mmol) then DIEA (461.4 mg, 3.57 mmol) dropwisely. The resulting mixture was stirred at 0° C. for 90 min. After which butylamine (208.8 mg, 2.86 mmol) was added, followed by DIEA (461.4 mg, 3.57 mmol). The resulting mixture was stirred at room temperature for 3 h. Water was then added. The resulting mixture was extracted with EtOAc (3×). The combined organic layers were dried (Na$_2$SO$_4$), filtered and concentrated. The residue was purified on ISCO to give methyl 2-(butylamino)-4-(((trans-4-hydroxycyclohexyl)amino)pyrimidine-5-carboxylate (682.6 mg, 89% over 3 steps). $^1$H NMR (400 MHz, CDCl$_3$) δ 9.21 (s, 1H), 8.77 (s, 1H), 6.29 (s, 1H), 4.81-4.64 (m, 1H), 4.51 (s, 3H), 4.46-4.38 (m, 1H), 4.13-4.11 (m, 2H), 2.89-2.81 (m, 2H), 2.74 (d, J=9.7 Hz, 2H), 2.35-2.25 (m, 2H), 2.23-2.00 (m, 6H), 1.67 (t, J=7.2 Hz, 3H); $^{13}$C NMR (101 MHz, CDCl$_3$) δ 167.9, 162.5, 161.3, 160.3, 95.5, 69.7, 51.2, 48.3, 41.1, 33.8, 31.7, 30.3, 20.1, 13.8; MS m/z 323.20 [M+H]$^+$.

2-(Butylamino)N-(4-fluorobenzyl)-4-(((trans)-4-hydroxycyclohexyl)amino)pyrimidine-5-carboxamide

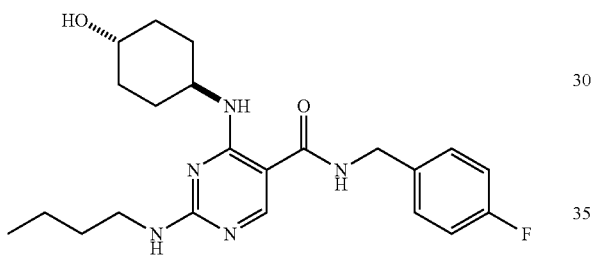

A mixture of methyl 2-(butylamino)-4-(((trans-4-hydroxycyclohexyl)amino) pyrimidine-5-carboxylate (682.6 mg, 2.12 mmol) and lithium hydroxide monohydrate (888.4 mg, 21.2 mmol) in a mixture of methanol and water (25 mL, 3:2, v/v) was heated at reflux for 2 h. Then the reaction mixture was cooled to room temperature and acidified by a 4.0N solution of HCl (4N) to PH 3. The resulting mixture was extracted with EtOAc (4×). The combined organic layers were dried (Na$_2$SO$_4$) and concentrated to provide 2-(butylamino)-4-(((1r,4r)-4-hydroxycyclohexyl)amino)pyrimidine-5-carboxylic acid (647.1 mg, 99%), which was used in the next step without further purifications. MS m/z 309.30 [M+H]$^+$.

A solution of the acid (61 mg, 0.20 mmol), O-(benzotriazol-1-yl)-N,N,N',N'-tetramethyluronium tetrafluoroborate (TBTU, 81.4 mg, 0.25 mmol, 1.3 eq) and N,N-diisopropylethylamine (DIEA, 77.5 mg, 0.60 mmol, 3.0 eq) in anhydrous DMF (3.0 mL) and was added 4-fluorobenzylamine (37.5 mg, 0.30 mmol, 1.5 eq) in DMF (1.0 mL) dropwisely at room temperature. The resulting mixture was stirred for overnight, then diluted with EtOAc (15 mL) and washed with water (3×). The organic layer was dried (Na$_2$SO$_4$) and concentrated. The residue was purified on HPLC to give the title compound (61.5 mg, 74%) as a yellow solid. $^1$H NMR (400 MHz, CDCl$_3$) δ 9.57 (d, J=7.4 Hz, 1H), 8.77 (s, 1H), 8.13 (s, 1H), 7.40-7.31 (m, 1H), 7.29-7.22 (m, 3H), 7.00 (t, J=8.6 Hz, 2H), 4.44 (d, J=5.2 Hz, 2H), 4.00 (s, 1H), 3.77-3.62 (m, 1H), 3.40 (dd, J=13.0, 6.9 Hz, 2H), 2.15-2.09 (m, 2H), 2.04 (d, J=7.6 Hz, 2H), 1.66-1.54 (m, 2H), 1.49-1.33 (m, 6H), 0.94 (t, J=7.3 Hz, 3H); MS m/z 416.30 [M+H]$^+$.

General Structure IIa, IIb, IIc

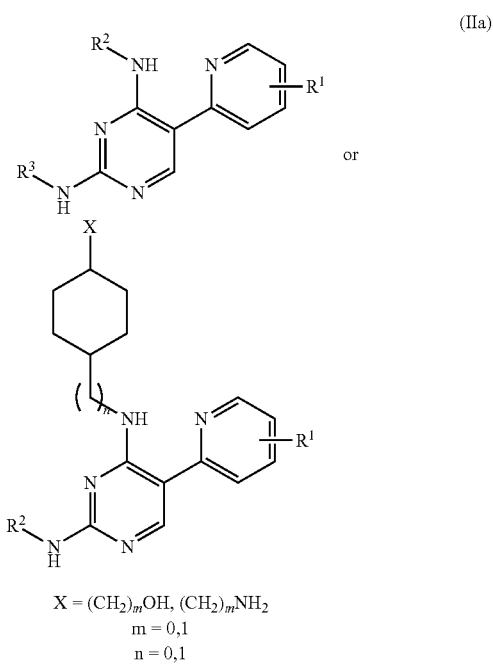

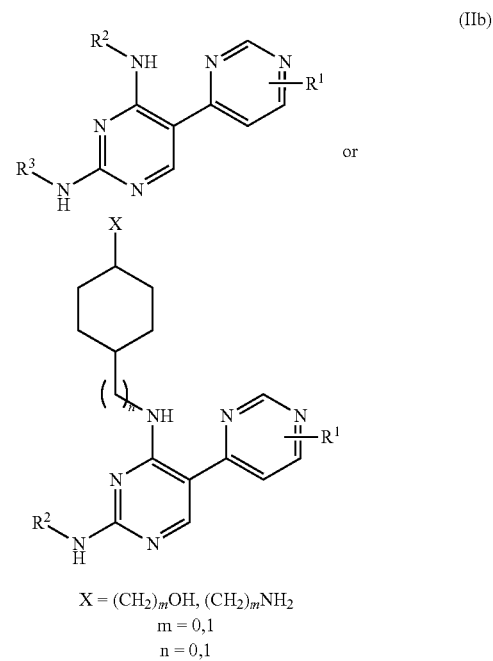

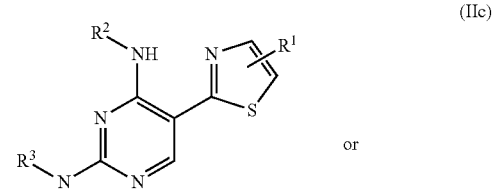

-continued

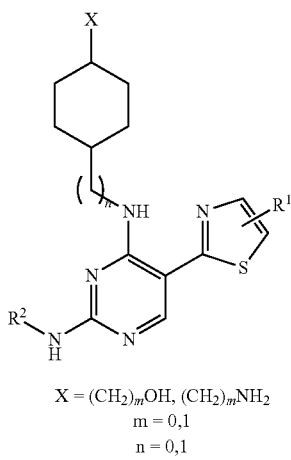

X = (CH$_2$)$_m$OH, (CH$_2$)$_m$NH$_2$
m = 0,1
n = 0,1

Example 3

(1r,4r)-4-((2-(Butylamino)-5-(5-(morpholinosulfonyl)pyridin-2-yl)pyrimidin-4-yl)amino)cyclohexanol General Procedure C

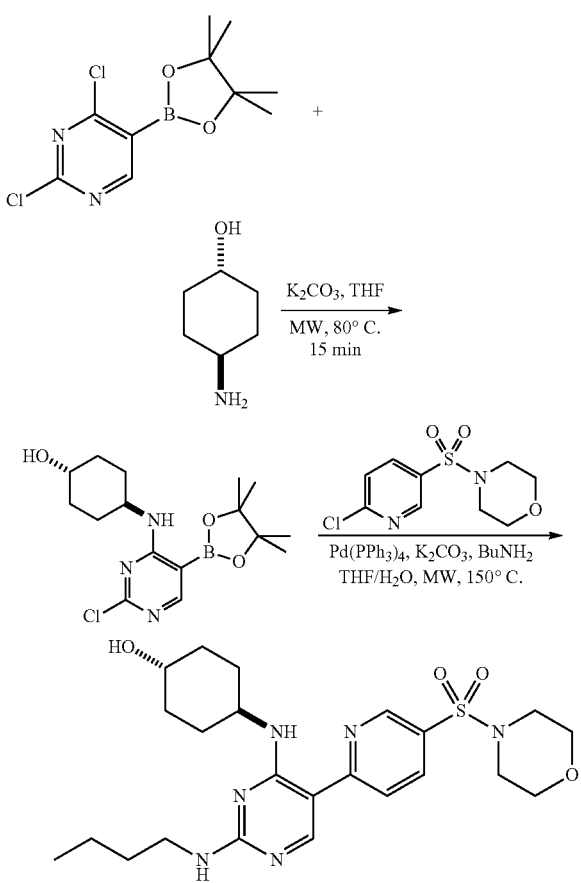

4-((6-Chloropyridin-3-yl)sulfonyl)morpholine

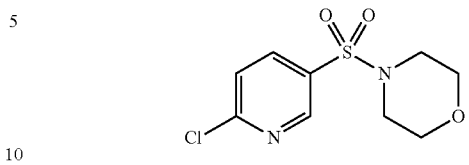

A solution of 2-chloropyridine-5-sulfonyl chloride (212 mg, 1.0 mmol) in CH2Cl2 (10 mL) was added morpholine (87.1 mg, 1.0 mmol) at 0° C. The resulting mixture was stirred at 0° C. for 10 min and then DIEA (194 mg, 1.5 mmol) was added dropwisely. The mixture was stirred at 0° C. for 2 h. Then the mixture was diluted with EtOAc (15 mL) and washed with water (2×). The organic layer was dried (Na$_2$SO$_4$), filtered and concentrated. The residue was purified on ISCO to give the title compound as a white solid (246.1 mg, 94%). $^1$H NMR (400 MHz, CDCl$_3$) δ 8.73-8.65 (m, 1H), 7.94 (dd, J=8.3, 2.5 Hz, 1H), 7.49 (dd, J=8.3, 0.6 Hz, 1H), 3.74-3.63 (m, 4H), 2.99 (dd, J=5.6, 3.9 Hz, 4H); $^{13}$C NMR (101 MHz, cdcl3) δ 155.9, 148.7, 137.9, 131.1, 124.9, 65.9, 45.8; MS m/z 263.30 [M+H]$^+$.

(1r,4r)-4-((2-(Butylamino)-5-(5-(morphinolinosulfonyl)pyridin-2-yl)pyrimidin-4-yl)amino)cyclohexanol

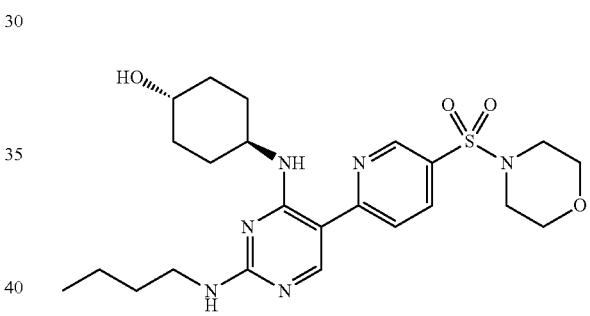

A 10 mL microwave tube was charged with 2,4-dichloropyrimidine-5-boronic acid pinacol ester (55 mg, 0.20 mmol), K$_2$CO$_3$ (41.5 mg, 0.30 mmol) and THF (2.0 mL). The resulting mixture was then heated to 80° C. for 15 min under Microwave irradiation. Then 4-((6-chloropyridin-3-yl)sulfonyl)morpholine (52.5 mg, 0.20 mmol), Pd(PPh$_3$)$_4$ (23.1 mg, 0.02 mmol), K$_2$CO$_3$ (41.5 mg, 0.30 mmol), butylamine (116.8 mg, 1.60 mmol) and water (0.5 mL) were added sequentially. The resulting mixture was heated to 150° C. for 30 min under Microwave irradiation. The mixture was diluted with EtOAc (15 mL) and washed with water (2×). The organic layer was dried (Na$_2$SO$_4$), filtered and concentrated. The residue was purified on ISCO and HPLC to give the title compound as a white solid (27.4 mg, 28%) and (1r,4r)-4-((2-(butylamino)pyrimidin-4-yl)amino)cyclohexanol (25.7 mg, 49%). $^1$H NMR (400 MHz, CDCl$_3$) δ 10.65 (d, J=7.1 Hz, 1H), 9.46 (t, J=5.4 Hz, 1H), 8.87 (d, J=2.2 Hz, 1H), 8.31 (s, 1H), 8.10 (dd, J=8.6, 2.3 Hz, 1H), 7.77 (d, J=8.7 Hz, 1H), 4.19-4.09 (m, 1H), 3.84-3.68 (m, 5H), 3.51-3.44 (m, 2H), 3.15-3.06 (m, 4H), 2.86-2.66 (m, 3H), 2.28-2.15 (m, 2H), 2.13-2.01 (m, 2H), 1.72-1.61 (m, 2H), 1.56-1.36 (m, 6H), 0.96 (t, J=7.4 Hz, 3H); $^{13}$C NMR (101 MHz, CDCl$_3$) δ 159.4, 156.9, 153.1, 146.6, 142.8, 136.8, 130.2, 118.9, 103.4, 69.2, 66.0, 49.7, 45.8, 41.3, 33.3, 31.0, 29.5, 20.1, 13.7; MS m/z 491.30 [M+H]$^+$.

Example 4
UNC2427A
General Procedure D
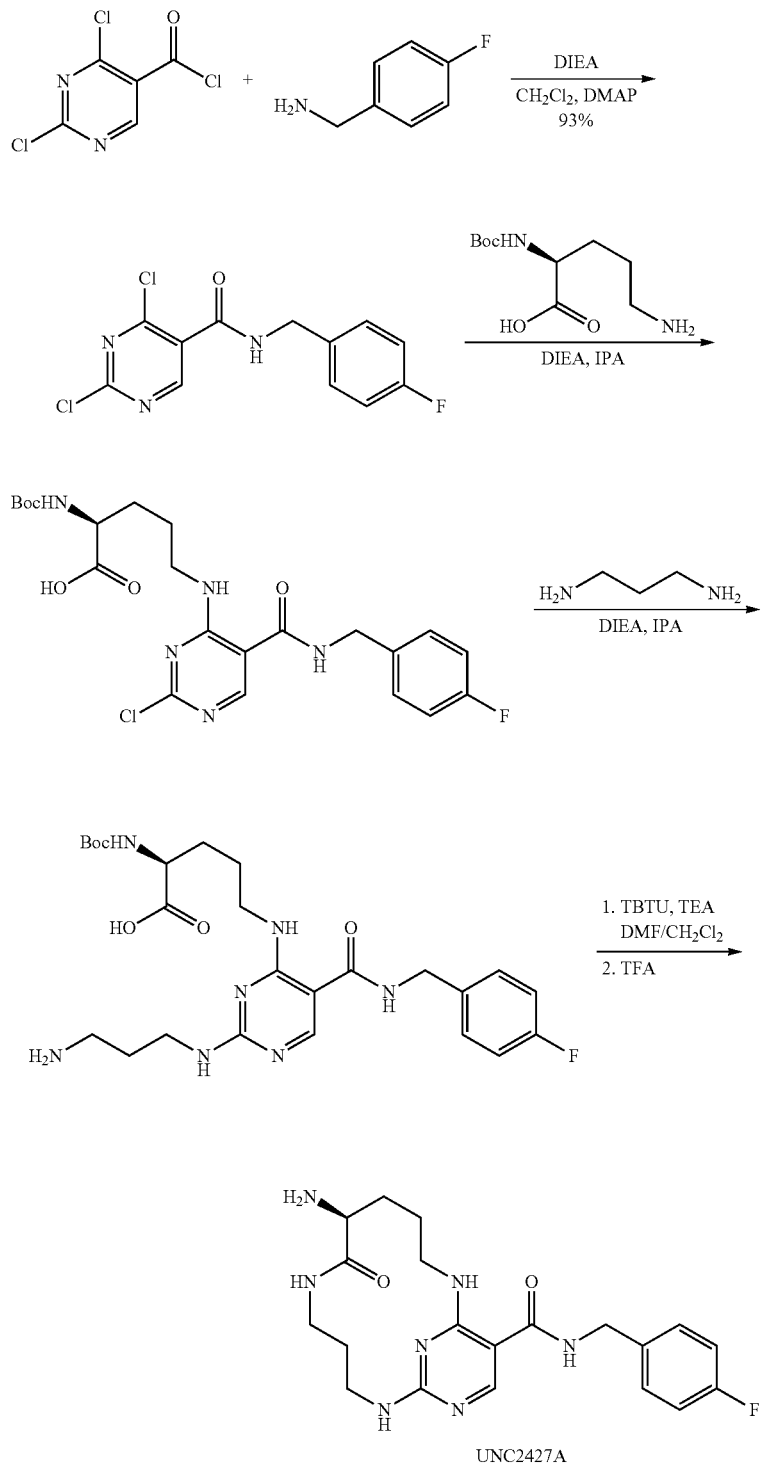
UNC2427A

2,4-Dichloro-N-(4-fluorobenzyl)pyrimidine-5-carboxamide

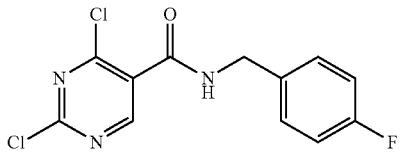 [SMILES: O=C(NCc1ccc(F)cc1)c1cnc(Cl)nc1Cl]

4-Fluorobenzylamine (1.78 g, 14.2 mmol) in dichloromethane (5.0 mL) was added into a solution of 2,4-dichloropyrimidine-5-carbonyl chloride (3.0 g, 14.2 mmol) in dichloromethane (30 mL) at 0° C. Then N,N-diisopropylethylamine (2.75 g, 21.3 mmol) and 4-(dimethylamino)pyridine (17.1 mg, 0.14 mmol) were added into the mixture. The resulting mixture was allowed to warm to room temperature and stirred for 20 min. The solvent was removed and the residue was dissolved in dichloromethane and washed with water (2×). Solvent was removed and the residue was purified on ISCO to provide the title compound (3.96 g, 93%). $^1$H NMR (400 MHz, CD$_3$OD) δ 8.73 (s, 1H), 7.42-7.35 (m, 2H), 7.12-7.02 (m, 2H), 4.53 (s, 2H); MS m/z 301.30 [M+H]$^+$.

(S)-5-((2-((3-Aminopropyl)amino)-5-((4-fluorobenzyl)carbamoyl)pyrimidin-4-yl)amino)-2-((tert-butoxycarbonyl)amino)pentanoic acid

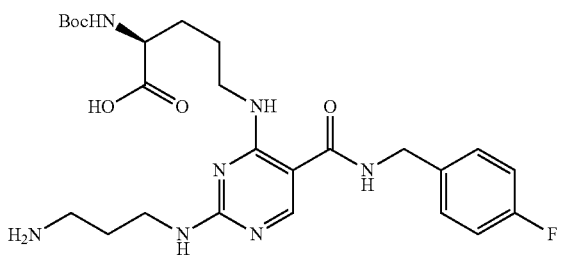 [SMILES: CC(C)(C)OC(=O)N[C@@H](CCCNc1nc(NCCCN)ncc1C(=O)NCc1ccc(F)cc1)C(=O)O]

L-Ornithine (232 mg, 1.0 mmol), N,N-diisopropylethylamine (194 mg, 1.5 mmol) were added into a solution of 2,4-dichloro-N-(4-fluorobenzyl)pyrimidine-5-carboxamide (300 mg, 1.0 mmol) in a mixture of isopropyl alcohol and DMF (10 mL, 3:2, v/v) at room temperature. The resulting mixture was stirred for overnight. Then ⅓ of the reaction mixture was added to a solution of 1,3-diaminopropane (304 mg, 4.0 mmol) in DMF (1.0 mL) at room temperature. The reaction mixture was heated at 45° C. for 2 h. The solvent was removed and the residue was purified on HPLC to give the title compound as TFA salt (92 mg, 34%). $^1$H NMR (400 MHz, CD$_3$OD) δ 8.22 (s, 1H), 7.38-7.28 (m, 2H), 7.06-6.95 (m, 2H), 4.45 (s, 2H), 4.18-4.09 (m, 1H), 3.69-3.53 (m, 4H), 3.08-2.99 (m, 2H), 2.05-1.97 (m, 2H), 1.91-1.83 (m, 1H), 1.80-1.66 (m, 3H), 1.41 (s, 9H); MS m/z 534.30 [M+H]$^+$.

UNC2427A

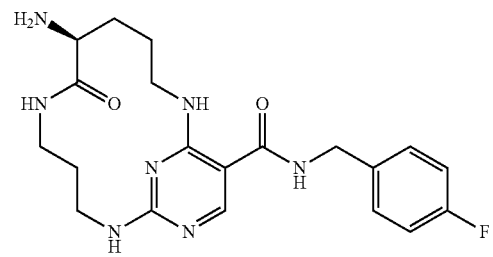 [SMILES: N[C@H]1CCCNc2nc(ncc2C(=O)NCc2ccc(F)cc2)NCCCNC1=O]

O-(benzotriazol-1-yl)-N,N,N',N'-tetramethyluronium tetrafluoroborate (TBTU, 68.3 mg, 0.21 mmol) and triethylamine (43.5 mg, 0.43 mmol) were added to the solution of (S)-5-((2-((3-aminopropyl)amino)-5-((4-fluorobenzyl)carbamoyl)pyrimidin-4-yl)amino)-2-((tert-butoxycarbonyl)amino)pentanoic acid (70 mg, 0.085 mmol) in DMF (50 mL). The resulting mixture was diluted with dichloromethane (60 mL) and stirred at room temperature for overnight. Then the solvent was removed, the residue was dissolved in dichloromethane (5.0 mL) followed by the addition of TFA (1.0 mL). The resulting mixture was stirred at room temperature for 2.0 h. Then the solvent was removed and the residue was purified on HPLC to provide the title compound (UNC2427A) as TFA salt (27.4 mg, 46%); $^1$H NMR (400 MHz, CD$_3$OD) δ 8.19 (s, 1H), 7.37-7.26 (m, 2H), 7.06-6.97 (m, 2H), 4.44 (s, 2H), 4.02-3.97 (m, 1H), 3.97-3.89 (m, 1H), 3.81-3.71 (m, 1H), 3.68-3.60 (m, 1H), 3.28-3.12 (m, 2H), 2.87-2.80 (m, 1H), 2.01-1.92 (m, 2H), 1.91-1.82 (m, 1H), 1.80-1.64 (m, 3H). MS m/z 416.25 [M+H]$^+$.

Table 1 describes compounds prepared following procedures described in Example 4 (General Procedure D), using appropriate reagents.

| | Structure | Compound_ID | Mer IC$_{50}$ | Physical Data MS m/z (M + 1) or/and $^1$H NMR |
|---|---|---|---|---|
| 1 | ![structure] | UNC2429A | ++ | $^1$H NMR (400 MHz, CD$_3$OD) δ 8.19 (s, 1H), 7.37-7.29 (m, 2H), 7.07-6.97 (m, 2H), 4.44 (s, 2H), 3.91-3.79 (m, 2H), 3.77-3.69 (m, 1H), 3.65-3.58 (m, 1H), 3.27-3.13 (m, 3H), 2.98-2.92 (m, 4H), 1.94-1.77 (m, 3H), 1.73-1.52 (m, 5H), 1.48-1.34 (m, 3H); MS m/z 444.30 [M + H]$^+$. |

Table 1 describes compounds prepared following procedures described in Example 4 (General Procedure D), using appropriate reagents.

| | Structure | Compound_ID | Mer IC$_{50}$ | Physical Data MS m/z (M + 1) or/and $^1$H NMR |
|---|---|---|---|---|
| 2 | 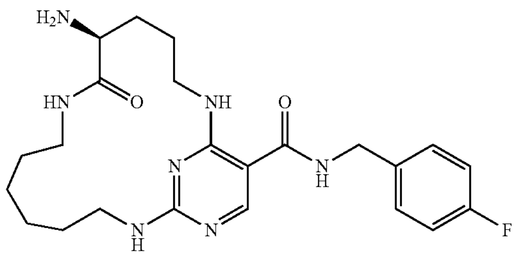 [SMILES: N[C@H]1CCCNc2nc(ncc2C(=O)NCc2ccc(F)cc2)NCCCCCCNC1=O] | UNC2430A | ++ | $^1$H NMR (400 MHz, CD$_3$OD) δ 8.20 (d, J = 0.9 Hz, 1H), 7.38-7.29 (m, 2H), 7.07-6.99 (m, 2H), 4.44 (s, 2H), 3.88-3.66 (m, 4H), 3.51-3.32 (m, 2H), 3.21-3.11 (m, 1H), 2.98-2.93 (m, 4H), 2.89-2.77 (m, 1H), 1.98-1.85 (m, 2H), 1.84-1.58 (m, 5H), 1.56-1.48 (m, 1H), 1.46-1.29 (m, 5H); MS m/z 458.30 [M + H]$^+$. |
| 3 | 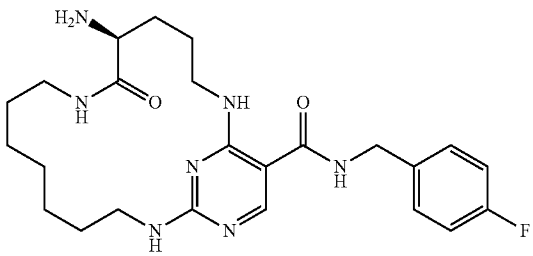 [SMILES: N[C@H]1CCCNc2nc(ncc2C(=O)NCc2ccc(F)cc2)NCCCCCCCNC1=O] | UNC2479A | ++ | $^1$H NMR (400 MHz, CD$_3$OD) δ 8.21 (s, 1H), 7.36-7.30 (m, 2H), 7.07-6.99 (m, 2H), 4.45 (s, 2H), 3.94-3.85 (m, 1H), 3.80-3.74 (m, 1H), 3.74-3.65 (m, 1H), 3.55-3.45 (m, 2H), 3.38-3.30 (m, 1H), 3.23-3.11 (m, 1H), 2.96 (s, 1H), 2.89-2.80 (m, 1H), 1.97-1.81 (m, 2H), 1.77-1.55 (m, 5H), 1.54-1.43 (m, 2H), 1.43-1.21 (m, 7H); MS m/z 472.30 [M + H]$^+$. |
| 4 | 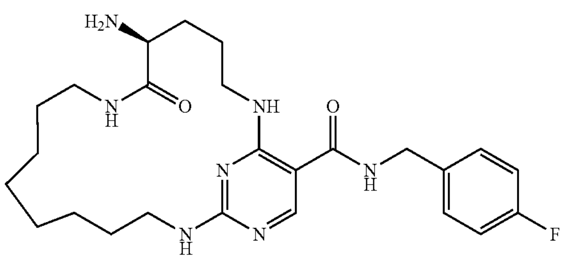 [SMILES: N[C@H]1CCCNc2nc(ncc2C(=O)NCc2ccc(F)cc2)NCCCCCCCCNC1=O] | UNC2431A | +++ | $^1$H NMR (400 MHz, CH$_3$OD) δ 8.22 (s, 1H), 7.37-7.28 (m, 2H), 7.07-6.97 (m, 2H), 4.45 (s, 2H), 3.89-3.79 (m, 2H), 3.71-3.58 (m, 2H), 3.58-3.49 (m, 1H), 3.44-3.34 (m, 1H), 2.95 (s, 1H), 2.90-2.80 (m, 1H), 1.98-1.84 (m, 2H), 1.74-1.66 (m, 2H), 1.65-1.57 (m, 2H), 1.56-1.51 (m, 1H), 1.50-1.42 (m, 1H), 1.39-1.25 (m, 8H); MS m/z 486.30 [M + H]$^+$. |
| 5 | 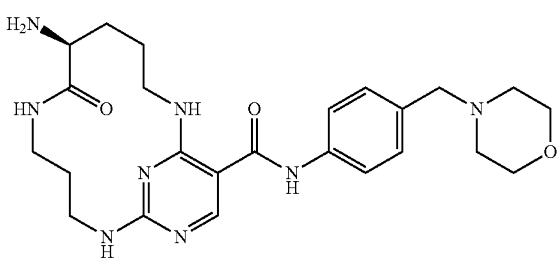 [SMILES: N[C@H]1CCCNc2nc(ncc2C(=O)Nc2ccc(CN3CCOCC3)cc2)NCCCNC1=O] | UNC2342A | ++ | $^1$H NMR (400 MHz, CD$_3$OD) δ 8.44 (d, J = 2.5 Hz, 1H), 7.81-7.73 (m, 2H), 7.53-7.46 (m, 2H), 4.33 (s, 2H), 4.07-3.93 (m, 4H), 3.82-3.64 (m, 4H), 3.41-3.34 (m, 2H), 3.28-3.07 (m, 4H), 2.90-2.82 (m, 1H), 2.04-1.95 (m, 2H), 1.94-1.85 (m, 1H), 1.83-1.68 (m, 3H); MS m/z 483.30 [M + H]$^+$. |
| 6 | 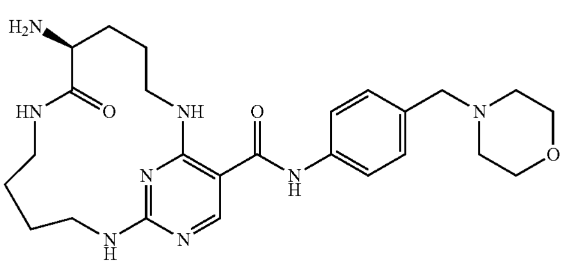 [SMILES: N[C@H]1CCCNc2nc(ncc2C(=O)Nc2ccc(CN3CCOCC3)cc2)NCCCCNC1=O] | UNC2341A | ++ | $^1$H NMR (400 MHz, CD$_3$OD) δ 8.45 (s, 1H), 7.81-7.75 (m, 2H), 7.53-7.48 (m, 2H), 4.34 (s, 2H), 4.08-3.98 (m, 2H), 3.92-3.85 (m, 1H), 3.80-3.66 (m, 3H), 3.61-3.52 (m, 1H), 3.47-3.32 (m, 4H), 3.27-3.11 (m, 3H), 2.99-2.96 (m, 1H), 2.95-2.88 (m, 1H), 1.96-1.86 (m, 3H), 1.86-1.75 (m, 2H), 1.72-1.61 (m, 2H), 1.48-4.33 (m, 1H); MS m/z 497.30 [M + H]$^+$. |

Table 1 describes compounds prepared following procedures described in Example 4 (General Procedure D), using appropriate reagents.

| | Structure | Compound_ID | Mer IC$_{50}$ | Physical Data MS m/z (M + 1) or/and $^1$H NMR |
|---|---|---|---|---|
| 7 | 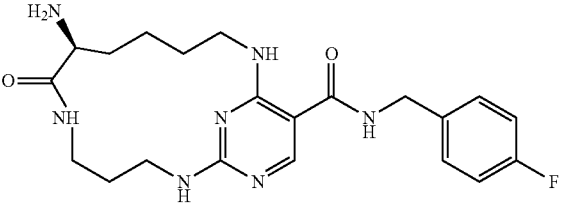 [SMILES: N[C@H]1CCCCNc2nc(ncc2C(=O)NCc2ccc(F)cc2)NCCCNC1=O] | UNC2481A | + | $^1$H NMR (400 MHz, CD$_3$OD) δ 8.17 (s, 1H), 7.37-7.30 (m, 2H), 7.06-7.00 (m, 2H), 4.44 (s, 2H), 3.89-3.78 (m, 2H), 3.77-3.72 (m, 2H), 3.69-3.62 (m, 1H), 3.49-3.33 (m, 3H), 3.02-2.93 (m, 2H), 1.98-1.76 (m, 5H), 1.73-1.62 (m, 3H), 1.60-1.49 (m, 2H); MS m/z 430.30 (M + H]$^+$. |
| 8 | 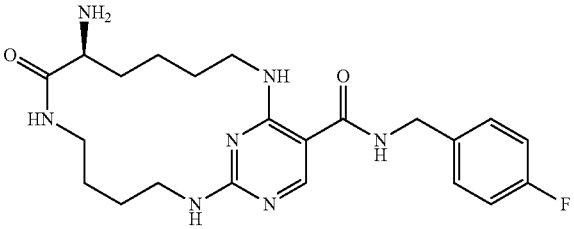 [SMILES: N[C@H]1CCCCNc2nc(ncc2C(=O)NCc2ccc(F)cc2)NCCCCNC1=O] | UNC2483A | +++ | $^1$H NMR (400 MHz, CD$_3$OD) δ 8.17 (s, 1H), 7.37-7.30 (m, 2H), 7.08-6.99 (m, 2H), 4.45 (s, 2H), 3.91-3.80 (m, 2H), 3.79-3.71 (m, 1H), 3.59-3.51 (m, 1H), 3.48-3.39 (m, 2H), 3.22-3.13 (m, 1H), 2.89-2.80 (m, 1H), 1.94-1.76 (m, 3H), 1.75-1.27 (m, 10H); MS m/z 445.30 [M + M]$^+$. |
| 9 | 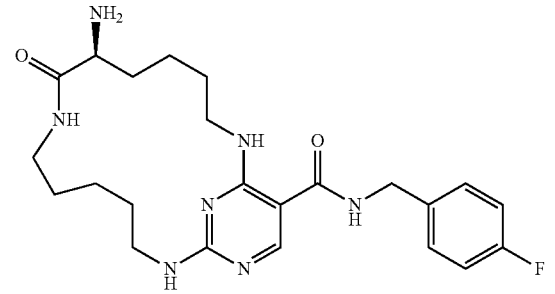 [SMILES: N[C@H]1CCCCNc2nc(ncc2C(=O)NCc2ccc(F)cc2)NCCCCCNC1=O] | UNC2484A | +++ | 1H NMR (400 MHz, CD$_3$OD) δ 8.17 (s, 1H), 7.36-7.30 (m, 2H), 7.08-6.99 (m, 2H), 4.45 (s, 2H), 3.81-3.74 (m, 1H), 3.73-3.66 (m, 1H), 3.65-3.59 (m, 2H), 3.53-3.45 (m, 2H), 2.99-2.94 (m, 1H), 2.87-2.82 (m, 1H), 1.90-1.81 (m, 2H), 1.75-1.54 (m, 6H), 1.50-1.31 (m, 5H); MS m/z 458.25 [M + H]$^+$. |
| 10 | 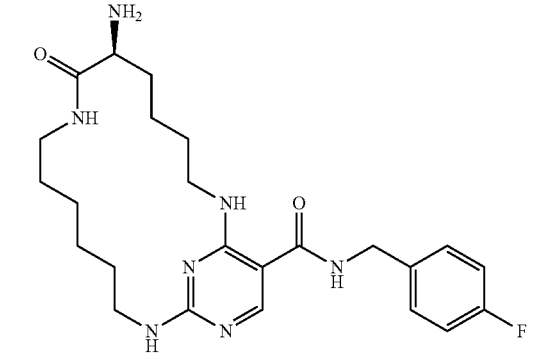 [SMILES: N[C@H]1CCCCNc2nc(ncc2C(=O)NCc2ccc(F)cc2)NCCCCCCNC1=O] | UNC2541A | ++++ | $^1$H NMR (400 MHz, CD$_3$OD) δ 8.18 (s, 1H), 7.36-7.29 (m, 2H), 7.07-6.98 (m, 2H), 4.44 (s, 2H), 3.84 (t, J = 5.6 Hz, 1H), 3.73-3.63 (m, 2H), 3.52-3.40 (m, 2H), 3.01-2.89 (m, 2H), 1.97-1.84 (m, 2H), 1.75-1.42 (m, 9H), 1.41-1.29 (m, 5H); MS m/z 472.30 [M + H]$^+$. |
| 11 | 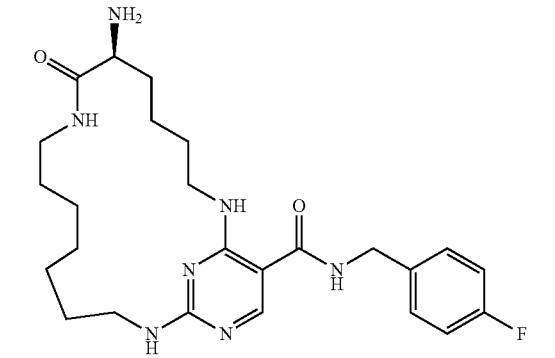 [SMILES: N[C@H]1CCCCNc2nc(ncc2C(=O)NCc2ccc(F)cc2)NCCCCCCCNC1=O] | UNC2486A | ++++ | $^1$H MMR (400 MHz, CD$_3$OD) δ 8.19 (s, 1H), 7.37-7.30 (m, 2H), 7.07-6.99 (m, 2H), 4.45 (s, 2H), 3.82-3.75 (m, 1H), 3.75- 3.63 (m, 2H), 3.61-3.54 (m, 1H), 3.48-3.41 (m, 1H), 3.37-3.30 (m, 1H), 2.89-2.80 (m, 1H), 1.93-1.82 (m, 2H), 1.76-1.60 (m, 4H), 1.57-1.27 (m, 11H); MS m/z 486.30 [M + H]$^+$. |

Table 1 describes compounds prepared following procedures described in Example 4 (General Procedure D), using appropriate reagents.

| | Structure | Compound_ID | Mer IC$_{50}$ | Physical Data MS m/z (M + 1) or/and $^1$H NMR |
|---|---|---|---|---|
| 12 | 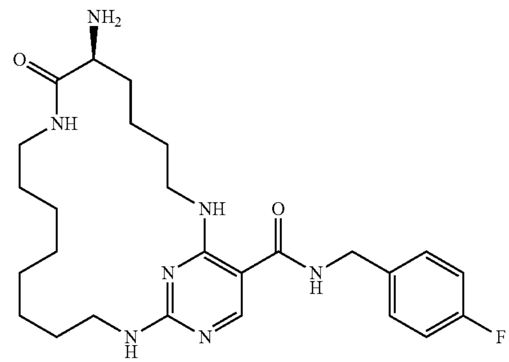 [SMILES: N[C@H]1CCCCNc2nc(ncc2C(=O)NCc2ccc(F)cc2)NCCCCCCCCNC1=O] | UNC2487A | ++++ | $^1$H NMR (400 MHz, CD$_3$OD) δ 8.06 (s, 1H), 7.26-7.21 (m, 2H), 6.98-6.90 (m, 2H), 5.28 (s, 2H), 4.39 (s, 2H), 3.39-3.34 (m, 2H), 3.31-3.23 (m, 3H), 3.20-3.11 (m, 1H), 1.68-1.56 (m, 4H), 1.56-1.50 (m, 2H), 1.48-1.38 (m, 2H), 1.34-1.19 (m, 10H); MS m/z 500.35 [M + H]$^+$. |
| 13 | 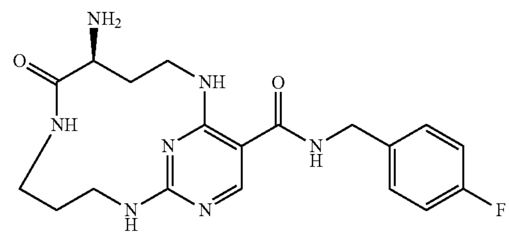 [SMILES: N[C@H]1CCNc2nc(ncc2C(=O)NCc2ccc(F)cc2)NCCCNC1=O] | UNC2573A | + | $^1$H NMR (400 MHz, CD$_3$OD) δ 8.22 (s, 1H), 7.37-7.29 (m, 2H), 7.06-6.98 (m, 2H), 4.45 (s, 2H), 3.95-3.89 (m, 1H), 3.85-3.75 (m, 1H), 3.70-3.59 (m, 2H), 3.53-3.40 (m, 2H), 2.87-2.77 (m, 1H), 2.36-2.23 (m, 1H), 2.18-2.08 (m, 1H), 2.06-1.95 (m, 1H), 1.72-1.59 (m, 1H); MS m/z 402.20 [M + H]$^+$. |
| 14 | 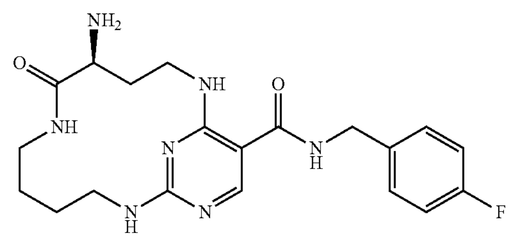 [SMILES: N[C@H]1CCNc2nc(ncc2C(=O)NCc2ccc(F)cc2)NCCCCNC1=O] | UNC2574A | ++ | $^1$H NMR (400 MHz, CD$_3$OD) δ 8.21 (s, 1H), 7.38-7.27 (m, 2H), 7.07-6.97 (m, 2H), 4.45 (s, 2H), 4.01-3.95 (m, 1H), 3.94-3.85 (m, 1H), 3.78-3.69 (m, 1H), 3.67-3.57 (m, 1H), 3.46-3.37 (m, 1H), 3.24-3.15 (m, 1H), 3.05-2.91 (m, 5H), 2.20-2.10 (m, 2H), 2.03-1.91 (m, 1H), 1.79-1.69 (m, 2H), 1.63-1.47 (m, 2H); MS m/z 416.25 [M + H]$^+$. |
| 15 | 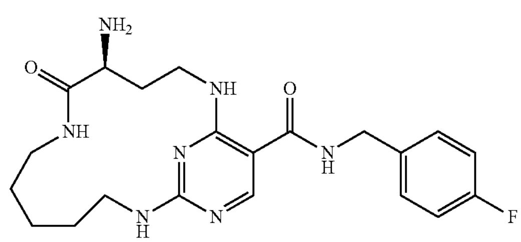 [SMILES: N[C@H]1CCNc2nc(ncc2C(=O)NCc2ccc(F)cc2)NCCCCCNC1=O] | UNC2575A | ++ | $^1$H NMR (400 MHz, CD$_3$OD) δ 8.23 (s, 1H), 7.37-7.29 (m, 2H), 7.07-6.98 (m, 2H), 4.45 (s, 2H), 3.92-3.74 (m, 3H), 3.63-3.52 (m, 2H), 3.26-3.21 (m, 1H), 2.96 (s, 1H), 2.89-2.82 (m, 1H), 2.21-2.13 (m, 2H), 1.74-1.59 (m, 3H), 1.58-1.43 (m, 3H); MS m/z 430.25 [M + H]$^+$. |
| 16 | 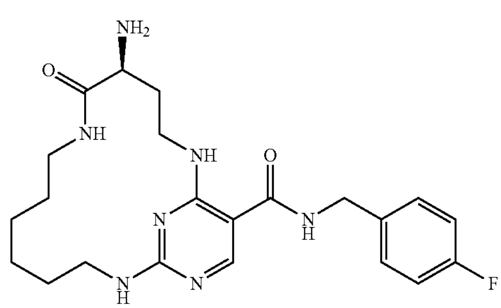 [SMILES: N[C@H]1CCNc2nc(ncc2C(=O)NCc2ccc(F)cc2)NCCCCCCNC1=O] | UNC2576A | ++ | $^1$H NMR (400 MHz, CD$_3$OD) δ 8.24 (s, 1H), 7.38-7.29 (m, 2H), 7.07-6.98 (m, 2H), 4.45 (s, 2H), 3.92-3.73 (m, 2H), 3.69-3.59 (m, 2H), 3.52 (ddd, J = 20.6, 13.5, 6.4 Hz, 2H), 3.24-3.10 (m, 2H), 2.98-2.93 (m, 4H), 2.25-2.14 (m, 2H), 1.68-1.59 (m, 3H), 1.55-1.48 (m, 2H), 1.45-1.34 (m, 4H); MS m/z 444.30 [M + H]$^+$. |

Table 1 describes compounds prepared following procedures described in Example 4 (General Procedure D), using appropriate reagents.

| Structure | Compound_ID | Mer IC$_{50}$ | Physical Data MS m/z (M + 1) or/and $^1$H NMR |
|---|---|---|---|
| 17 | UNC2577A | ++ | $^1$H NMR (400 MHz, CD$_3$OD) δ 8.24 (s, 1H, 7.40-7.28 (m, 2H), 7.08-6.97 (m, 2H), 4.45 (s, 2H), 3.88-3.80 (m, 1H), 3.78-3.69 (m, 1H), 3.68-3.53 (m, 3H), 2.93-2.83 (m, 1H), 2.39-2.28 (m, 1H), 2.16-2.04 (m, 1H), 1.71-3.26 (m, 11H); MS m/z 458.30 [M + H]$^+$. |
| 18 | UNC2578A | ++ | $^1$H NMR (400 MHz, CD$_3$OD) δ 8.25 (s, 1H), 7.38-7.29 (m, 2H), 7.07-6.99 (m, 2H), 4.46 (s, 2H), 3.87-3.66 (m, 4H), 3.51-3.43 (m, 1H), 2.91-2.84 (m, 1H), 2.45-2.33 (m, 1H), 2.11-2.03 (m, 1H), 1.67-1.53 (m, 3H), 1.51-1.13 (m, 10H); MS m/z 472.30 [M + H]$^+$. |
| 19 | UNC2741A | ++ | $^1$H NMR (400 MHz, cd$_3$od) δ 8.35 (s, 1H), 7.88 (t, J = 5.8 Hz, 1H), 7.38-7.31 (m, 2H), 7.09-7.01 (m, 2H), 4.46 (s, 2H), 3.64-3.55 (m, 2H), 3.44-3.36 (m, 2H), 3.28-3.23 (m, 2H), 2.20 (t, J = 6.7 Hz, 2H), 1.76-1.60 (m, 7H), 1.59-1.48 (m, 2H), 1.44-1.31 (m, 6H); MS m/z 457.30 [M + H]$^+$. |
| 20 | UNC2611A | ++++ | $^1$H NMR (400 MHz, cd$_3$od) δ 8.20 (s, 1H), 7.40-7.29 (m, 2H), 7.08-7.00 (m, 2H), 4.48-4.44 (m, 2H), 4.44-4.38 (m, 1H), 4.19-4.11 (m, 2H), 3.78-3.68 (m, 1H), 3.57-3.49 (m, 1H), 3.45-3.32 (m, 2H), 2.08-1.93 (m, 2H), 1.84-1.60 (m, 7H), 1.51-1.26 (m, 5H); MS m/z 473.30 [M + H]$^+$. |

(Note: Mer IC50: ++++ means <10 nM; +++ means between 10-100 nM, ++ means between 100 nM-1 μM; + means between 1-30 μM; — means inactive.)

Example 5

UNC2324A

General Procedure E

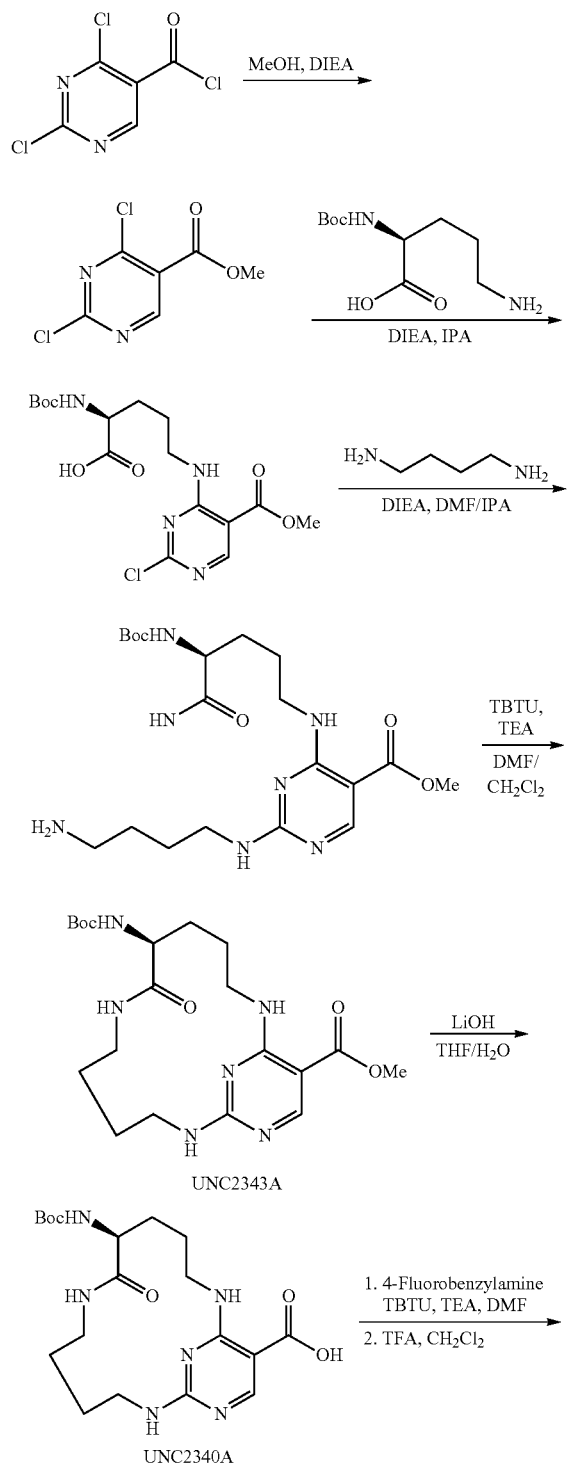

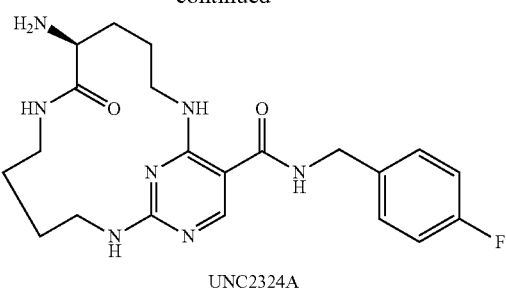

UNC2324A

UNC2343A

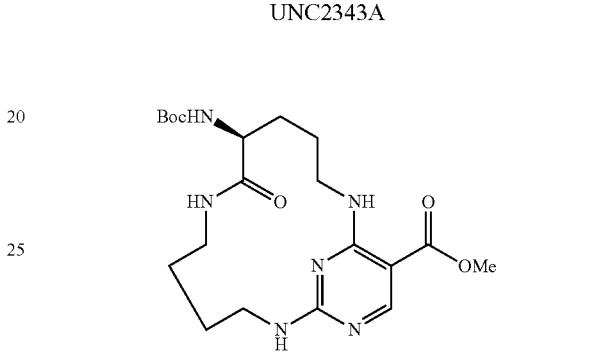

To a solution of 2,4-dichloropyrimidine-5-carbonyl chloride (500 mg, 2.38 mmol) in dichloromethane (30 mL) was added methanol (87.6 mg, 2.73 mmol) and diisopropylethylamine (369 mg, 2.86 mmol) at 0° C. The resulting mixture was stirred for at 0° C. 1 h. Then the solvent was removed. The residue (412 mg, 2.0 mmol) was dissolved in IPA (20 mL) followed by the addition of L-Ornithine (465 mg, 2.0 mmol) and N,N-diisopropylethylamine (388 mg, 3.0 mmol). The resulting mixture was stirred at 0° C. for 90 min, then dichloromethane (5.0 mL) was added. The resulting mixture was stirred at 0° C. for 1.0 h and at room temperature overnight. Solvent was removed and the residue (MS m/z 403.30 [M+H]$^+$) was dissolved in DMF (5.0 mL) and was added dropwise into a solution of 1,4-diaminobutane (1.68 g, 19.1 mmol) in DMF (1.0 mL) at room temperature. The resulting mixture was heated to 45° C. for 1 h. The solvent was removed and the residue was dissolved in ethyl acetate (35 mL) and washed with water (3×). The organic layer was dried (Na$_2$SO$_4$), filtered and concentrated. The residue was purified on HPLC to provide (S)-5-((2-((4-aminobutyl)amino)-5-(methoxycarbonyl)pyrimidin-4-yl)amino)-2-((tert-butoxycarbonyl)amino)pentanoic acid as a semisolid (MS m/z 455.30 [M+H]$^+$). The semisolid (595 mg, 1.31 mmol) was dissolved in DMF (150 mL), then TBTU (546.4 mg, 1.70 mmol) and DIEA (508 mg, 3.93 mmol) were added sequentially. The resulting mixture was stirred at room temperature overnight. The solvent was removed. The residue was dissolved in ethyl acetate and washed with water (3×). The organic layer was dried (Na$_2$SO$_4$), filtered and concentrated. The residue was purified on HPLC to provide the totle compound (UNC2343A). $^1$H NMR (400 MHz, CD$_3$OD) δ 8.42 (s, 1H), 4.08-3.99 (m, 1H), 3.90-3.84 (m, 3H), 3.59-3.47 (m, 2H), 3.46-3.31 (m, 2H), 3.28-3.21 (m, 1H), 3.09-2.95 (m, 1H), 1.90-1.52 (m, 8H), 1.51-1.32 (m, 9H); MS m/z 437.30 [M+H]$^+$.

35
UNC2340A

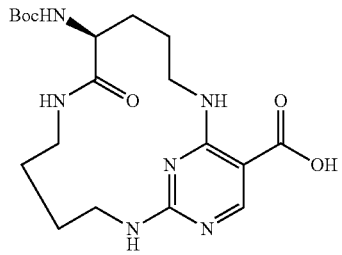 [SMILES: CC(C)(C)OC(=O)N[C@H]1CCCNc2nc(ncc2C(=O)O)NCCCCNC1=O]

Lithium hydroxide (200 mg, 8.3 mmol) was added to a solution of UNC2343A (724 mg, 1.66 mmol) in a mixture of THF and H$_2$O (20 mL, 3:2, v/v). The resulting mixture was heated at 75° C. overnight. Then the reaction mixture was acidified to pH 4, then extracted with a mixture of CH$_2$Cl$_2$ and IPA (3:1, v/v) to give the title compound (UNC2340A) (406 mg, 58%). $^1$H NMR (400 MHz, CD$_3$OD) δ 8.36 (s, 1H), 8.11 (s, 1H), 4.12-4.02 (m, 1H), 3.61-3.47 (m, 2H), 3.34 (s, 1H), 3.28-3.17 (m, 1H), 3.06-2.93 (m, 1H), 2.90-2.84 (m, 1H), 1.89-1.52 (m, 7H), 1.42 (s, 9H); MS m/z 423.25 [M+H]$^+$.

36
UNC2324A

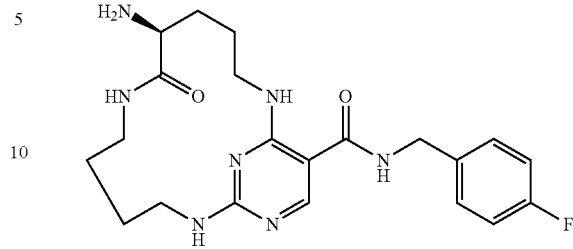

4-Fluorobenzylamine (65.1 mg, 0.5 mmol), TBTU (128.2 mg, 0.4 mmol) and triethylamine (68 mg, 0.67 mmol) were added to a solution of UNC2340A (40 mg, 0.095 mmol) in anhydrous DMF (20 mL) at room temperature. The resulting mixture was stirred for 2 h, then solvent was removed, the residue was dissolved in CH$_2$Cl$_2$ (30 mL) and washed with water (2×). TFA (1.0 mL) was then added and stirred at room temperature for 2.0 h, condensed and purified on HPLC to provide the title compound (UNC2324A) (26 mg, 52%). $^1$H NMR (400 MHz, CD$_3$OD) δ 8.19 (s, 1H), 7.37-7.26 (m, 2H), 7.07-6.96 (m, 2H), 4.44 (s, 2H), 3.88-3.82 (m, 1H), 3.77-3.68 (m, 1H), 3.58-3.47 (m, 2H), 3.43-3.35 (m, 1H), 3.26-3.13 (m, 2H), 2.98-2.93 (m, 2H), 2.92-2.84 (m, 1H), 1.92-1.81 (m, 3H), 1.81-1.53 (m, 5H), 1.44-1.29 (m, 1H); MS m/z 430.20 [M+H]$^+$.

Table 2 describes compounds prepared following procedures described in Example 5 (General Procedure E), using appropriate reagents.

| | Structure | Compound_ID | Mer IC$_{50}$ | Physical Data MS M/z (M + 1) or/and $^1$H NMR |
|---|---|---|---|---|
| 1 | ![structure] | UNC2589A | ++ | $^1$H NMR (400 MHz, CD$_3$OD) δ 8.21 (s, 1H), 7.39-7.35 (m, 4H), 4.50-4.47 (m, 2H), 3.97-3.91 (m, 3H), 3.87-3.83 (m, 1H), 3.40-3.33 (m, 5H), 3.09-3.01 (m, 4H), 2.87 (s, 4H), 1.93-1.82 (m, 4H), 1.79-1.70 (m, 2H), 1.69-1.57 (m, 3H), 1.44-1.30 (m, 2H); MS m/z 524.40 [M + H]$^+$. |
| 2 | ![structure] | UNC2615A | ++++ | $^1$H NMR (400 MHz, CD$_3$OD) δ 8.92 (s, 1H), 8.79 (d, J = 5.5 Hz, 1H), 8.67 (d, J = 8.0 Hz, 1H), 8.43 (s, 1H), 8.08 (dd, J = 7.8, 5.9 Hz, 1H), 4.71 (s, 2H), 3.92 (t, J = 5.3 Hz, 1H), 3.76-3.60 (m, 2H), 3.58-3.36 (m, 2H), 3.38-3.22 (m, 1H), 3.03-2.89 (m, 1H), 2.05-1.84 (m, 2H), 1.82-1.52 (m, 6H), 1.52-1.28 (m, 6H); MS (ESI): 455.4 [M + H]$^+$. |

-continued

Table 2 describes compounds prepared following procedures described in Example 5 (General Procedure E), using appropriate reagents.

| | Structure | Compound_ID | Mer IC$_{50}$ | Physical Data MS M/z (M + 1) or/and $^1$H NMR |
|---|---|---|---|---|
| 3 | 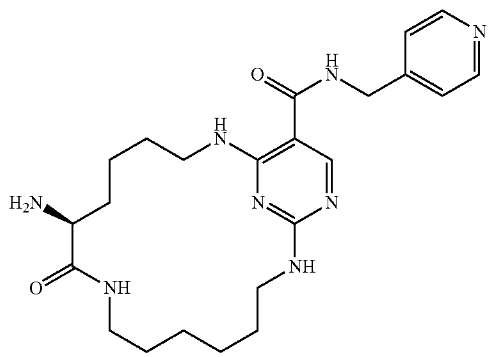 [SMILES: N[C@H]1CCCCNc2nc(ncc2C(=O)NCc2ccncc2)NCCCCCCNC1=O] | UNC2616A | ++++ | $^1$H NMR (400 MHz, CD$_3$OD) δ 8.81 (d, J = 6.0 Hz, 2H), 8.49 (s, 1H), 8.10 (d, J = 6.1 Hz, 2H), 4.80 (s, 2H), 3.92 (t, J = 5.3 Hz, 1H), 3.82-3.60 (m, 2H), 3.59-3.38 (m, 2H), 3.37-3.31 (m, 1H), 3.05-2.91 (m, 1H), 2.04-1.83 (m, 2H), 1.82-1.54 (m, 6H), 1.54-1.23 (m, 6H); MS (ESI): 455.3 [M + H]$^+$. |
| 4 | 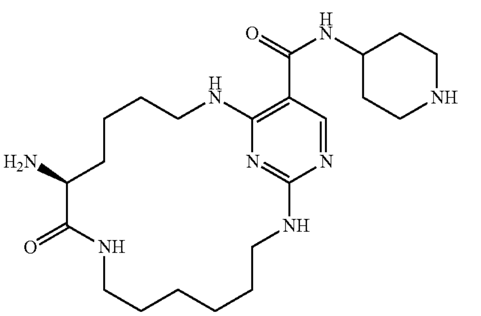 [SMILES: N[C@H]1CCCCNc2nc(ncc2C(=O)NC2CCNCC2)NCCCCCCNC1=O] | UNC2625A | ++++ | $^1$H NMR (400 MHz, CD$_3$OD) δ 8.36 (s, 1H), 4.20-4.03 (m, 1H), 3.91 (t, J = 5.3 Hz, 1H), 3.82-3.61 (m, 2H), 3.60-3.39 (m, 4H), 3.37-3.21 (m, 1H), 3.20-3.04 (m, 2H), 3.04-2.88 (m, 1H), 2.24-2.07 (m, 2H), 2.04-1.81 (m, 4H), 1.81-1.23 (m, 12H); MS (ESI): 447.4 [M + H]$^+$. |
| 5 | 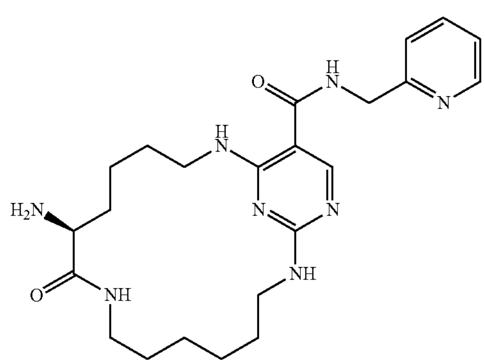 [SMILES: N[C@H]1CCCCNc2nc(ncc2C(=O)NCc2ccccn2)NCCCCCCNC1=O] | UNC2702A | +++ | $^1$H NMR (400 MHz, CD$_3$OD) δ 8.78 (d, J = 5.4 Hz, 1H), 8.59 (t, J = 7.6 Hz, 1H), 8.50 (s, 1H), 8.11 (d, J = 8.0 Hz, 1H), 7.99 (t, J = 8.0 Hz, 1H), 4.86 (s, 2H), 3.90 (t, J = 5.3 Hz, 1H), 3.77-3.61 (m, 2H), 3.60-3.38 (m, 2H), 3.35-3.25 (m, 1H), 2.95 (dt, J = 13.2, 4.5 Hz, 1H), 2.02-1.83 (m, 2H), 1.82-1.28 (m, 12H); MS (ESI): 455.4 [M + H]$^+$. |
| 6 | 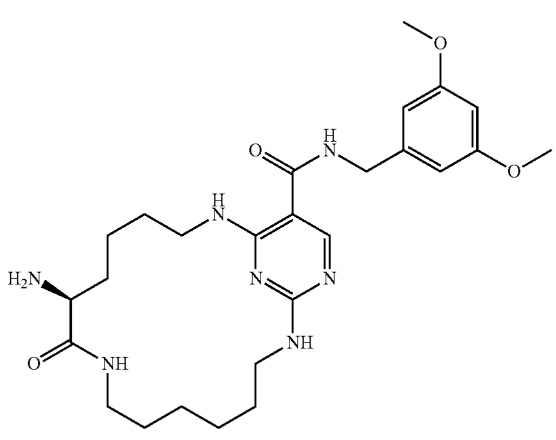 [SMILES: COc1cc(CNC(=O)c2cnc3nc2NCCCC[C@H](N)C(=O)NCCCCCCN3)cc(OC)c1] | UNC2626A | +++ | $^1$H NMR (400 MHz, CD$_3$OD) δ 8.16 (s, 1H), 7.16 (d, J = 8.3 Hz, 1H), 6.53 (d, J = 2.3 Hz, 1H), 6.46 (dd, J = 8.3, 2.4 Hz, 1H), 4.40 (s, 2H), 3.90 (t, J = 5.5 Hz, 1H), 3.83 (s, 3H), 3.77 (s, 3H), 3.73-3.63 (m, 1H), 3.55-3.39 (m, 2H), 2.97 (s, 1H), 2.03-1.83 (m, 2H), 1.77-1.31 (m, 13H); MS (ESI): 514.3 [M + H]$^+$. |

-continued

Table 2 describes compounds prepared following procedures described in Example 5
(General Procedure E), using appropriate reagents.

| | Structure | Compound_ID | Mer IC$_{50}$ | Physical Data MS M/z (M + 1) or/and $^1$H NMR |
|---|---|---|---|---|
| 7 | 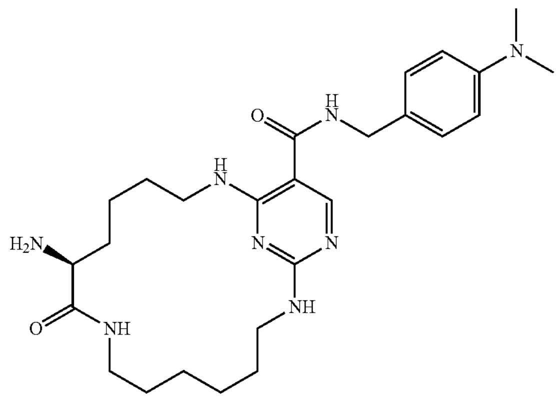 [SMILES: CN(C)c1ccc(CNC(=O)c2cnc3nc2NCCCC[C@H](N)C(=O)NCCCCCCN3)cc1] | UNC2701A | ++++ | $^1$H NMR (400 MHz, CD$_3$OD) δ 8.31 (s, 1H), 7.60 (dd, J = 23.0, 8.5 Hz, 4H), 4.54 (s, 2H), 3.90 (t, J = 5.4 Hz, 1H), 3.78-3.61 (m, 2H), 3.61-3.37 (m, 2H), 3.35-3.31 (m, 1H), 3.27 (s, 6H), 2.99-2.87 (m, 1H), 2.03-1.85 (m, 2H), 1.81-1.55 (m, 6H), 1.55-1.25 (m, 6H); MS (ESI): 497.4 [M + H]$^+$. |
| 8 | 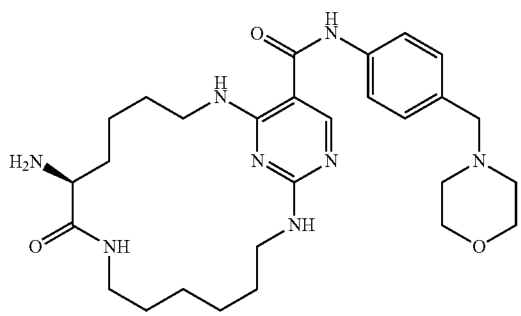 [SMILES: N[C@H]1CCCCNc2nc(ncc2C(=O)Nc2ccc(CN3CCOCC3)cc2)NCCCCCCNC1=O] | UNC2703A | ++++ | $^1$H NMR (400 MHz, D$_2$O) δ 8.28 (s, 1H), 7.59 (dd, J = 21.0, 8.7 Hz, 4H), 4.41 (s, 2H), 4.23-4.08 (m, 2H), 4.03 (t, J = 5.7 Hz, 1H), 3.87-3.44 (m, 8H), 3.38-3.23 (m, 3H), 3.09-3.01 (m, 1H), 2.03-1.90 (m, 2H), 1.83-1.55 (m, 6H), 1.53-1.27 (m, 6H); MS (ESI): 539.4 [M + H]$^+$. |
| 9 | 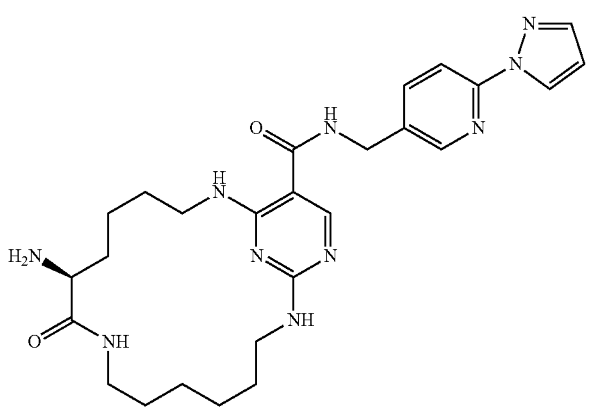 [SMILES: N[C@H]1CCCCNc2nc(ncc2C(=O)NCc2ccc(-n3cccn3)nc2)NCCCCCCNC1=O] | UNC2709A | ++++ | $^1$H NMR (400 MHz, CD$_3$OD) δ 8.57 (d, J = 2.5 Hz, 1H), 8.43 (d, J = 1.4 Hz, 1H), 8.23 (s, 1H), 7.99-7.85 (m, 2H), 7.75 (d, J = 1.2 Hz, 1H), 6.53 (dd, J = 2.5, 1.8 Hz, 1H), 4.54 (s, 2H), 3.86 (t, J = 5.5 Hz, 1H), 3.78-3.63 (m, 2H), 3.60-3.39 (m, 2H), 3.30-3.24 (m, 1H), 2.98-2.89 (m, 1H), 1.99-1.82 (m, 2H), 1.82-1.20 (m, 12H); MS (ESI): 521.4 [M + H]$^+$. |
| 10 | 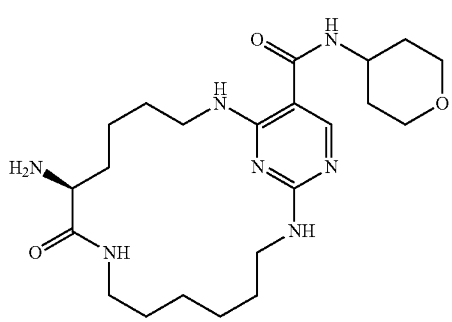 [SMILES: N[C@H]1CCCCNc2nc(ncc2C(=O)NC2CCOCC2)NCCCCCCNC1=O] | UNC2704A | ++++ | $^1$H NMR (400 MHz, D$_2$O) δ 8.06 (s, 1H), 4.13-3.95 (m, 4H), 3.89-3.74 (m, 2H), 3.72-3.56 (m, 4H), 3.55-3.39 (m, 2H), 3.36-3.23 (m, 1H), 3.05 (dt, J = 13.4, 4.7 Hz, 1H), 1.96 (dd, J = 13.5, 11.0 Hz, 4H), 1.72-1.60 (m, 6H), 1.53-1.24 (m, 6H); MS (ESI): 448.3 [M + H]$^+$. |

Table 2 describes compounds prepared following procedures described in Example 5 (General Procedure E), using appropriate reagents.

| | Structure | Compound_ID | Mer IC$_{50}$ | Physical Data MS M/z (M + 1) or/and $^1$H NMR |
|---|---|---|---|---|
| 11 | 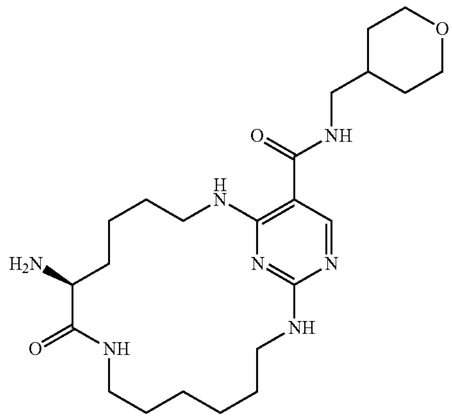 [SMILES: N[C@H]1CCCCNc2nc(ncc2C(=O)NCC2CCOCC2)NCCCCCCNC1=O] | UNC2705A | ++++ | $^1$H NMR (400 MHz, D$_2$O) δ 8.03 (s, 1H), 4.15-3.93 (m, 3H), 3.91-3.82 (m, 1H), 3.81-3.41 (m, 8H), 3.39-3.16 (m, 3H), 3.05 (dt, J = 13.5, 4.8 Hz, 1H), 2.03-1.80 (m, 3H), 1.79-1.49 (m, 7H), 1.49-1.30 (m, 6H); MS (ESI): 462.4 [M + H]$^+$. |
| 12 | 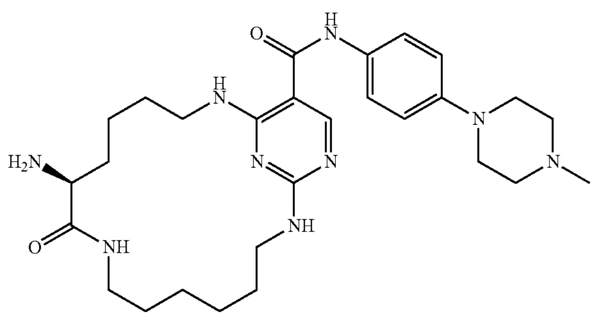 [SMILES: CN1CCN(c2ccc(NC(=O)c3cnc4nc3NCCCC[C@H](N)C(=O)NCCCCCCN4)cc2)CC1] | UNC2706B | ++++ | $^1$H NMR (400 MHz, D$_2$O) δ 8.23 (s, 1H), 7.46 (d, J = 8.8 Hz, 2H), 7.17 (d, J = 8.7 Hz, 2H), 4.03 (t, J = 5.4 Hz, 1H), 3.88 (d, J = 12.5 Hz, 2H), 3.78-3.43 (m, 6H), 3.25 (dd, J = 42.0, 11.7 Hz, 5H), 3.12-2.93 (m, 4H), 2.06-1.85 (m, 2H), 1.85-1.56 (m, 6H), 1.56-1.23 (m, 6H); MS (ESI): 538.4 [M + H]$^+$. |
| 13 | 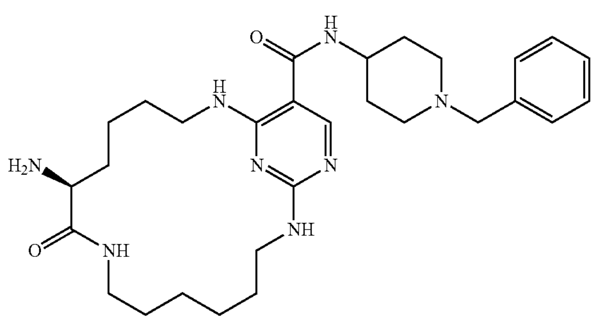 [SMILES: N[C@H]1CCCCNc2nc(ncc2C(=O)NC2CCN(Cc3ccccc3)CC2)NCCCCCCNC1=O] | UNC2834A | ++++ | $^1$H NMR (400 MHz, CD$_3$OD) δ 8.42-8.23 (m, 1H), 7.60 (s, 2H), 7.50 (s, 3H), 4.49-4.30 (m, 2H), 4.19-4.02 (m, 1H), 3.93 (s, 1H), 3.78-3.62 (m, 2H), 3.65-3.40 (m, 4H), 3.31-3.10 (m, 3H), 2.96 (d, J = 13.3 Hz, 1H), 2.26-1.83 (m, 6H), 1.82-1.56 (m, 6H), 1.57-1.26 (m, 6H); MS (ESI): 537.4 [M + H]$^+$. |
| 14 | 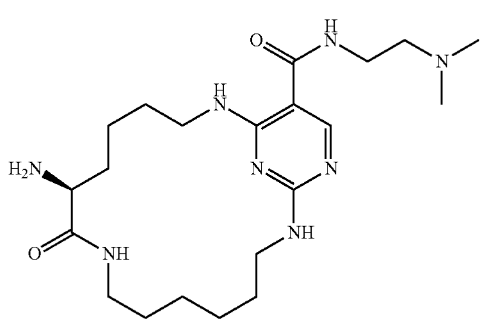 [SMILES: CN(C)CCNC(=O)c1cnc2nc1NCCCC[C@H](N)C(=O)NCCCCCCN2] | UNC2835A | ++ | $^1$H NMR (400 MHz, CD$_3$OD) δ 8.00 (s, 1H), 3.95-3.87 (m, 1H), 3.86-3.76 (m, 2H), 3.76-3.61 (m, 2.H), 3.59-3.39 (m, 2H), 3.31-3.24 (m, 3H), 3.15 (s, 3H), 3.01-2.90 (m, 1H), 2.75 (s, 3H), 2.04-1.85 (m, 2H), 1.86-1.55 (m, 6H), 1.53-1.28 (m, 6H); MS (ESI): 435.4 [M + H]$^+$. |

-continued

Table 2 describes compounds prepared following procedures described in Example 5 (General Procedure E), using appropriate reagents.

| Structure | Compound_ID | Mer IC$_{50}$ | Physical Data MS M/z (M + 1) or/and $^1$H NMR |
|---|---|---|---|
| 15 | UNC2836A | ++++ | $^1$H NMR (400 MHz, CD$_3$OD) δ 8.31 (s, 1H), 7.62 (dd, J = 35.5, 8.1 Hz, 4H), 4.54 (s, 2H), 4.19-4.01 (m, 4H), 3.91 (s, 1H), 3.79-3.60 (m, 6H), 3.59-3.41 (m, 2H), 3.30-3.25 (m, 1H), 3.02-2.87 (m, 1H), 2.04-1.84 (m, 2H), 1.84-1.55 (m, 6H), 1.51-1.28 (m, 6H); MS (ESI): 539.4 [M + H]$^+$. |
| 16 | UNC2837A | +++ | $^1$H NMR (400 MHz, CD$_3$OD) δ 8.53 (s, 1H), 8.41 (s, 1H), 8.24 (s, 1H), 7.89 (s, 2H), 7.72 (s, 1H), 6.50 (s, 1H), 4.52 (s, 2H), 4.08 (t, J = 4.7 Hz, 1H), 3.73-3.53 (m, 3H), 3.48-3.32 (m, 2H), 3.09-2.98 (m, 1H), 1.87-1.20 (m, 14H); MS (ESI): 544.3 [M + Na]$^+$. |
| 17 | UNC2910A | +++ | $^1$H NMR (400 MHz, CD$_3$OD) δ 8.35 (s, 1H), 7.65-7.55 (m, 2H), 7.52-7.43 (m, 3H), 6.33-6.12 (m, 2H), 5.86-5.68 (m, 2H), 4.34 (s, 2H), 4.26-3.88 (m, 5H), 3.76-3.42 (m, 5H), 3.16 (t, J = 12.4 Hz, 2H), 2.24-2.14 (m, 2H), 2.05-1.89 (m, 3H), 1.66-1.33 (m, 4H), 1.24-1.13 (m, 1H); MS (ESI): 533.4 [M + H]$^+$. |

-continued

Table 2 describes compounds prepared following procedures described in Example 5 (General Procedure E), using appropriate reagents.

| | Structure | Compound_ID | Mer IC$_{50}$ | Physical Data MS M/z (M + 1) or/and $^1$H NMR |
|---|---|---|---|---|
| 18 | 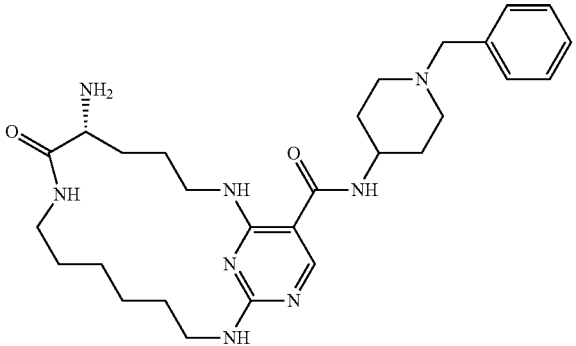 [SMILES: N[C@@H]1CCCNc2nc(ncc2C(=O)NC2CCN(Cc3ccccc3)CC2)NCCCCCCNC1=O] | UNC2967A | ++ | $^1$H NMR (400 MHz, CD$_3$OD) δ 8.48-8.37 (m, 1H), 8.21 (s, 1H), 7.54-7.40 (m, 4H), 4.43-4.21 (m, 2H), 4.05 (t, J = 11.7 Hz, 1H), 3.96 (s, 1H), 3.89-3.62 (m, 4H), 3.53 (d, J = 12.7 Hz, 2H), 3.43-3.34 (m, 2H), 3.12 (t, J = 12.4 Hz, 2H), 2.89-2.78 (m, 1H), 2.29-1.93 (m, 3H), 1.93-1.44 (m, 8H), 1.44-1.27 (m, 4H); MS (ESI): 523.4 [M + H]$^+$. |
| 19 | 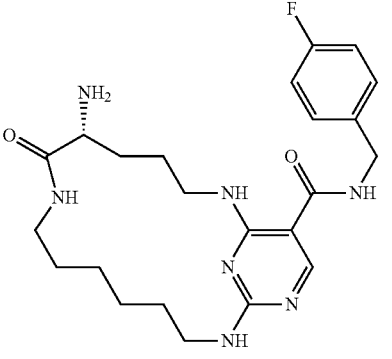 [SMILES: N[C@@H]1CCCNc2nc(ncc2C(=O)NCc2ccc(F)cc2)NCCCCCCNC1=O] | UNC2968A | ++ | $^1$H NMR (400 MHz, CD$_3$OD) δ 8.27 (s, 1H), 7.37 (dd, J = 8.5, 5.4 Hz, 2H), 7.05 (t, J = 8.7 Hz, 2H), 4.47 (s, 2H), 3.96-3.68 (m, 4H), 3.49-3.34 (m, 2H), 2.92-2.81 (m, 1H), 2.05-1.62 (m, 6H), 1.62-1.29 (m, 6H); MS (ESI): 458.3 [M + H]$^+$. |
| 20 | 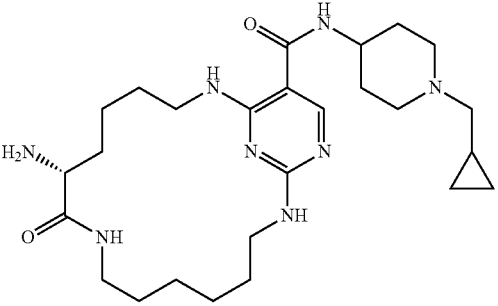 [SMILES: N[C@@H]1CCCCNc2nc(ncc2C(=O)NC2CCN(CC3CC3)CC2)NCCCCCCNC1=O] | UNC3038A | ++++ | $^1$H NMR (400 MHz, CD$_3$OD) δ 8.33 (s, 1H), 4.11 (s, 1H), 3.90 (t, J = 5.4 Hz, 1H), 3.79-3.65 (m, 3H), 3.62-3.38 (m, 3H), 3.29-3.23 (m, 1H), 3.22-2.84 (m, 5H), 2.33-1.83 (m, 6H), 1.78-1.57 (m, 6H), 1.53-1.30 (m, 6H), 1.20-1.10 (m, 1H), 0.86-0.69 (m, 2H), 0.54-0.37 (m, 2H); MS (ESI): 501.4 [M + H]$^+$. |
| 21 | 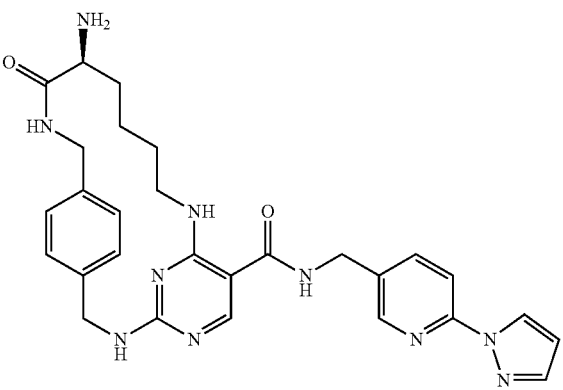 [SMILES: N[C@H]1CCCCNc2nc(ncc2C(=O)NCc2ccc(-n3cccn3)nc2)NCc2ccc(cc2)CNC1=O] | UNC2914A | +++ | $^1$H NMR (400 MHz, CD$_3$OD) δ 8.62 (d, J = 2.7 Hz, 1H), 8.48 (d, J = 2.0 Hz, 1H), 8.37 (s, 1H), 8.15 (dd, J = 8.6, 2.2 Hz, 1H), 8.03 (d, J = 8.6 Hz, 1H), 7.85 (d, J = 1.5 Hz, 1H), 7.35 (d, J = 8.1 Hz, 2H), 7.27 (d, J = 8.1 Hz, 2H), 6.62 (dd, J = 2.6, 1.8 Hz, 1H), 4.74 (d, J = 13.7 Hz, 1H), 4.60-4.48 (m, 4H), 3.95-3.83 (m, 2H), 3.76-3.55 (m, 1H), 3.43-3.32 (m, 1H), 3.28-3.15 (m, 1H), 1.86-1.72 (m, 2H), 1.31-1.10 (m, 2H), 1.03-0.88 (m, 1H), 0.56-0.43 (m, 1H). MS m/z 541.3 [M + H]$^+$. |

Table 2 describes compounds prepared following procedures described in Example 5 (General Procedure E), using appropriate reagents.
| | Structure | Compound_ID | Mer IC$_{50}$ | Physical Data MS M/z (M + 1) or/and $^1$H NMR |
|---|---|---|---|---|
| 22 | 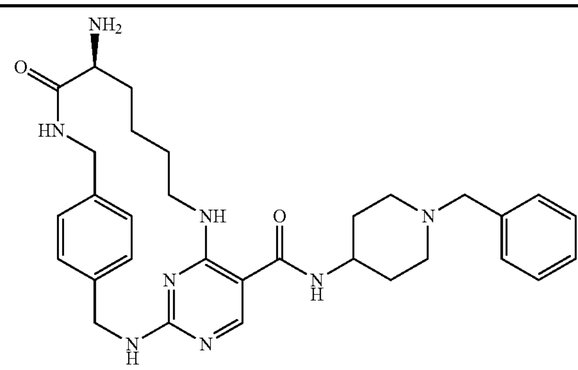 | UNC2916A | +++ | $^1$H NMR (400 MHz, CD$_3$OD) δ 8.35 (s, 1H), 7.62-7.53 (m, 2H), 7.53-7.46 (m, 3H), 7.40-7.33 (m, 2H), 7.31-7.23 (m, 2H), 4.81-4.71 (m, 1H), 4.61-4.49 (m, 2H), 4.46 (s, 1H), 4.33 (s, 2H), 4.12-3.99 (m, 1H), 3.94-3.82 (m, 2H), 3.77-3.67 (m, 1H), 3.62-3.47 (m, 2H), 3.45-3.33 (m, 2H), 3.26-3.08 (m, 4H), 2.23-2.11 (m, 2H), 2.01-1.87 (m, 2H), 1.77 (dd, J = 13.4, 7.9 Hz, 2H), 1.28-1.10 (m, 3H), 1.03-0.87 (m, 1H), 0.57-0.42 (m, 1H), MS m/z 557.35 [M + H]$^+$. |
Example 6
UNC3263A
General Procedure F
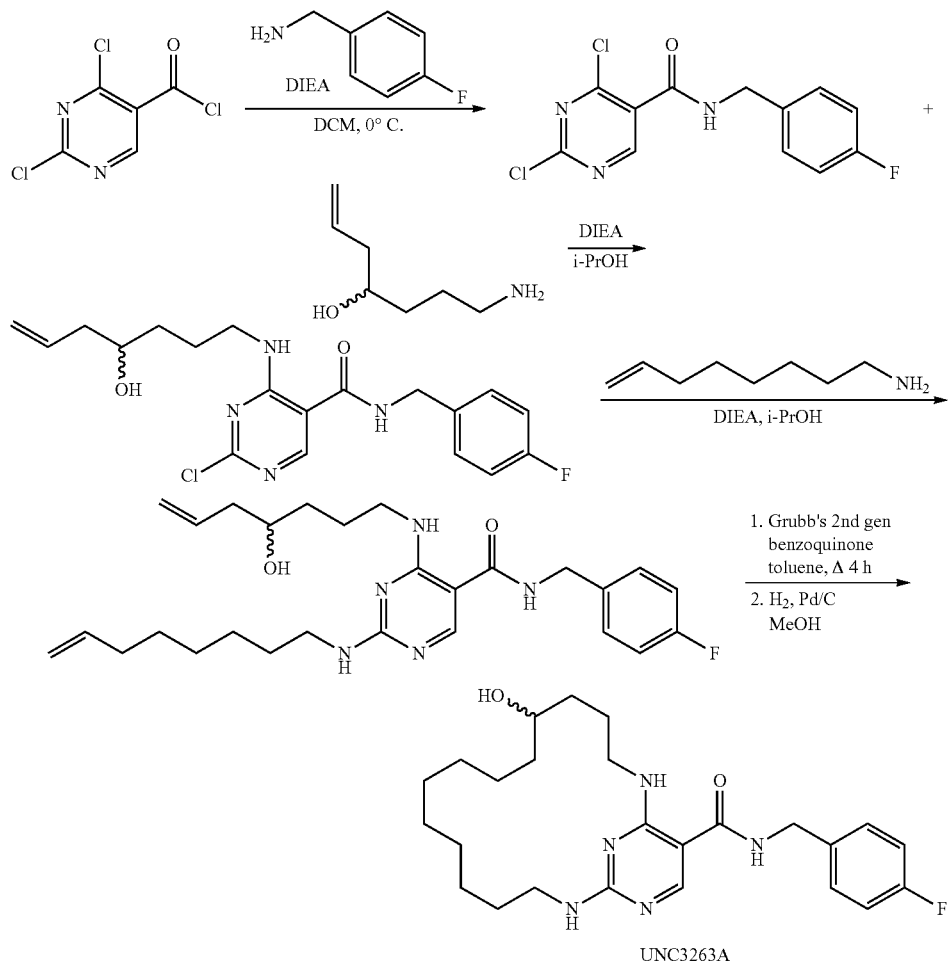

2,4-Dichloro-N-[(4-fluorophenyl)methyl]pyrimidine-5-carboxamide

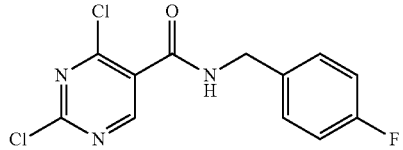 [SMILES: O=C(NCc1ccc(F)cc1)c1cnc(Cl)nc1Cl]

A solution of 2,4-dichloropyrimidine-5-carbonyl chloride (3.35 g, 15.8 mmol) in dichloromethane (53 mL) was added (4-fluorophenyl)methanamine (1.32 g, 10.56 mmol) and DIEA (3.7 mL, 21 mmol) at 0° C. The resulting mixture was stirred at 0° C. for 1 h, the solvent was removed, and the residue was purified by ISCO silica gel column to provide the title compound (1.97 g, 62%) as a yellow solid.

N-[(4-Fluorophenyl)methyl]-4-[(4-hydroxyhept-6-en-1-yl)amino]-2-[(oct-7-en-1-yl)amino]pyrimidine-5-carboxamide

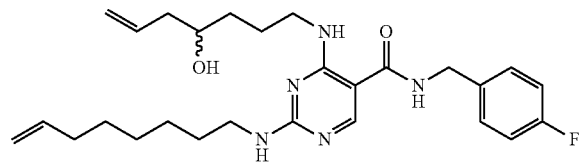 [SMILES: C=CCCCCCCNc1ncc(C(=O)NCc2ccc(F)cc2)c(NCCCC(O)CC=C)n1]

A solution of 2,4-dichloro-N-[(4-fluorophenyl)methyl]pyrimidine-5-carboxamide (97 mg, 0.325 mmol) in i-PrOH (5 mL) was added 7-aminohept-1-en-4-ol (42 mg, 0.325 mmol) and DIEA (85 µL, 0.488 mmol) at 0° C. The mixture was allowed to warm to room temperature and stirred overnight. To the reaction was added oct-7-en-1-amine (207 mg, 0.975 mmol) and DIEA (85 µL, 0.488 mmol). The reaction was heated at 70° C. for 6 h and the volatiles were removed under a reduced pressure. The residue was dissolved in $CH_2Cl_2$ (4.0 mL) and washed with $H_2O$ (2.0 mL). The $H_2O$ layer was extracted with $CH_2Cl_2$ (2×20 mL); the organic layers were combined, dried ($Na_2SO_4$), and the solvent was removed under a reduced pressure. The residue was purified by ISCO silica gel column to provide the title compound (39 mg, 25%) as a white solid. $^1$H NMR (400 MHz, $CDCl_3$) δ 8.70 (s, 1H), 8.09 (s, 1H), 7.29 (dd, J=8.7, 5.3 Hz, 2H), 7.07-6.98 (m, 2H), 6.08 (s, 1H), 5.90-5.71 (m, 2H), 5.18-5.04 (m, 1H), 5.03-4.89 (m, 2H), 4.51 (d, J=5.7 Hz, 2H), 3.70 (s, 1H), 3.49 (s, 2H), 3.38 (dt, J=9.7, 4.8 Hz, 2H), 2.35-2.12 (m, 2H), 1.80-1.68 (m, 2H), 1.59 (s, 9H), 1.44-1.31 (m, 5H).

N-[(4-Fluorophenyl)methyl]-6-hydroxy-2,16,1821-tetraazabicyclo[15.3.1]henicosa-1(20),17(21),18-triene-20-carboxamide (UNC3263A)

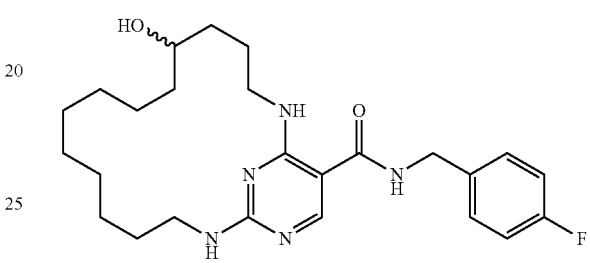

A solution of N-[(4-fluorophenyl)methyl]-4-[(4-hydroxyhept-6-en-1-yl)amino]-2-[(oct-7-en-1-yl)amino]pyrimidine-5-carboxamide (34 mg, 0.07 mmol) in toluene (35 mL) was added benzoquinone (1.5 mg, 0.014 mmol) and Grubb's $2^{nd}$ generation catalyst (6.0 mg, 0.007 mmol). The mixture was refluxed under Ar overnight. After which more catalyst was added (6.0 mg), and heated at reflux for 8 h. The volatiles were removed and the residue was purified by ISCO silica gel column to provide the RCM product as a crude brown solid. The residue was dissolved in MeOH (1.0 mL) and Pd/C (10 mg) was added. The mixture was stirred at room temperature under a hydrogen atmosphere for 24 h. The mixture was filtered through Celite and washed with MeOH then purified by HPLC to afford the title compound as a white solid (5.3 mg, 16%). $^1$H NMR (400 MHz, $CD_3OD$) δ 8.21 (s, 1H), 7.37 (dd, J=8.8, 5.4 Hz, 2H), 7.05 (t, J=8.8 Hz, 2H), 4.47 (s, 2H), 3.73-3.60 (m, 2H), 3.58-3.41 (m, 3H), 1.84-1.72 (m, 2H), 1.72-1.62 (m, 2H), 1.61-1.45 (m, 51H), 1.43-1.26 (m, 11H). MS m/z 458.3 [M+H]$^+$.

Table 3 describes compounds prepared following procedures described in Example 6 (General Procedure F), using appropriate reagents.

| | Structure | Compound_ID | Mer IC$_{50}$ | Physical Data MS m/z (M + 1) or/and $^1$H NMR |
|---|---|---|---|---|
| 1 | 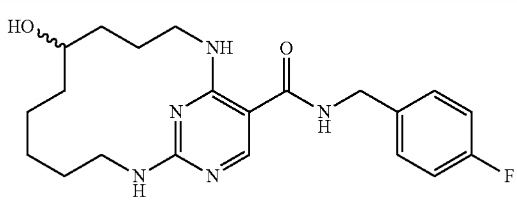 [SMILES: O=C(NCc1ccc(F)cc1)c1cnc2nc1NCCCC(O)CCCCCN2] | UNC3388A | +++ | $^1$H NMR (400 MHz, $CD_3OD$) δ 8.19 (s, 1H), 7.40-7.32 (m, 2H), 7.09-7.02 (m, 2H), 4.47 (s, 2H), 3.85-3.70 (m, 3H), 3.67-3.55 (m, 1H), 1.90-1.42 (m, 14H). MS m/z 402.3 [M + H]$^+$. |

Table 3 describes compounds prepared following procedures described in Example 6 (General Procedure F), using appropriate reagents.

| | Structure | Compound_ID | Mer IC$_{50}$ | Physical Data MS m/z (M + 1) or/and $^1$H NMR |
|---|---|---|---|---|
| 2 | 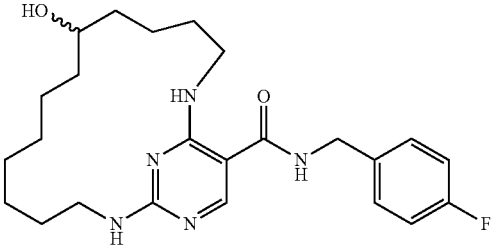 [SMILES: O=C(NCc1ccc(F)cc1)c1cnc2nc1NCCCCC(O)CCCCCCCN2] | UNC3429A | +++ | $^1$H NMR (400 MHz, CD$_3$OD) δ 8.19 (s, 1H), 7.37 (dd, J = 8.7, 5.4 Hz, 2H), 7.06 (t, J = 8.8 Hz, 2H), 4.47 (s, 2H), 3.81-3.70 (m, 1H), 3.66-3.55 (m, 2H), 3.54-3.46 (m, 1H), 3.45-3.35 (m, 1H), 1.85-1.72 (m, 1H), 1.72-1.59 (m, 3H), 1.58-1.30 (m, 14H). MS m/z 444.3 [M + H]$^+$. |
| 3 | 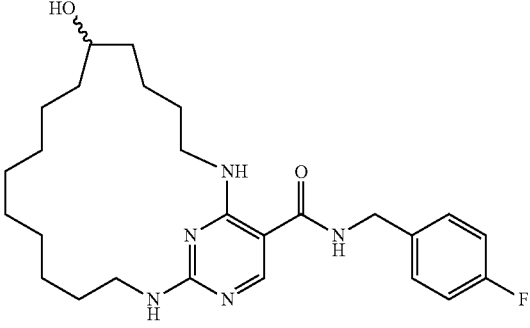 [SMILES: O=C(NCc1ccc(F)cc1)c1cnc2nc1NCCCCC(O)CCCCCCCCCN2] | UNC3431A | ++ | $^1$H NMR (400 MHz, CD$_3$OD) δ 8.20 (s, 1H), 7.37 (dd, J = 8.7, 5.4 Hz, 2H), 7.05 (t, J = 8.8 Hz, 2H), 4.47 (s, 2H), 3.59 (dd, J = 13.8, 6.7 Hz, 3H), 3.53-3.40 (m, 2H), 1.77-1.60 (m, 5H), 1.60-1.27 (m, 18H). MS m/z 472.3 [M + H]$^+$. |

Table 4 describes compounds can be prepared following procedures described in Example 6 (General Procedure F), using appropriate reagents.

| | Structure | Compound_ID | Mer IC$_{50}$ | Physical Data MS m/z (M + 1) or/and $^1$H NMR |
|---|---|---|---|---|
| 1 | 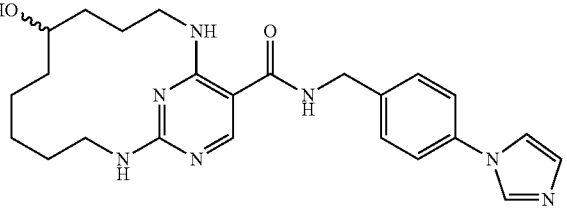 | | | |
| 2 | 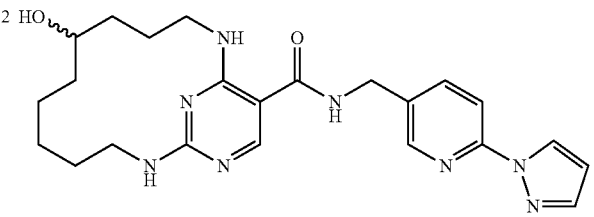 | | | |
| 3 | 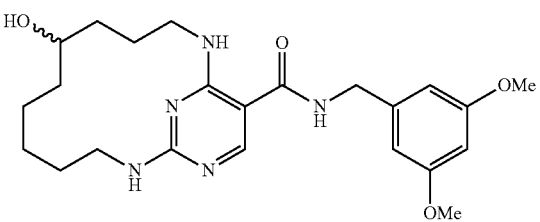 [SMILES: COc1cc(CNC(=O)c2cnc3nc2NCCCC(O)CCCCCN3)cc(OC)c1] | | | |

-continued
Table 4 describes compounds can be prepared following procedures described in Example 6 (General Procedure F), using appropriate reagents.
| | Structure | Compound_ID | Mer IC$_{50}$ | Physical Data MS m/z (M + 1) or/and $^1$H NMR |
|---|---|---|---|---|
| 4 | 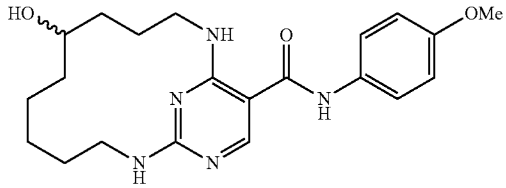 [SMILES: COc1ccc(NC(=O)c2cnc3nc2NCCCC(O)CCCCCN3)cc1] | | | |
| 5 | 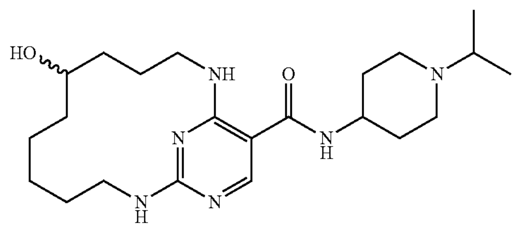 [SMILES: CC(C)N1CCC(NC(=O)c2cnc3nc2NCCCC(O)CCCCCN3)CC1] | | | |
Example 7
UNC3017A, UNC3018A & UNC3019A
General Procedure G
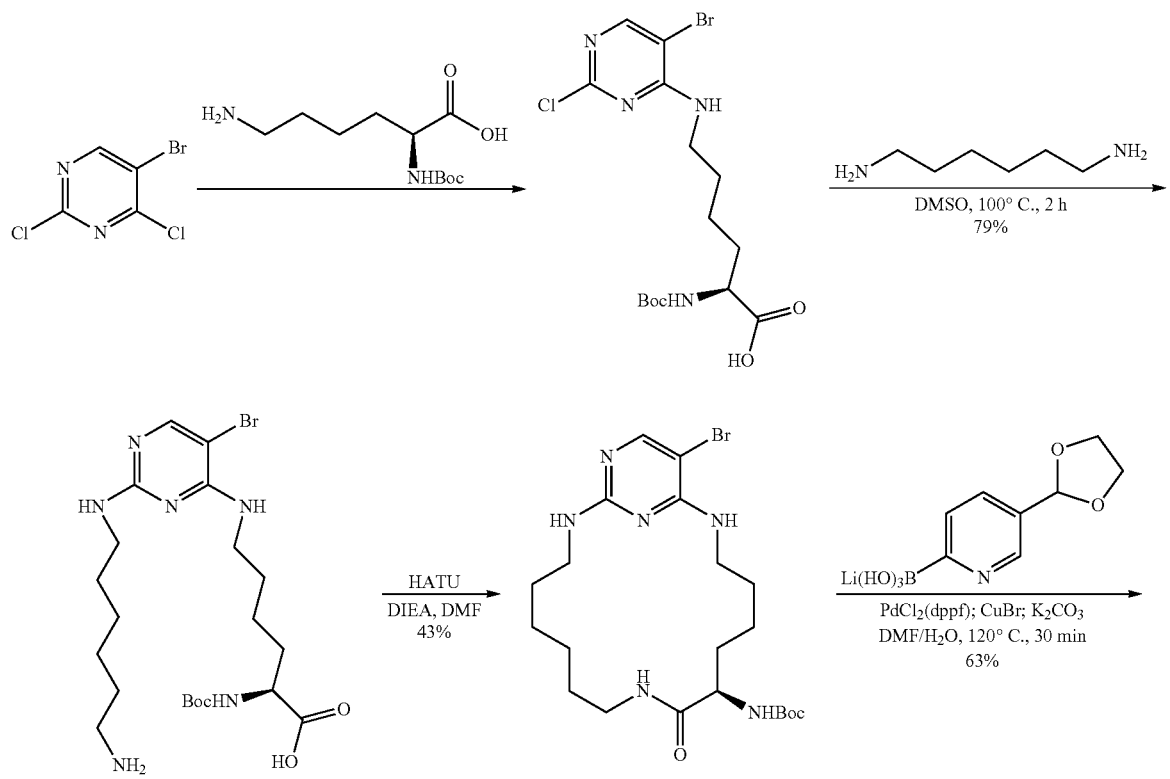

-continued
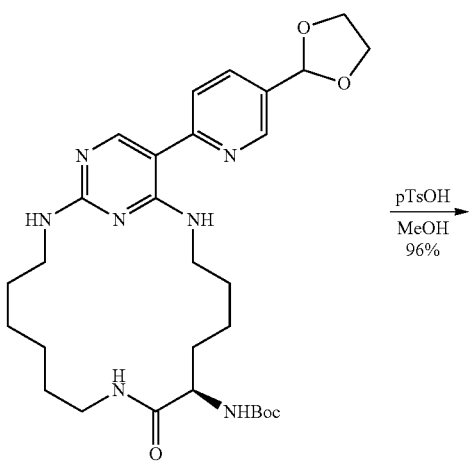
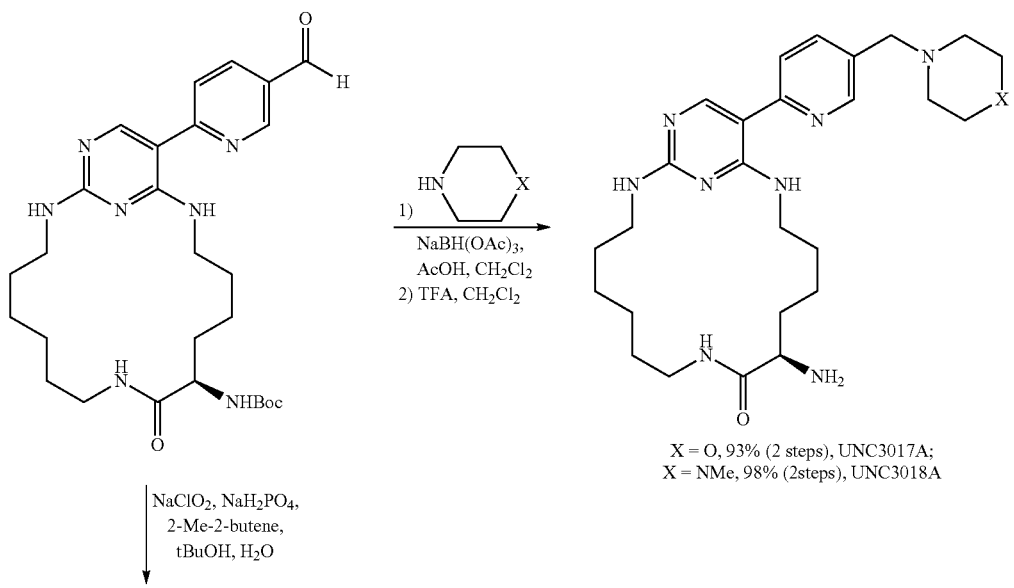
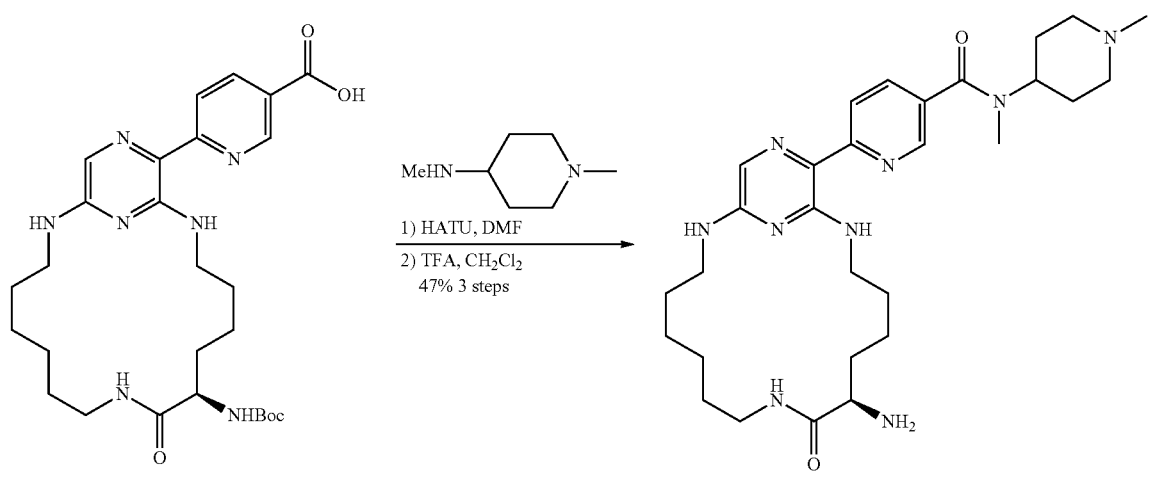

(S)-6-((2-((6-Aminohexyl)amino)-5-bromopyrimidin-4-yl)amino)-2-((tert-butoxycarbonyl)amino)hexanoic acid

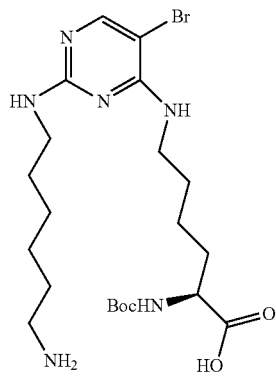 [SMILES: CC(C)(C)OC(=O)N[C@@H](CCCCNc1nc(NCCCCCCN)ncc1Br)C(=O)O]

A solution of (S)-6-amino-2-((tert-butoxycarbonyl)amino)hexanoic acid (0.042 g, 0.10 mmol) in DMSO was added hexane-1,6-diamine (0.046 g, 0.40 mmol). The resulting mixture was heated at 100° C. for 2 h. After cooled to room temperature, the solvent was removed under reduced pressure. The resulting residue was purified by reverse phase ISCO column to provide title compound (0.041 g, 79%). ¹H NMR (400 MHz, CD₃OD) δ 7.91 (s, 1H), 4.13-4.02 (m, 1H), 3.57 (t, J=12, 2H), 3.51-3.38 (bs, 2H), 2.94 (t, J=12, 2H), 1.92-1.80 (m, 1H), 1.75-1.62 (m, 7H), 1.57-1.36 (m, 15H); MS m/z 517.3 [M+H]⁺.

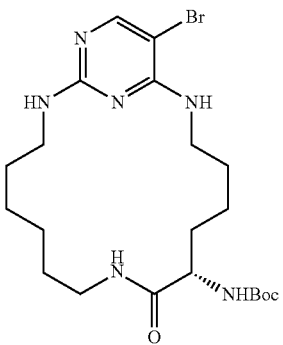 [SMILES: CC(C)(C)OC(=O)N[C@H]1CCCCNc2nc(ncc2Br)NCCCCCCNC1=O]

A solution of (S)-6-((2-((6-aminohexyl)amino)-5-bromopyrimidin-4-yl)amino)-2-((tert-butoxycarbonyl)amino)hexanoic acid (2.11 g, 4.08 mmol) and DIEA (1.78 mL, 10.19 mmol) in 20 mL DMF and a solution of HATU (2.01 g, 5.28 mmol) in 20 mL DMF were added to 200 mL of DMF in 16 h. After addition, the resulting mixture was stirred for 1 h. The solvent was removed under reduced pressure. The residue was purified by ISCO silica gel column to provide the desired bromide (0.87 g, 43%) contaminated with small amount of impurities.

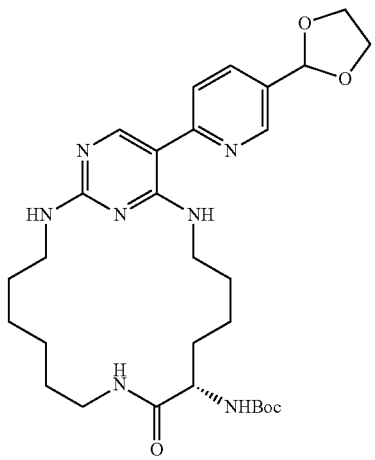 [SMILES: CC(C)(C)OC(=O)N[C@H]1CCCCNc2nc(ncc2-c2ccc(C3OCCO3)cn2)NCCCCCCNC1=O]

A solution of the bromide (0.66 g, 1.32 mmol) in DMF (6.6 mL) was added PdCl₂(dppf).CH₂Cl₂ (0.11 g, 0.13 mmol), CuBr (0.036 g, 0.26 mmol), K₂CO₃ (0.56 g, 9.96 mmol), (5-(1,3-dioxolan-2-yl)pyridin-2-yl)boronic acid lithium hydroxide (0.86 g, 9.96 mmol) and H₂O (1.7 mL) at room temperature. The resulting mixture was heated at 120° C. for 30 min under. After cooled to room temperature, the mixture was filtered over Celite. The solvents were removed under reduced pressure. The crude residue was purified by ISCO silica gel column to provide the desired acetal (0.76 g, 63%) contaminated with small amount of impurities. MS m/z 570.4 [M+H]⁺.

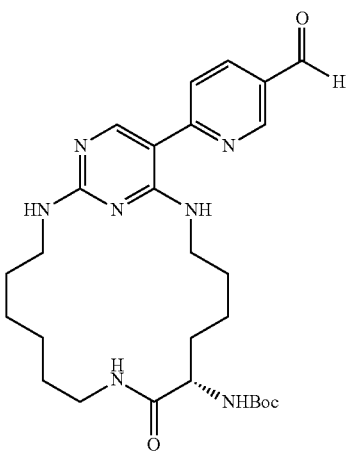 [SMILES: CC(C)(C)OC(=O)N[C@H]1CCCCNc2nc(ncc2-c2ccc(C=O)cn2)NCCCCCCNC1=O]

A solution of the acetal (0.47 g, 0.83 mmol) in acetone (10 mL) was added p-TsOH.H₂O (0.24 g, 1.25 mmol) and H₂O (2.0 mL). After stirring at room temperature for 16 h, the reaction mixture was quenched with a sat. aq solution of NaHCO₃ and extracted with EtOAc (3×). The combined organic layers were dried (Na₂SO₄) and concentrated. The resulting residue was purified by ISCO silica gel column to provide the desired aldehyde (0.42 g, 96%) contaminated with small amount of impurities. MS m/z 526.4 [M+H]⁺.

UNC3017A

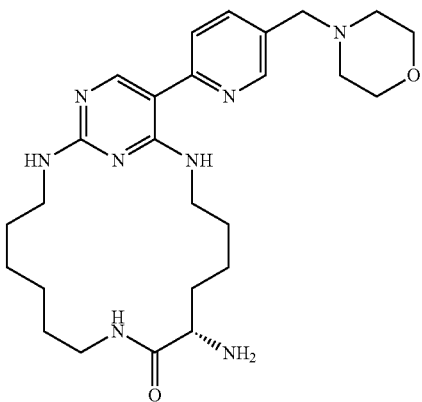 [SMILES: N[C@H]1CCCCNc2nc(ncc2-c2ccc(CN3CCOCC3)cn2)NCCCCCCNC1=O]

A solution of the aldehyde (0.53 g, 0.1 mmol) in CH$_2$Cl$_2$ (2.0 mL) was added morpholine (0.013 mL, 0.15 mmol) and acetic acid (0.04 mL). The resulting solution was stirred at room temperature for 2 h, then NaB(OAc)$_3$H (0.043 g, 0.15 mmol) was added. After stirred at room temperature for 16 h, the reaction was quenched with a sat. aq. solution of NaHCO$_3$ and extracted with EtOAc (3×). The combined organic layers were dried (Na$_2$SO$_4$) and concentrated. The residue was dissolved in a mixture of CH$_2$Cl$_2$ (2.0 mL) and TFA (1.0 mL). After stirred at room temperature for 2.0 h. the reaction was concentrated and the residue was purified by prep-HPLC to provide the desired product UNC3017A (0.046 g, 93%). $^1$H NMR (400 MHz, CD$_3$OD) δ 8.88 (s, 1H), 8.41 (s, 1H), 8.22 (d, J=8.4 Hz, 1H), 8.01 (d, J=8.4 Hz, 1H), 4.52 (s, 2H), 4.06 (d, J=10.7 Hz, 2H), 3.96-3.79 (m, 4H), 3.77-3.67 (m, 1H), 3.57 (td, J=12.2, 5.2 Hz, 2H), 3.45 (d, J=12.4 Hz, 2H), 3.39-3.23 (m, 3H), 3.02-2.93 (m, 1H), 1.96 (dd, J=10.2, 4.6 Hz, 2H), 1.86-1.51 (m, 7H), 1.42 (d, J=4.7 Hz, 5H); MS m/z 497.4 [M+H]$^+$.

UNC3018A

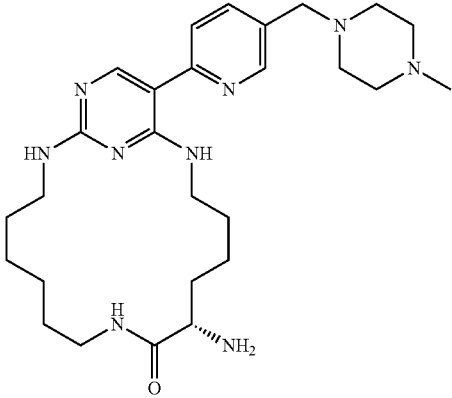 [SMILES: CN1CCN(Cc2ccc(-c3cnc4nc3NCCCC[C@H](N)C(=O)NCCCCCCN4)nc2)CC1]

A solution of the above aldehyde (0.53 g, 0.1 mmol) in CH$_2$C2 (2.0 mL) was added N-methylpiperazine (0.017 mL, 0.15 mmol) and acetic acid (0.04 mL). The resulting solution was stirred at room temperature for 2 h, then NaB(OAc)$_3$H (0.043 g, 0.15 mmol) was added. After stirred at room temperature for 16 h, the reaction was quenched with a sat. aq. solution of NaHCO$_3$ and extracted with EtOAc (3×). The combined organic layers were dried (Na$_2$SO$_4$) and concentrated. The residue was dissolved in a mixture of CH$_2$Cl$_2$ (2.0 mL) and TFA (1.0 mL). After stirred at room temperature for 2.0 h. the reaction was concentrated and the residue was purified by prep-HPLC to give the desired product UNC3018A (0.049 g, 98%). $^1$H NMR (400 MHz, CD$_3$OD) δ 8.91 (d, J=1.7 Hz, 1H), 8.40 (s, 1H), 8.27 (dd, J=8.5, 2.0 Hz, 1H), 8.01 (d, J=8.5 Hz, 1H), 4.61 (s, 2H), 3.91 (t, J=5.4 Hz, 1H), 3.88-3.61 (m, 10H), 3.61-3.51 (m, 2H), 3.39-3.34 (m, 1H), 3.02 (s, 3H), 3.00-2.92 (m, 1H), 2.03-1.89 (m, 2H), 1.87-1.50 (m, 7H), 1.48-1.35 (m, 5H); MS m/z 510.4 [M+H]$^+$.

UNC3019A

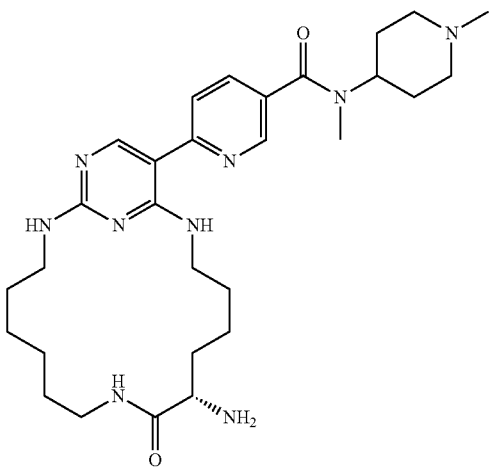 [SMILES: CN1CCC(N(C)C(=O)c2ccc(-c3cnc4nc3NCCCC[C@H](N)C(=O)NCCCCCCN4)nc2)CC1]

A mixture of aldehyde (0.053 g, 0.1 mmol) in 10 mL tBuOH was added NaClO$_2$ (0.034 g, 80%, 0.3 mmol), NaH$_2$PO$_4$ (0.041 g, 0.3 mmol), 2-Me-2-Butene (0.11 mL, 1 mmol) and 2 mL H$_2$O. After stirring 16 h at room temperature, the reaction was quenched with sat. aq. Na$_2$S$_2$O$_3$, acidified with diluted aq. HCl to pH 4 and extracted with EtOAc (3×). The combined organic layers were dried (Na$_2$SO$_4$) and concentrated. The residue was dissolved in 3 mL DMF. To this solution was added HATU (0.042 g, 0.11 mmol), followed by N,1-dimethylpiperidin-4-amine (0.014 g, 0.11 mmol). After stirring for 16 at room temperature, the reaction mixture was condensed under vacuum and purified by Prep-HPLC. The Boc protected intermediate was dissolved in 2 mL CH$_2$Cl$_2$ and 1 mL TFA and stirred for 2 h. After evaporating the solvents, the residue was purified by Prep-HPLC to provide the desired product UNC3019A (0.026 g, 47%). $^1$H NMR (400 MHz, CD$_3$OD) δ 8.70 (s, 1H), 8.41 (s, 1H), 8.02-7.93 (m, 2H), 3.92-3.50 (m, 8H), 3.39-3.33 (m, 1H), 3.23 (bs, 1H), 3.10-2.75 (m, 8H), 2.24 (dd, J=24.3, 11.4 Hz, 2H), 2.15-2.02 (m, 2H), 2.02-1.88 (m, 2H), 1.87-1.48 (m, 8H), 1.45-1.37 (m, 4H); MS m/z 552.4 [M+H]$^+$.

Example 8

UNC3588A

General Procedure H

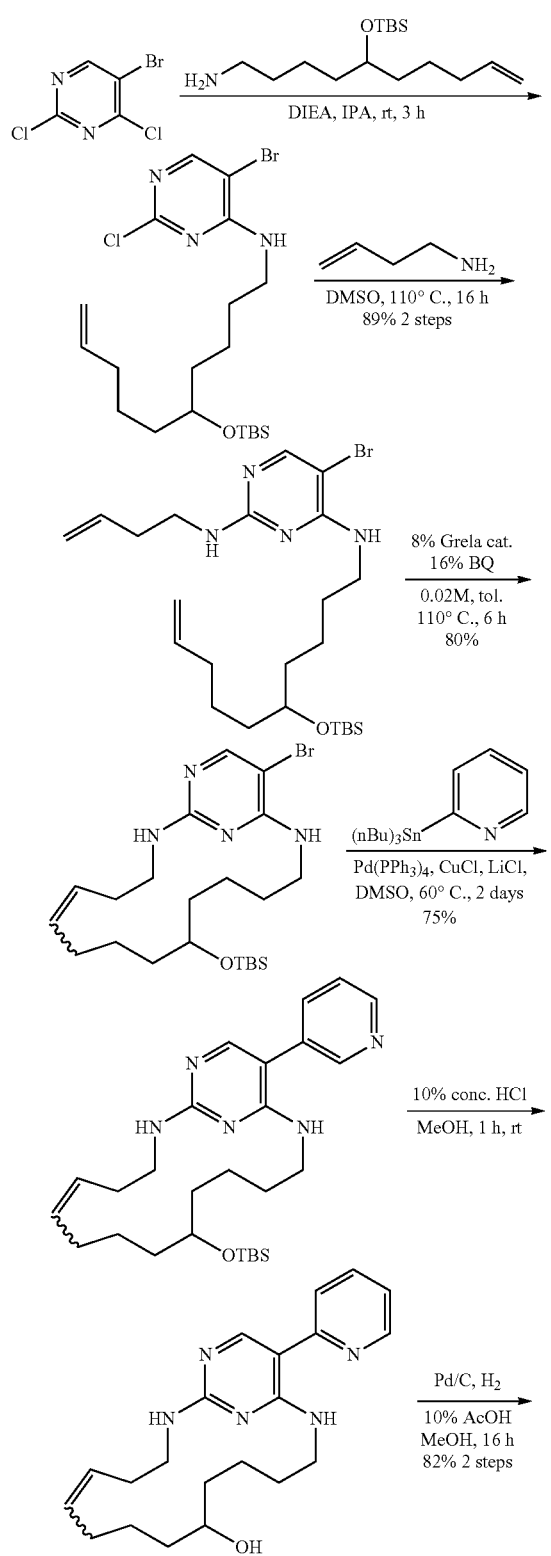

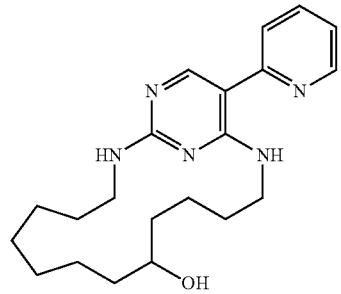 [SMILES: OC1CCCCCCCNc2ncc(-c3ccccn3)c(n2)NCCCC1]

5-Bromo-N2-(but-3-en-1-yl)-N4-(5-((tert-butyldimethylsilyl)oxy)dec-9-en-1-yl)pyrimidine-2,4-diamine

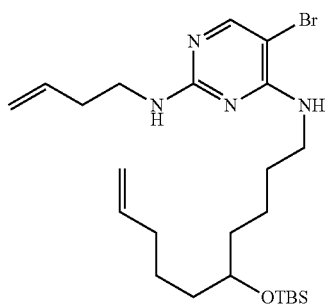 [SMILES: C=CCCCC(CCCCNc1nc(NCCC=C)ncc1Br)O[Si](C)(C)C(C)(C)C]

A solution of 5-bromo-2,4-dichloropyrimidine (0.29 g, 1.28 mmol) in isopropanol (3.0 mL) was added 5-((tert-butyldimethylsilyl)oxy)dec-9-en-1-amine (0.38 g, 1.34 mmol) and DIEA (0.27 mL, 1.54 mmol) at 0° C. The reaction solution was stirred at room temperature for 3 h. The solvent was removed under a reduced pressure to provide a yellow residue, which was dissolved in DMSO (5.0 mL). But-3-en-1-amine (0.47 mL, 5.12 mmol) was added. The resulting mixture was heated at 110° C. for 16 h, then diluted with Et$_2$O and quenched with brine. The aqueous layer was extracted with Et$_2$O (3×). The combined organic layers were dried (Na$_2$SO$_4$) and concentrated. The residue was purified by ISCO silica gel column to provide desired product (0.58 g, 89%). $^1$H NMR (400 MHz, CDCl$_3$) δ 7.85 (s, 1H), 5.91-5.72 (m, 2H), 5.18-4.91 (m, 5H), 4.85 (t, J=4.9 Hz, 1H), 3.65 (p, J=5.4 Hz, 1H), 3.47-3.37 (m, 4H), 2.34 (qt, J=6.8, 1.3 Hz, 2H), 2.03 (q, J=6.5 Hz, 2H), 1.64-1.53 (m, 2H), 1.51-1.33 (m, 8H), 0.88 (s, 9H), 0.04 (s, 3H), 0.03 (s, 3H); MS m/z 511.3 [M+H]$^+$.

UNC3588A

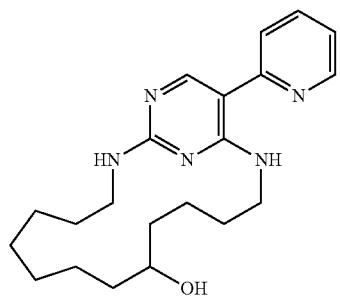 [SMILES: OC1CCCCCCCNc2ncc(-c3ccccn3)c(n2)NCCCC1]

A solution of 5-bromo-N²-(but-3-en-1-yl)-N⁴-(5-((tert-butyldimethylsilyl)oxy)dec-9-en-1-yl)pyrimidine-2,4-diamine (0.26 g, 0.50 mmol) and benzoquinone (0.009 g, 0.08 mmol) in toluene (20 mL) was added Grela's catalyst (0.027 g, 0.04 mmol) in toluene (5.0 mL) over 1.0 h at 110° C. The resulting dark brown solution was heated at 110° C. for another hour. After cooled to 60° C., 2-mercaptonicotinic acid (0.39 g, 2.5 mmol) was added and stirred at 60° C. for 2 h. After cooled to room temperature, the reaction mixture was filtered over Celite and washed with $CH_2Cl_2$. The filtrate was concentrated and the residue was purified by ISCO silica gel column to provide the macrocyclic intermediate as a mixture of E and Z olefin isomers (0.19 g, 80%). MS m/z 483.3 [M+H]⁺.

A schlenk flask containing LiCl (0.028 g, 0.66 mmol) and stir bar was flame dried. After cooled to room temperature, CuCl (0.054 g, 0.55 mmol) and $Pd(PPh_3)_4$ (0.013 g, 0.011 mmol) was added. The reaction mixture was vacuumed and refilled with argon (4×). The intermediate from previous step (0.054 g, 0.11 mmol) in DMSO (4.0 mL), and $Bu_3SnPy$ (0.049 g, 0.13 mmol) were added under argon. The resulting reaction mixture was freeze-thawed under argon (4×). The mixture was heated at 60° C. for 2 d, then diluted with EtOAc, quenched with brine and a saturated aq. solution of $NaHCO_3$. The organic layer was washed with a sat. aq solution of $NaHCO_3$ (3×). The combined aqueous layers were extracted with EtOAc (3×). The combined organic layers were dried ($Na_2SO_4$) and concentrated. The residue was purified by ISCO silica gel column to provide Stille coupling products (0.040 g, 75%). MS m/z 482.4 [M+H]⁺.

A solution of the Stille coupling product (0.040 g, 0.083 mmol) in MeOH (5.0 mL) was added a conc. HCl solution (0.50 mL). The resulting mixture was stirred for 1 h and concentrated under reduced pressure. After zoetrope with MeOH (3×), the residue was dissolved in MeOH (5.0 mL) and AcOH (0.50 mL) and was added Pd/C (0.009 g, 10 wt %). The reaction mixture was stirred at room temperature under hydrogen for 1 d, then filtered over Celite and washed with MeOH. The filtrate was concentrated and the residue was purified by reverse-phase HPLC to provide the desired product UNC3588A (0.025 g, 82% over 2 steps). ¹H NMR (400 MHz, $CD_3OD$) δ 8.62 (ddd, J=5.0, 1.6, 0.9 Hz, 1H), 8.28 (s, 1H), 7.96-7.82 (m, 2H), 7.39 (ddd, J=7.3, 5.0, 1.1 Hz, 1H), 3.91-3.79 (m, 1H), 3.71-3.53 (m, 3H), 3.49-3.38 (m, 1H), 1.92-1.78 (m, 1H), 1.76-1.65 (m, 3H), 1.62-1.34 (m, 14H). MS m/z 370.3 [M+H]⁺.

Table 5 describes compounds can be prepared following procedures described in Example 8 (General Procedure H), using appropriate reagents.

| Structure | Compound_ID | Mer IC₅₀ | Physical Data MS m/z (M + 1) or/and ¹H NMR |
|---|---|---|---|
| 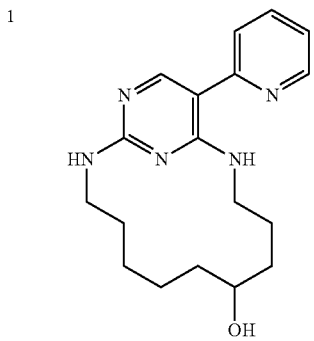 1 | | | |
| 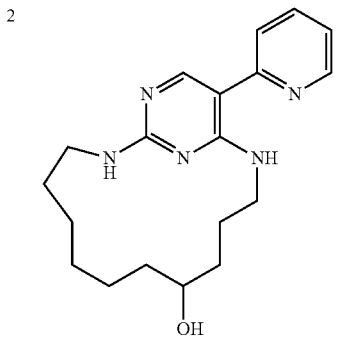 2 | | | |

-continued

Table 5 describes compounds can be prepared following procedures described in Example 8 (General Procedure H), using appropriate reagents.

| Structure | Compound_ID | Physical Data Mer IC$_{50}$ | MS m/z (M + 1) or/and $^1$H NMR |
|---|---|---|---|
| 3 | | | |
| 4 | | | |
| 5 | | | |
| 6 | | | |

Table 5 describes compounds can be prepared following procedures described in Example 8 (General Procedure H), using appropriate reagents.
| Structure | Compound_ID | Mer IC$_{50}$ | Physical Data MS m/z (M + 1) or/and $^1$H NMR |
|---|---|---|---|
| 7 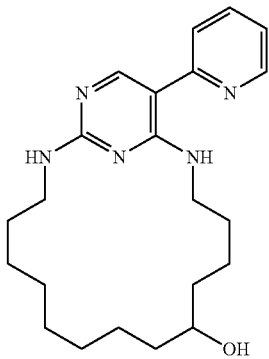 [SMILES: OC1CCCCCCCCNc2ncc(-c3ccccn3)c(n2)NCCCC1] | | | |
| 8 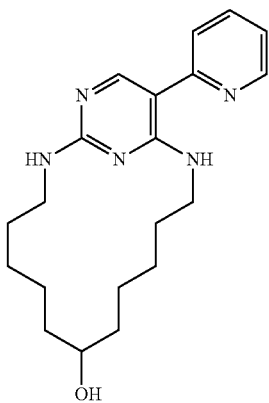 [SMILES: OC1CCCCCNc2ncc(-c3ccccn3)c(n2)NCCCCC1] | | | |
| 9 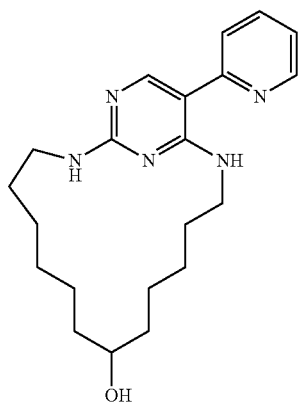 [SMILES: OC1CCCCCCNc2ncc(-c3ccccn3)c(n2)NCCCCC1] | | | |

Table 5 describes compounds can be prepared following procedures described in Example 8 (General Procedure H), using appropriate reagents.
| Structure | Compound_ID | Mer IC$_{50}$ | Physical Data MS m/z (M + 1) or/and $^1$H NMR |
|---|---|---|---|
| 10 (structure) | | | |
| 11 (structure) | | | |
Example 9
UNC329SA
General Procedure I
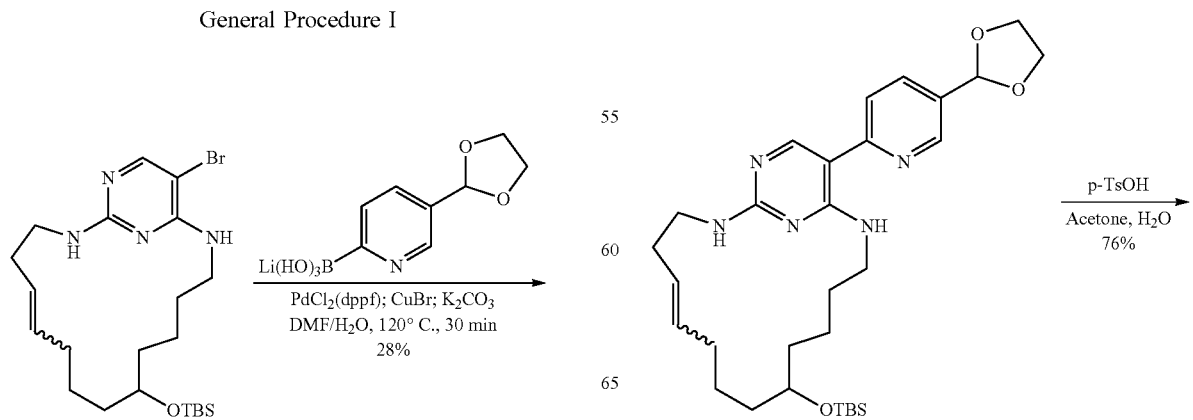

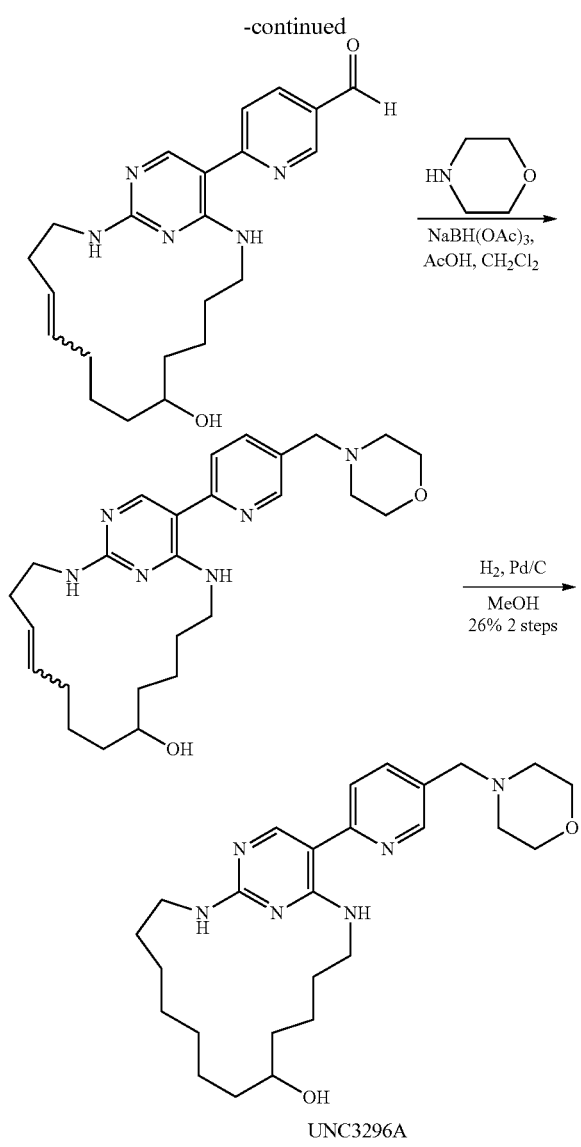

UNC3296A

A solution of the bromide intermediate (0.17 g, 0.34 mmol) in DMF (2.0 mL) was added Pd(dppf)Cl$_2$.CH$_2$Cl$_2$ (0.028 g, 0.034 mmol), CuBr (0.098 g, 0.68 mmol), K$_2$CO$_3$ (0.14 g, 1.02 mmol), (5-(1,3-dioxolan-2-yl)pyridin-2-yl)boronic acid lithium hydroxide (0.22 g, 1.02 mmol) and water (0.50 mL). The resulting mixture was heated at 120° C. for 30 min open to air. The mixture was filtered over Celite at room temperature. The solvents were removed under a reduced pressure and the residue was purified by ISCO silica gel column to provide the desired coupling product (0.053 g, 28%) contaminated with small amount impurities; MS m/z [M+H]$^+$.

A solution of the coupling product (0.053 g, 0.10 mmol) in acetone (10 mL) was added p-TsOH.H$_2$O (0.029 g, 0.15 mmol) and H$_2$O (0.80 mL). The reaction mixture was stirred at room temperature for 16 h, then quenched with a sat. aq solution of NaHCO$_3$ and extracted with EtOAc (3×). The combined organic layers were dried (Na$_2$SO$_4$) and concentrated. The resulting residue was purified by ISCO silica gel column to provide the desired aldehyde intermediate (0.031 g, 78%) contaminated with small amount impurities; MS m/z 554.4 [M+H]$^+$.

A solution of the aldehyde (0.031 g, 0.078 mmol) in CH$_2$Cl$_2$ (2.0 mL) was added morpholine (0.01 mL, 0.12 mmol) and 0.08 mL acetic acid. The resulting solution was stirred at room temperature for 2 h, then NaB(OAc)$_3$H (0.033 g, 0.16 mmol) was added. The reaction mixture was stirred at room temperature for 16 h, quenched by a sat. aq. solution of NaHCO$_3$ and extracted with EtOAc (3×). The combined organic layers were dried (Na$_2$SO$_4$) and concentrated. The residue was dissolved in MeOH (5.0 mL) and was added Pd/C (0.015 g, 5 wt % Pd/C). The reaction mixture was stirred under hydrogen atmosphere at room temperature for 16 h, then filtrated over Celite and washed with MeOH. The filtrate was concentrated and the residue was purified with reverse-phase HPLC to provide the desired product UNC3295A (0.0096 g, 26%). $^1$H NMR (400 MHz, CD$_3$OD) δ 8.73 (d, J=1.8 Hz, 1H), 8.40 (s, 1H), 8.06 (dd, J=8.5, 2.2 Hz, 1H), 7.96 (d, J=8.5 Hz, 1H), 4.40 (s, 2H), 3.98-3.80 (m, 5H), 3.70-3.51 (m, 3H), 3.49-3.38 (m, 1H), 3.29 (bs, 4H), 1.90-1.79 (m, 1H), 1.77-1.65 (m, 3H), 1.62-1.36 (m, 14H); MS m/z 469.4 [M+H]$^+$.

Table 6 describes compounds prepared following procedures described in Example 9 (General Procedure I), using appropriate reagents.

| | Structure | Compound_ID | Mer IC$_{50}$ | Physical Data MS m/z (M + 1) or/and $^1$H NMR |
|---|---|---|---|---|
| 1 | 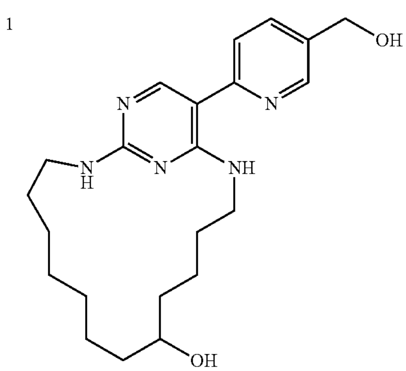 | UNC3296A | +++ | $^1$H NMR (400 MHz, CD$_3$OD) δ 8.49 (d, J = 1.3 Hz, 1H), 8.28 (s, 1H), 7.80-7.71 (m, 2H), 4.63 (s, 2H), 3.83-3.72 (m, 1H), 3.66-3.56 (m, 1H), 3.56-3.41 (m, 2H), 3.39-3.33 (m, 1H), 1.87-1.74 (m, 1H), 1.71-1.58 (m, 4H), 1.56-1.36 (m, 13H); MS m/z 400.3 [M + H]$^+$. |

Table 6 describes compounds prepared following procedures described in Example 9 (General Procedure I), using appropriate reagents.
| | Structure | Compound_ID | Mer IC$_{50}$ | Physical Data MS m/z (M + 1) or/and $^1$H NMR |
|---|---|---|---|---|
| 2 | 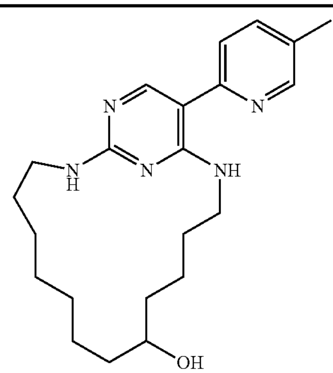 | UNC3334A | ++ | $^1$H NMR (400 MHz, CD$_3$OD) δ 8.46 (s, 1H), 8.22 (s, 1H), 7.74 (d, J = 1.6 Hz, 2H), 3.90-3.79 (m, 1H), 3.68-3.51 (m, 3H), 3.47-3.37 (m, 1H), 2.39 (s, 3H), 1.90-1.78 (m, 1H), 1.76-1.65 (m, 3H), 1.63-1.37 (m, 14H); MS m/z 384.3 [M + H]$^+$. |
Example 10
UNC3096A
General Procedure J
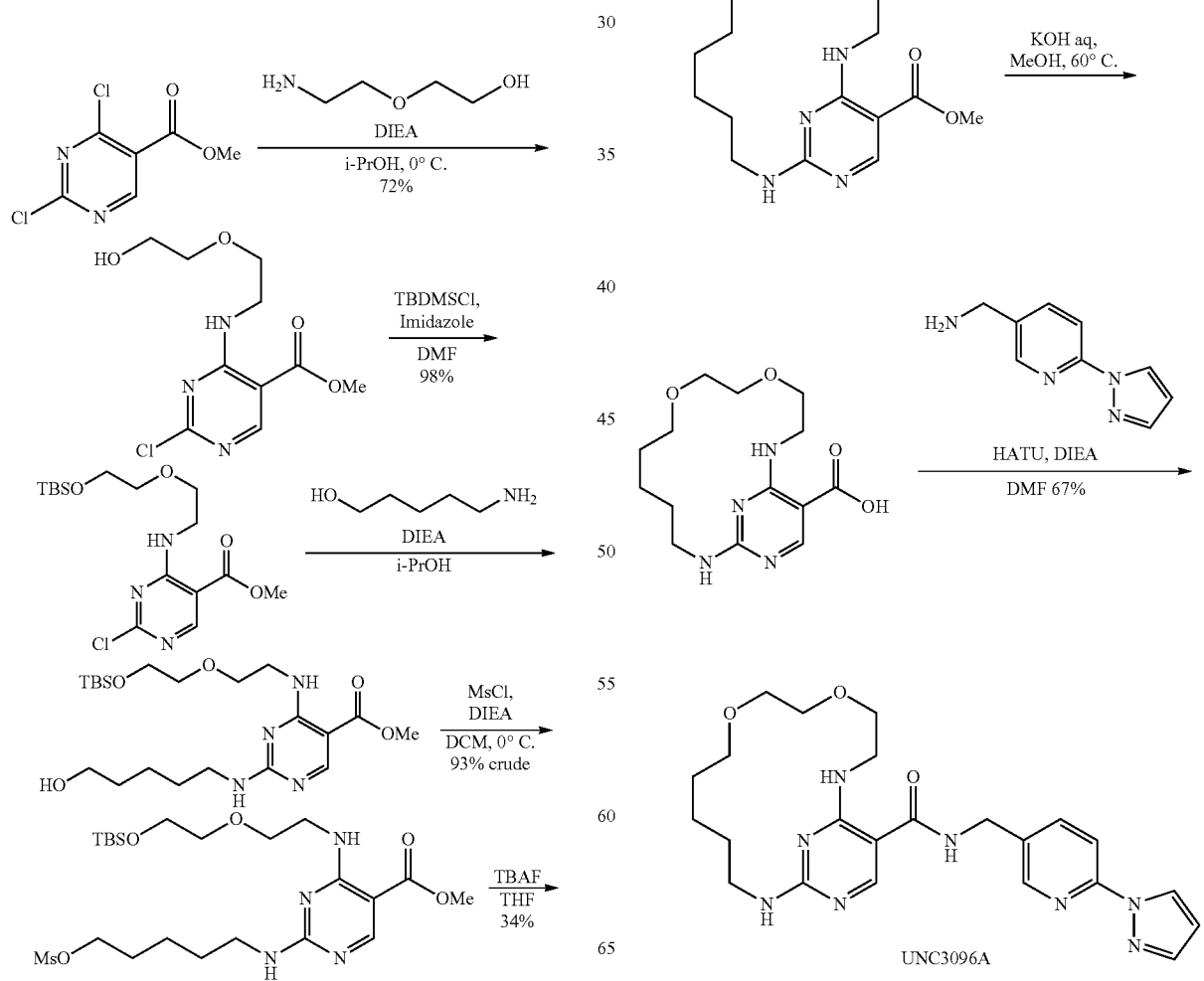
UNC3096A Methyl 2-chloro-4-{[2-(2-hydroxyethoxy)ethyl]amino}pyrimidine-5-carboxylate

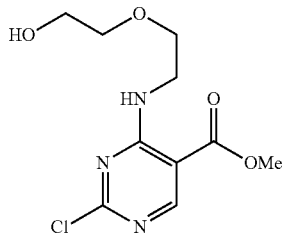 [SMILES: COC(=O)c1cnc(Cl)nc1NCCOCCO]

A solution of methyl 2,4-dichloropyrimidine-5-carboxylate (252 mg, 1.22 mmol) in i-PrOH (6 mL) was added 2-(2-aminoethoxyl)ethanol (122 μL, 1.22 mmol) and DIEA (319 μL, 1.83 mmol) at 0° C. After 1.5 h the volatiles were removed under a reduced pressure and the residue was purified by ISCO silica gel column to provide the title compound (243 mg, 72%) as a white solid. $^1$H NMR (400 MHz, CDCl$_3$) δ 8.67 (s, 1H), 3.90 (s, 3H), 3.82-3.74 (m, 4H), 3.70 (t, J=5.2 Hz, 2H), 3.67-3.61 (m, 2H), 2.17 (t, J=6.3 Hz, 1H).

Methyl 2-chloro-4-(8,8,9,9-tetramethyl-4,7-dioxa-1-aza-8-siladecan-1-yl)pyrimidine-5-carboxylate

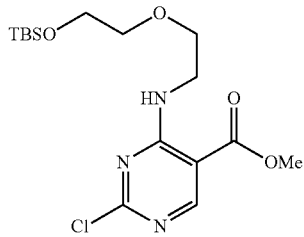 [SMILES: COC(=O)c1cnc(Cl)nc1NCCOCCO[Si](C)(C)C(C)(C)C]

A solution of methyl 2-chloro-4-{[2-(2-hydroxyethoxyl)ethyl]amino}pyrimidine-5-carboxylate (99 mg, 0.36 mmol) in DMF (720 μL) was added imidazole (49 mg, 0.72 mmol) followed by TBDMSCl (60 mg, 0.396 mmol). The reaction mixture was stirred at room temperature for 1 h, diluted with H$_2$O (2 mL) and extracted with CH$_2$Cl$_2$ (3×2 mL). The combined organic layers were washed with brine (2×2 mL), dried (Na$_2$SO$_4$) and concentrated. The residue was purified by ISCO silica gel column to provide the title compound (137 mg, 98%) as a colorless oil.

Methyl 2-[(5-hydroxypentyl)amino]-4-(8,8,9,9-tetramethyl-4,7-dioxa-1-aza-8-siladecan-1-yl)pyrimidine-5-carboxylate

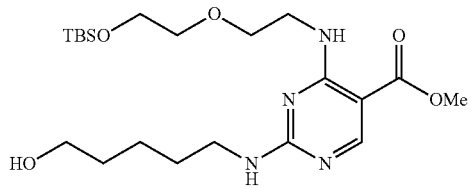 [SMILES: COC(=O)c1cnc(NCCCCCO)nc1NCCOCCO[Si](C)(C)C(C)(C)C]

A solution of methyl 2-chloro-4-(8,8,9,9-tetramethyl-4,7-dioxa-1-aza-8-siladecan-1-yl)pyrimidine-5-carboxylate (133 mg, 0.341 mmol) in i-PrOH (3.4 mL) was added 5-aminopentan-1-ol (185 μL, 1.7 mmol) and DIEA (89 μL, 0.511 mmol). The reaction mixture was stirred at room temperature overnight. The solvents were removed under a reduced pressure and the residue was purified by ISCO silica gel column to provide the title compound (156 mg, >99%) as a colorless oil.

Methyl 5,8-dioxa-2,14,16,19-tetraazabicyclo[13.3.1]nonadeca-1(18),15(19),16-triene-18-carboxylate

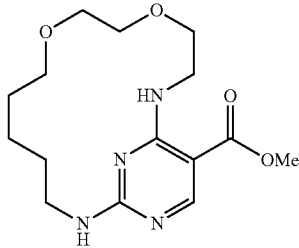 [SMILES: COC(=O)c1cnc2nc1NCCOCCOCCCCCN2]

A solution of methyl 2-[(5-hydroxypentyl)amino]-4-(8,8,9,9-tetramethyl-4,7-dioxa-1-aza-8-siladecan-1-yl)pyrimidine-5-carboxylate (150 mg, 0.328 mmol) in CH$_2$Cl$_2$ (3.3 mL) was added DIEA (143 μL, 0.82 mmol) then methane sulfonylchloride (28 μL, 0.361) at 0° C. The reaction mixture was stirred for 30 min and diluted with H$_2$O (12 mL). The organic layer was washed with brine (10 mL) and dried to provide the crude mesylate that was used for the next step without further purification. The mesylate was dissolved in THF (7.3 mL) and TBAF (1M in THF, 585 μL, 0.585 mmol) was added. The reaction mixture was stirred at room temperature overnight. The solvents were removed under a reduced pressure and the residue was purified by ISCO silica gel column to provide the title compound (32 mg, 34%) as a white solid. $^1$H NMR (400 MHz, CDCl$_3$) δ 8.57 (s, 1H), 3.86-3.79 (m, 7H), 3.79-3.73 (m, 2H), 3.72-3.66 (m, 5H), 3.64-3.59 (m, 2H), 2.32 (dd, J=9.3, 3.6 Hz, 1H), 1.72-1.64 (m, 2H), 1.59 (dd, J=10.8, 5.7 Hz, 4H).

5,8-Dioxa-2,14,16,19-tetraazabicyclo[13.3.1]nonadeca-1(18),15(19),16-triene-18-carboxylic acid

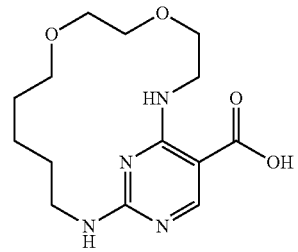 [SMILES: O=C(O)c1cnc2nc1NCCOCCOCCCCCN2]

A solution of methyl 5,8-dioxa-2,14,16,19-tetraazabicyclo[13.3.1]nonadeca-1(18),15(19),16-triene-18-carboxylate (32 mg, 0.099 mmol) in MeOH (1.4 mL) was added a 4.0 M KOH solution (250 μL). The reaction mixture was heated at 60° C. overnight. The reaction was cooled and the MeOH was removed under a reduced pressure. The mixture was acidified with a 4.0 N HCl solution to pH ~2. The aqueous layer was extracted with 3:1 $CH_2Cl_2$/i-PrOH (3×5 mL). The combined organic layers were dried ($Na_2SO_4$) and concentrated to afford the title compound (35 mg, >99%) as a white solid.

N-{[6-(1H-Pyrazol-1-yl)pyridin-3-yl]methyl}-5,8-dioxa-2,14,16,19-tetraazabicyclo[13.3.1]nonadeca-(18),15(19), 16-triene-18-carboxamide (UNC3096A)

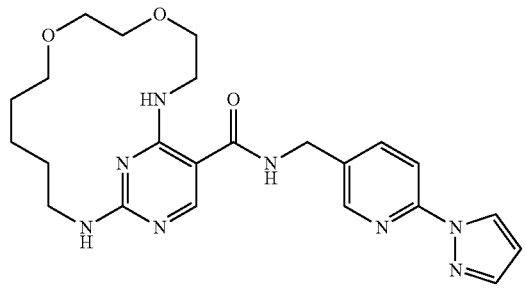 [SMILES: O=C(NCc1ccc(-n2cccn2)nc1)c1cnc2nc1NCCOCCOCCCCCN2]

A solution of 5,8-dioxa-2,14,16,19-tetraazabicyclo [13.3.1]nonadeca-1(18), 15(19),16-triene-18-carboxylic acid (30 mg, 0.099 mmol) in DMF (1.0 mL) was added [6-(1H-pyrazol-1-yl)pyridin-3-yl]methanamine (17 mg, 0.099 mmol) and DIEA (34 μL, 0.197 mmol) followed by HATU (41 mg, 0.108 mmol). The reaction mixture was stirred at room temperature overnight, quenched with a 1.0 M NaOH solution (2.0 mL) and extracted with $CH_2Cl_2$ (2×2 mL). The combined organic layers were dried ($Na_2SO_4$) and concentrated. The residue was purified by HPLC to afford the title compound (37 mg, 67%) as a light yellow solid. $^1$H NMR (400 MHz, $CD_3OD$) δ 8.62 (dd, J=2.7, 0.4 Hz, 1H), 8.50 (d, J=1.9 Hz, 1H), 8.32 (s, 1H), 8.15 (dd, J=8.6, 2.3 Hz, 1H), 8.03 (d, J=8.5 Hz, 1H), 7.85 (d, J=1.3 Hz, 1H), 6.61 (dd, J=2.7, 1.7 Hz, 1H), 4.59 (s, 2H), 3.85-3.63 (m, 10H), 3.63-3.55 (m, 21H), 1.81-1.65 (m, 6H). MS m/z 467.3 [M+H]$^+$.

Example 11

UNC3040A

General Procedure K

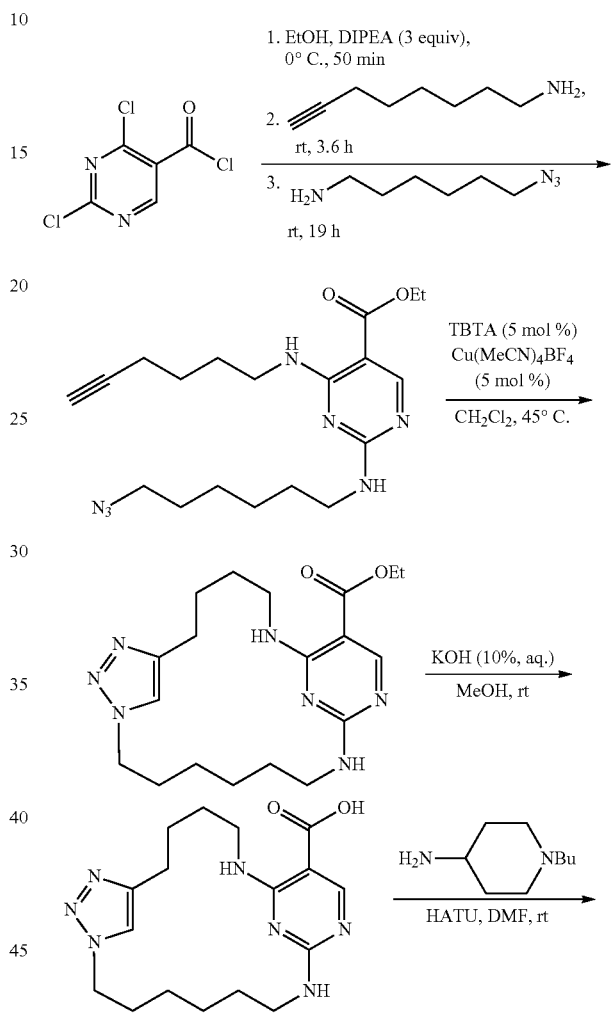

Table 7 describes compounds prepared following procedures described in Example 10 (General Procedure J), using appropriate reagents.

| | Structure | Compound_ID | Mer $IC_{50}$ | Physical Data MS m/z (M + 1) or/and $^1$H NMR |
|---|---|---|---|---|
| 1 | (structure shown) | UNC2887A | ++ | $^1$H NMR (400 MHz, $CD_3OD$) δ 8.59 (d, J = 2.6 Hz, 1H), 8.46 (d, J = 1.9 Hz, 1H), 8.26 (s, 1H), 8.03 (dd, J = 8.5, 2.3 Hz, 1H), 7.95 (d, J = 8.5 Hz, 1H), 7.79 (d, J = 1.4 Hz, 1H), 6.57 (dd, J = 2.6, 1.8 Hz, 1H), 4.57 (s, 2H), 3.85-3.71 (m, 6H), 3.69-3.64 (m, 2H), 3.64-3.59 (m, 4H), 3.59-3.52 (m, 4H). MS m/z 469.3 [M + H]$^+$. |

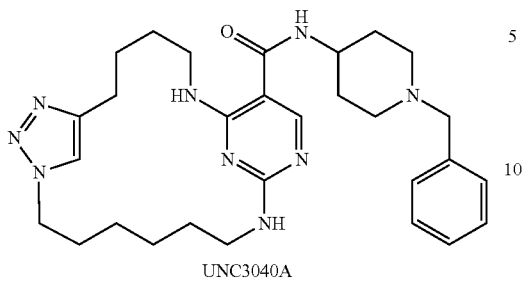

UNC3040A

Ethyl 2,8,9,10,17,19,22-heptaazatricyclo[16.3.1.1⁷,¹⁰]tricosa-1(21),7(23),8.18(22),19-pentaene-21-carboxylate

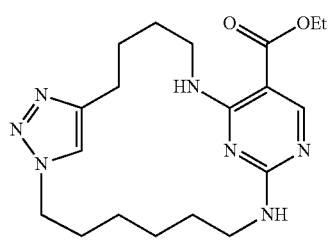 [SMILES: CCOC(=O)c1cnc2nc1NCCCCc1cn(nn1)CCCCCCN2]

A solution of 2,4-dichloropyrimidine-5-carbonyl chloride (1.00 g, 4.76 mmol) in ethanol (6.0 mL) was added DIPEA (2.5 mL, 14.4 mmol) slowly at 0° C. under nitrogen. After 30 min, hex-5-yn-1-amine (0.476 g, 4.91 mmol) was added in one portion. The reaction mixture was stirred at room temperature for 3.5 h, then was added dropwise to a solution of 6-azidohexan-1-amine (0.801 g, 5.64 mmol) in ethanol (4.0 mL) at 50° C. After the reaction was complete (monitored by LCMS), the mixture was diluted with water (10 mL) and concentrated under a reduced pressure and filtered. The yellow solid was washed with water and dried under vacuum to be used in the next step without further purification (0.723 g, 39% over 3 steps).

A solution of the yellow solid (0.130 g, 0.336 mmol) in dry $CH_2Cl_2$ (25 mL) was added TBTA (1.6 mL, 5 mg/mL in $CH_2C2$, 8.0 mg, 0.016 mmol) and $Cu(MeCN)_4BF_4$ (5.2 mg, 0.016 mmol). The reaction mixture was stirred under nitrogen at 45° C. for 24 h, then cooled to room temperature and concentrate. The residue was purified by silica gel column to provide the title compound (0.104 g, 80%). ¹H NMR (400 MHz, $CD_3OD$) δ 8.34 (s, 2H), 7.58 (s, 1H), 4.36 (s, 2H), 4.22 (q, J=7.1 Hz, 2H), 3.34 (s, 2H), 3.19 (s, 2H), 2.82-2.66 (m, 2H), 1.84 (s, 2H), 1.67 (s, 2H), 1.62-1.44 (m, 4H), 1.40-1.02 (m, 7H).

2,8,9,10,17,19,22-Heptaazatricyclo[16.3.1.1⁷,¹⁰]tricosa-1(21),7(23),8,18(22),19-pentaene-21-carboxylic acid

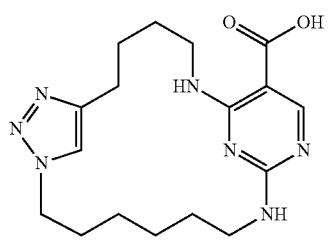 [SMILES: O=C(O)c1cnc2nc1NCCCCc1cn(nn1)CCCCCCN2]

A solution of ethyl 2,8,9,10,17,19,22-heptaazatricyclo[16.3.1.1⁷,¹⁰]tricosa-1(21),7(23),8,18(22),19-pentaene-21-carboxylate (31 mg, 0.081 mmol) in MeOH (2.0 mL) was added an aq. KOH solution (10%, 0.50 mL). The reaction was stirred at 60° C. for 12 h. Then the reaction mixture was cooled to room temperature and adjusted to pH=3 by the addition of a HCl solution. The resulting solution was extracted by a mixture of i-PrOH/$CH_2Cl_2$ (1:3, 10 mL×3). The combined organic layers were washed with water and brine and concentrated under vacuum to afford the desired product (0.029 g, quant.) as a white solid. ¹H NMR (400 MHz, $CD_3OD$) δ 8.41-8.22 (m, 1H), 5.65 (s, 2H), 4.63-4.46 (m, 1H), 3.55-3.43 (m, 1H), 3.39-3.33 (m, 1H), 3.02 (t, J=6.9 Hz, 3H), 2.97-2.83 (m, 1H), 2.58-2.29 (m, 3H), 2.03-1.89 (m, 1H), 1.85-1.71 (m, 1H), 1.71-1.50 (m, 2H), 1.49-0.97 (m, 3H).

N-(1-benzylpiperidin-4-yl)-2,8,9,10,17,19,22-heptaazatricyclo[16.3.1.1⁷,¹⁰]tricosa-1(21),7(23),8.18(22),19-pentaene-21-carboxamid (UNC3040A)

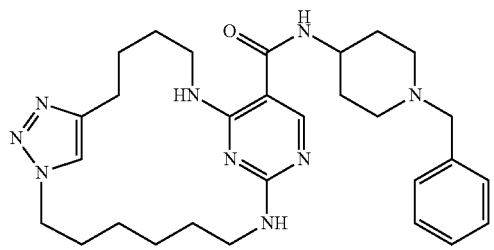 [SMILES: O=C(NC1CCN(Cc2ccccc2)CC1)c1cnc2nc1NCCCCc1cn(nn1)CCCCCCN2]

A solution of 2,8,9,10,17,19,22-Heptaazatricyclo[16.3.1.1⁷,¹⁰]tricosa-1(21),7(23),8,18(22),19-pentaene-21-carboxylic acid (30 mg, 0.084 mmol) in DMF (2.0 mL) was added 1-benzylpiperidin-4-amine (19.8 mg, 0.10 mmol) followed by HATU (38 mg, 0.10 mmol). The reaction mixture was stirred at room temperature overnight, quenched with a 1.0 M NaOH solution (2.0 mL) and extracted with $CH_2Cl_2$ (2×2 mL). The combined organic layers were dried ($Na_2SO_4$) and concentrated. The residue was purified by HPLC to afford the title compound UNC3040A (6.0 mg, 13%) as a light yellow solid. ¹H NMR (400 MHz, $CD_3OD$) δ 8.24 (s, 1H), 8.08-7.93 (m, 2H), 7.64-7.46 (m, 4H), 4.54-4.46 (m, 2H), 4.33 (s, 1H), 3.59-3.40 (m, 4H), 3.22-3.05 (m, 2H), 3.02-2.93 (m, 3H), 2.91-2.77 (m, 3H), 2.37-2.26 (m, 1H), 2.25-2.13 (m, 2H), 1.98-1.86 (m, 3H), 1.79-1.70 (m, 2H), 1.66-1.50 (m, 4H), 1.30-1.10 (m, 4H); MS (ESI): 554.5 [M+Na]⁺.

The foregoing is illustrative of the present invention, and is not to be construed as limiting thereof. The invention is defined by the following claims, with equivalents of the claims to be included therein.
That which is claimed is:
1. A compound having the following structure:
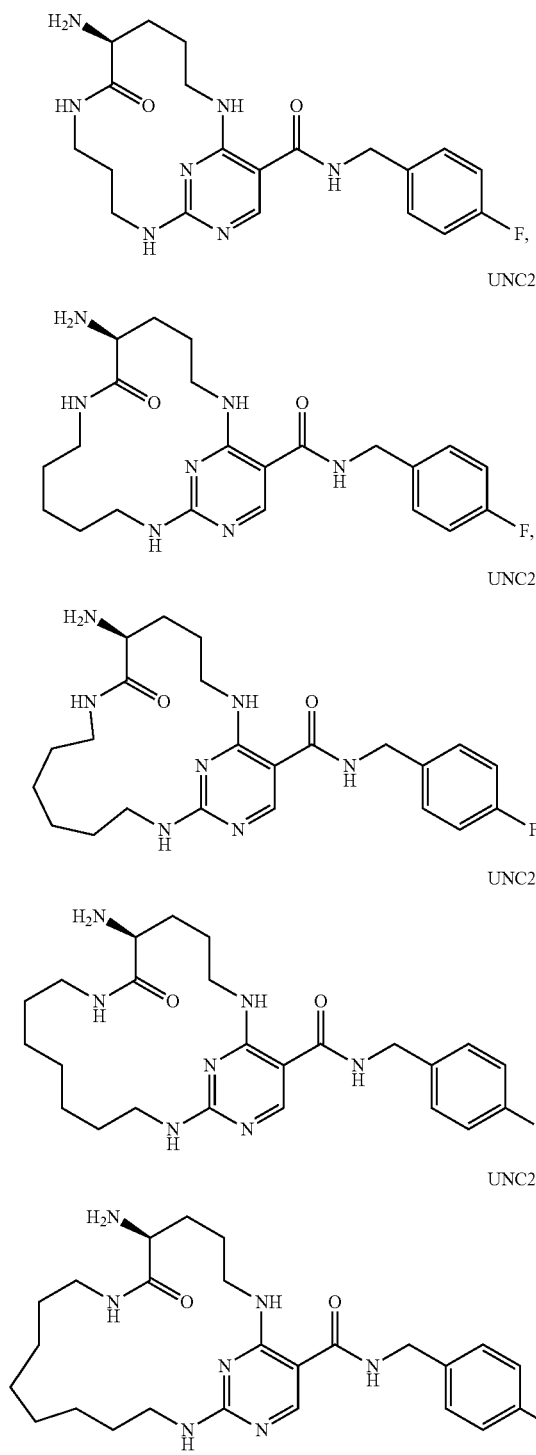
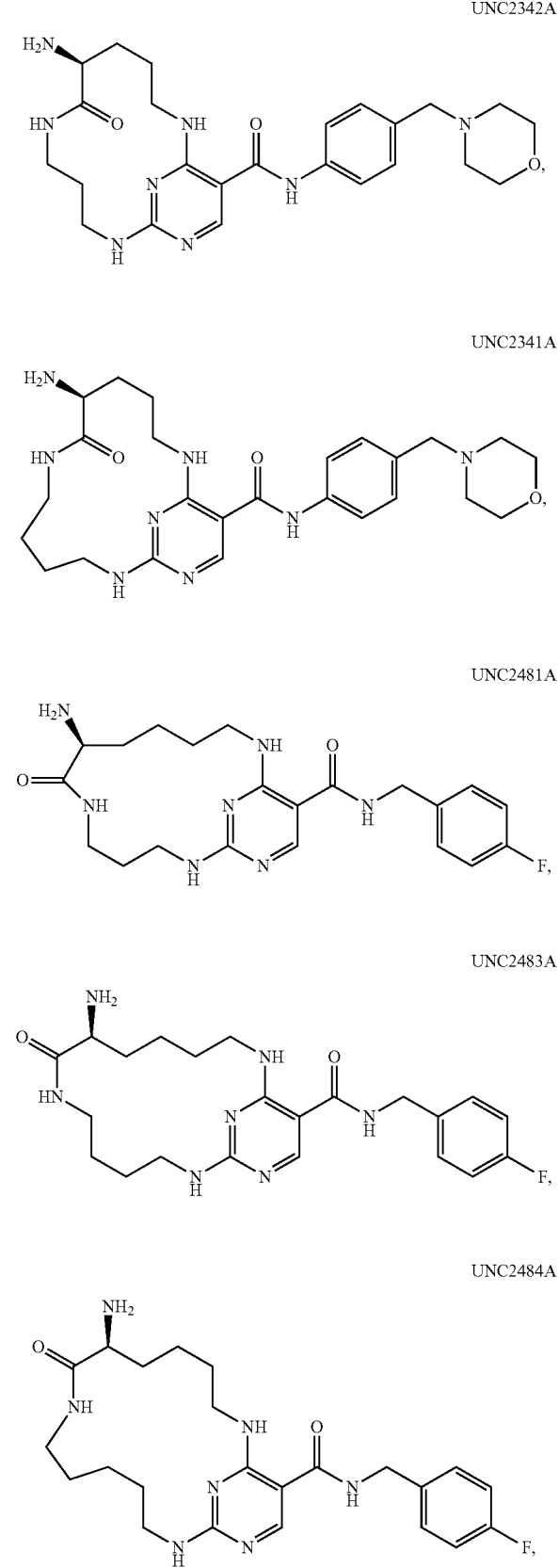

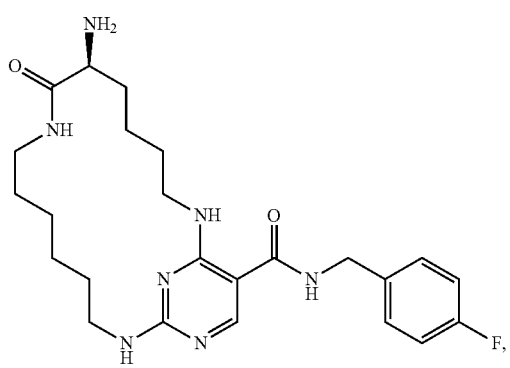
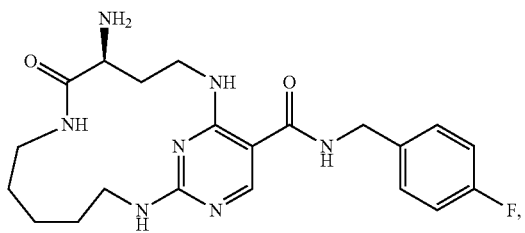

UNC2343A
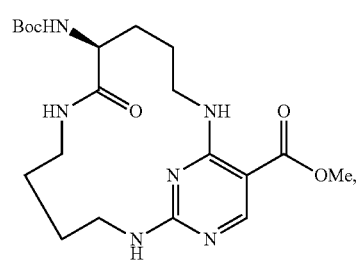
UNC2340A
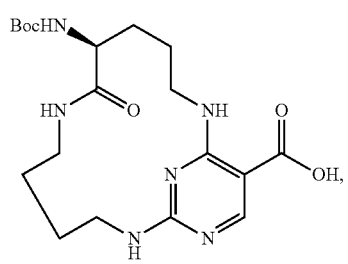
UNC2324A
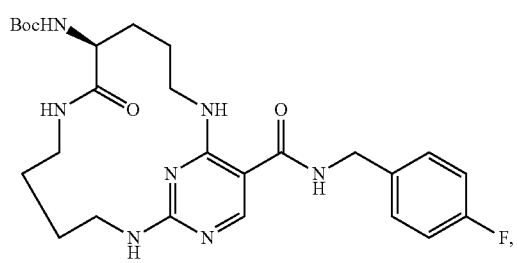
UNC2589A
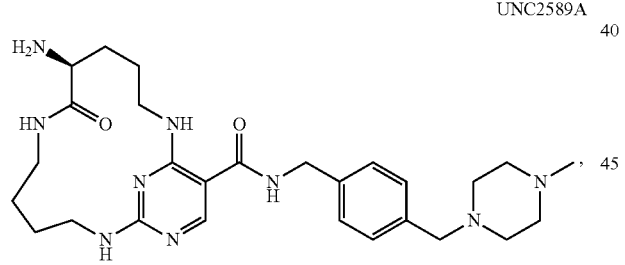
UNC2615A
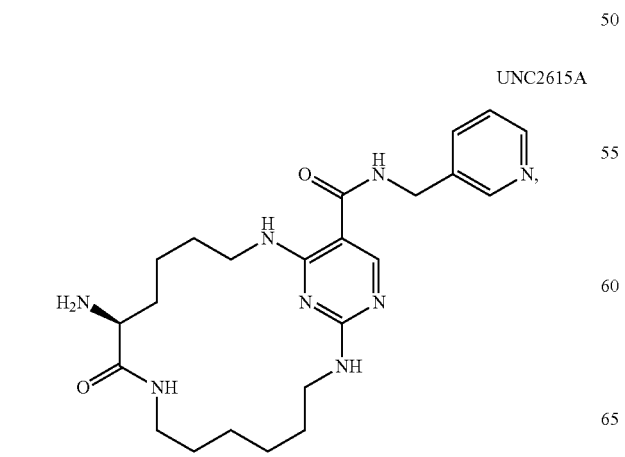
UNC2616A
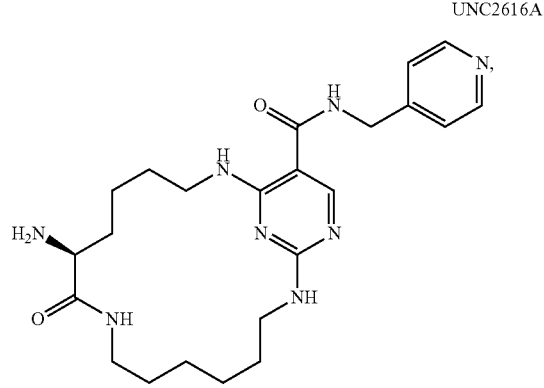
UNC2625A
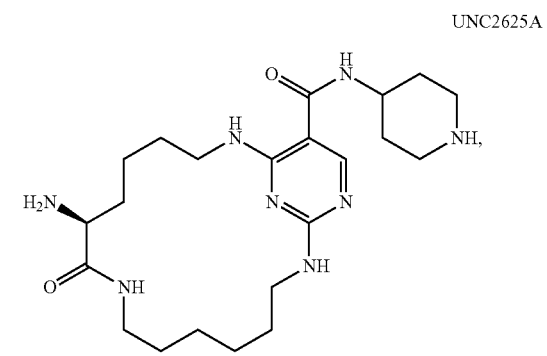
UNC2702A
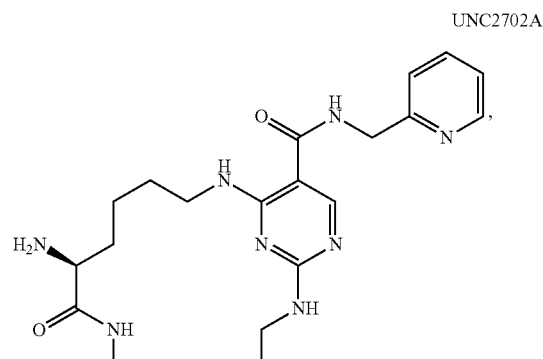
UNC2626A
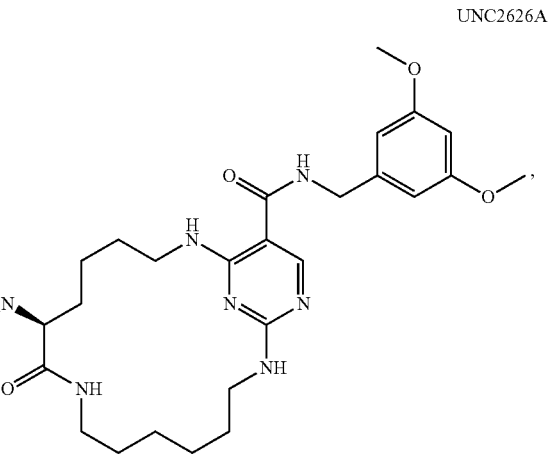

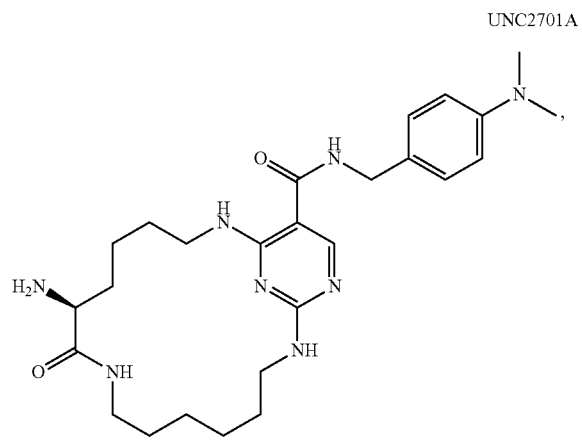
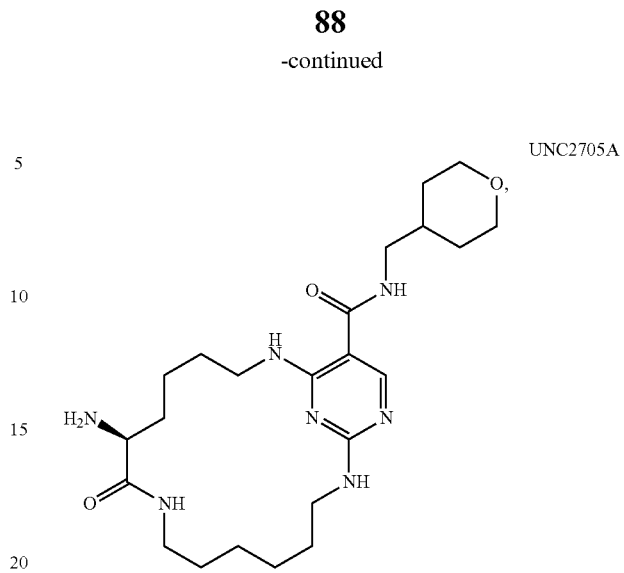
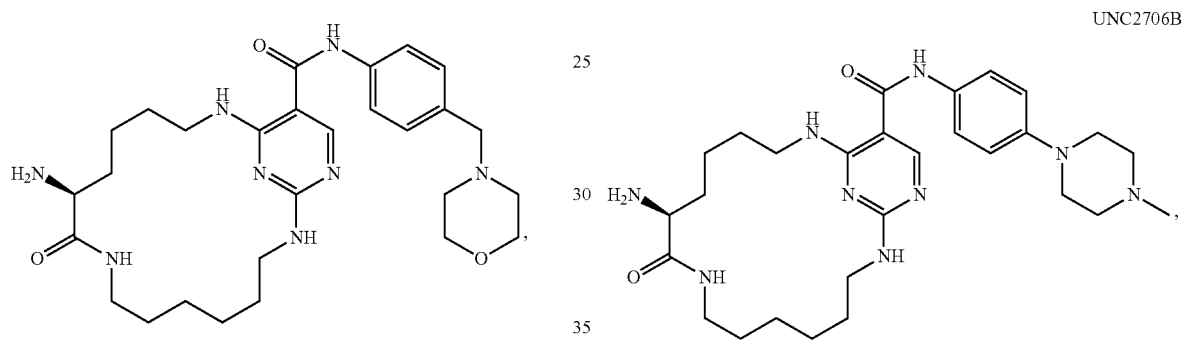
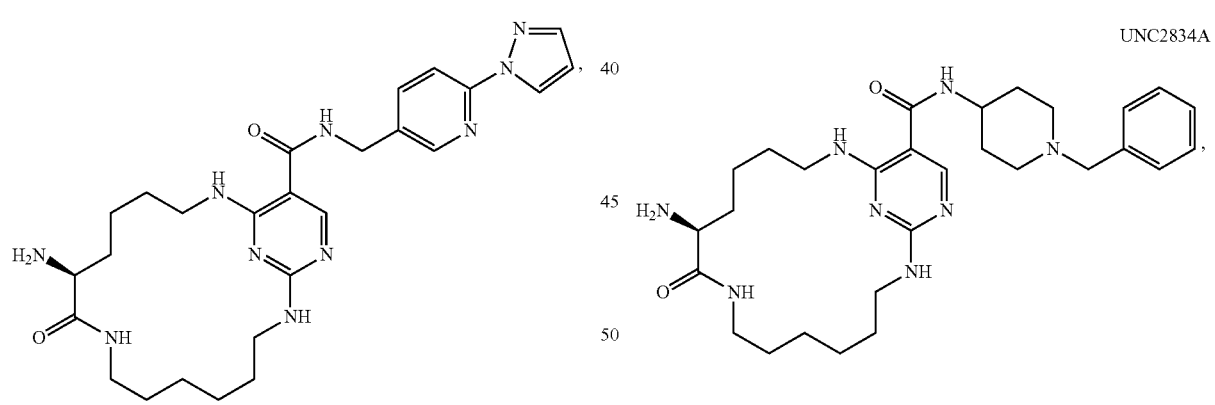
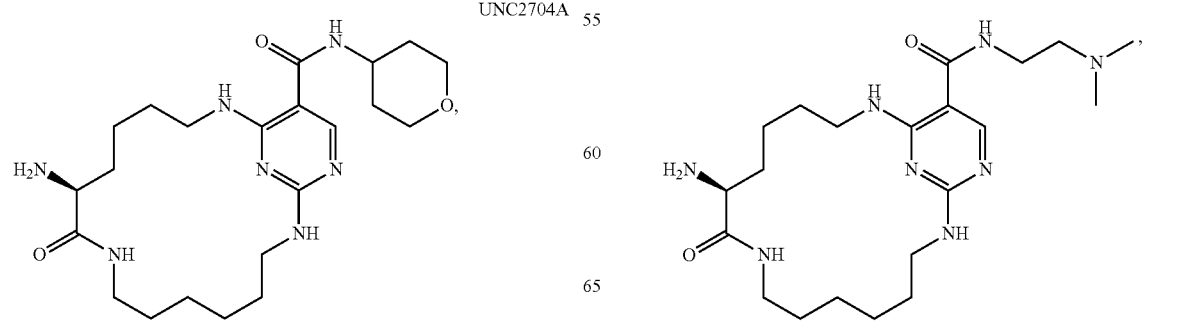

| 89 | 90 |
|---|---|
| -continued | -continued |
| UNC2836A 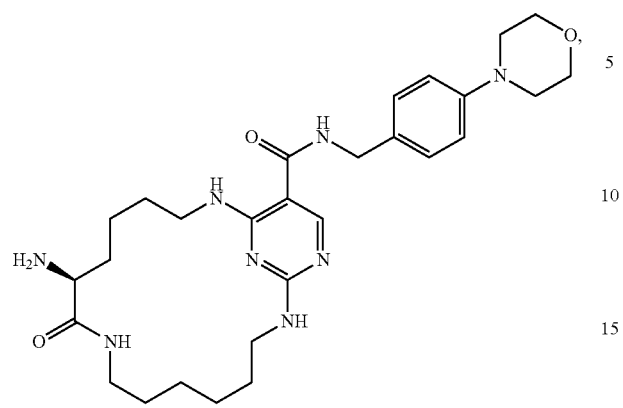 | UNC2968A 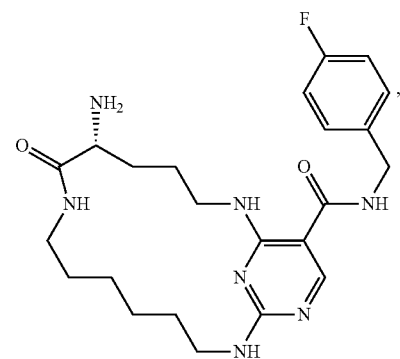 |
| UNC2837A 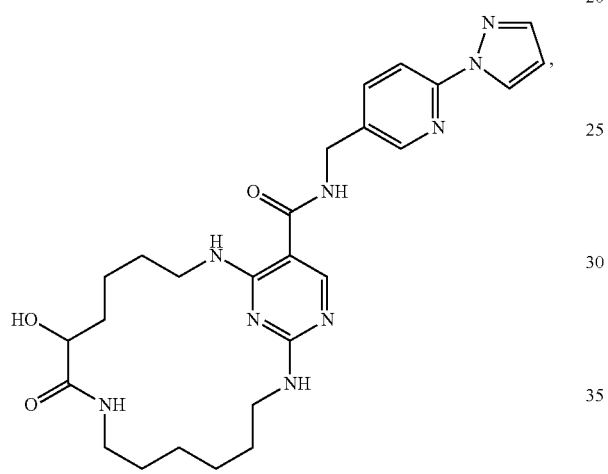 | UNC3038A 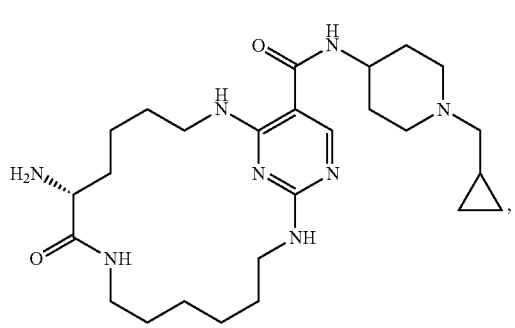 |
| | UNC2914A 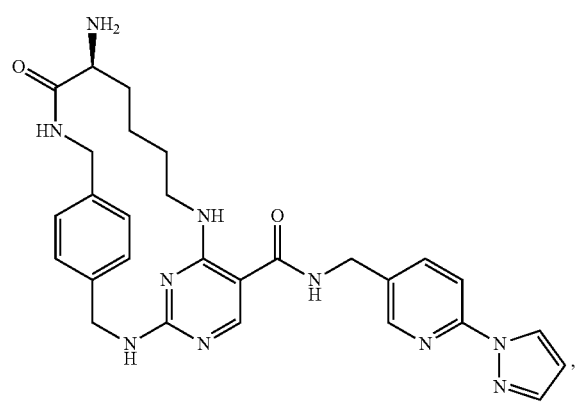 |
| UNC2910A 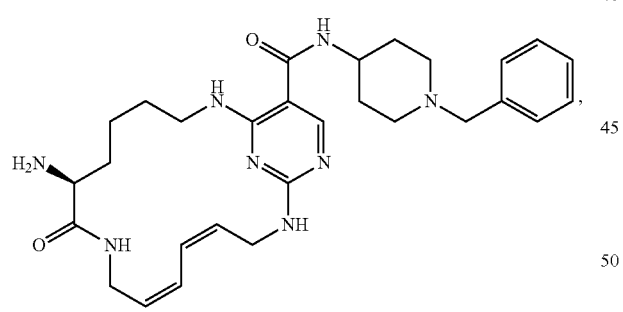 | |
| UNC2967A 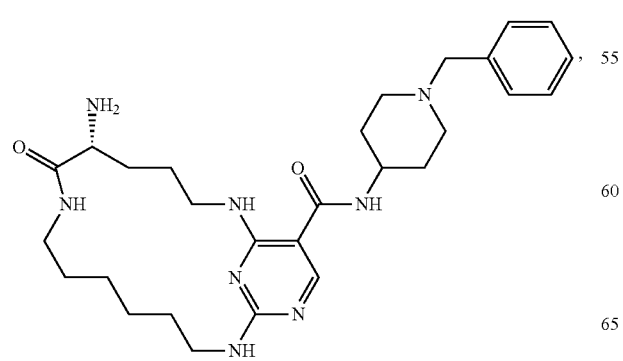 | UNC2916A 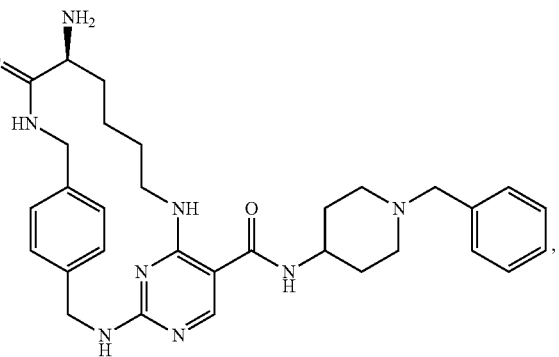 |

UNC3263A
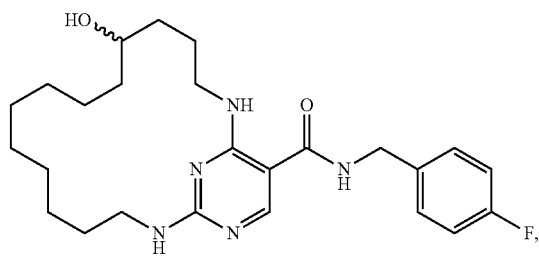
UNC3388A
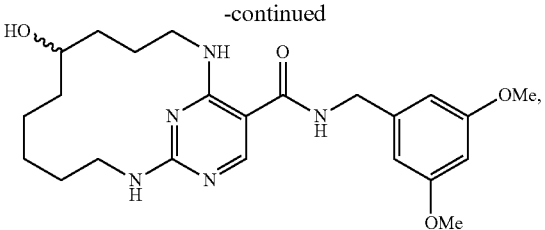
UNC3429A
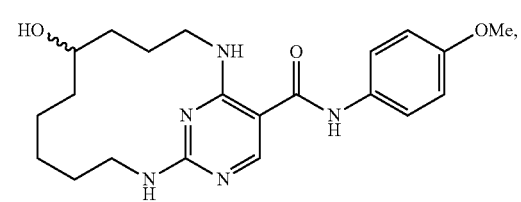
UNC3431A
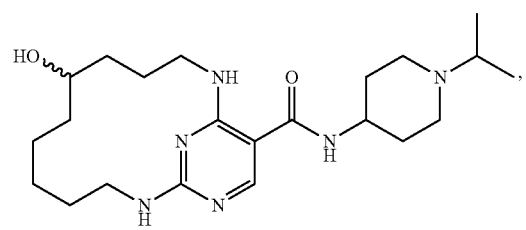
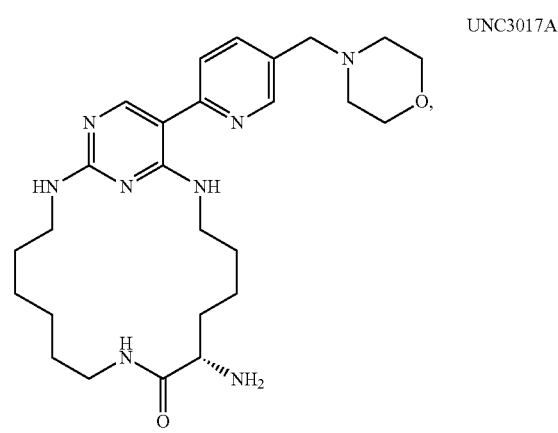
UNC3017A
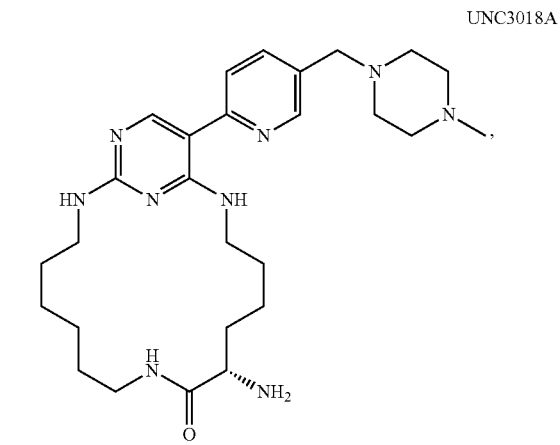
UNC3018A UNC3019A
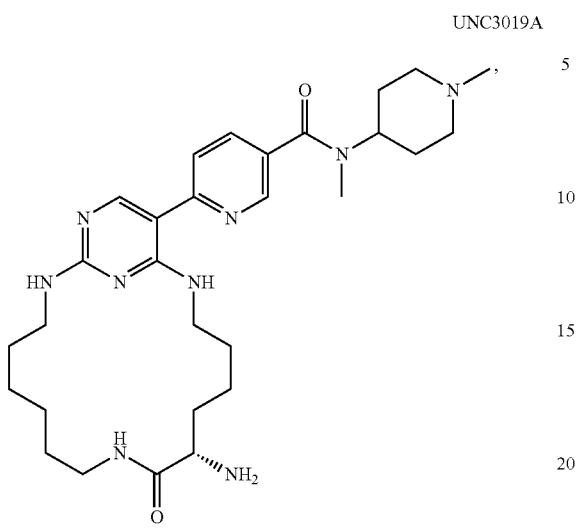
UNC3588A
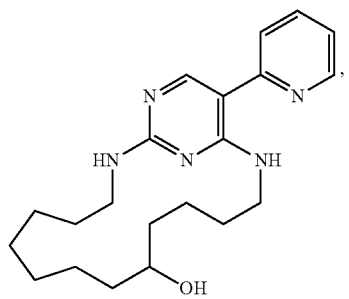
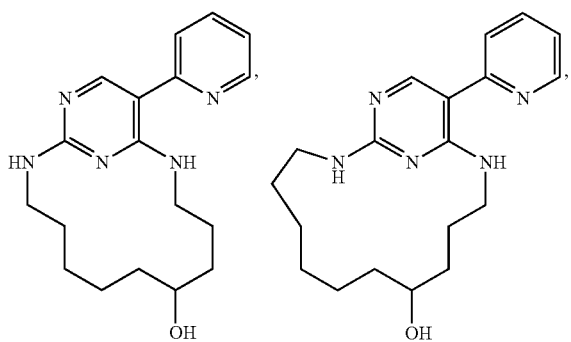
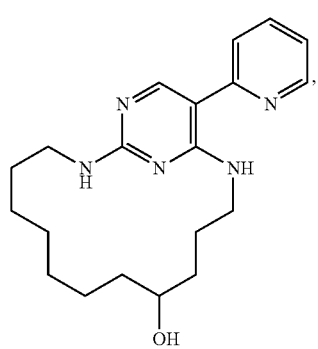
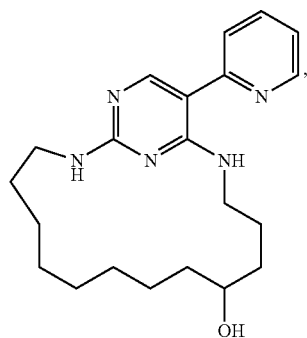
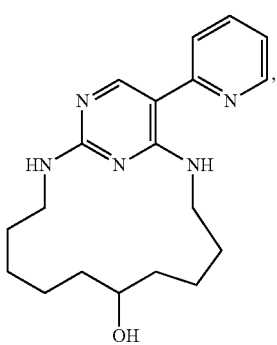
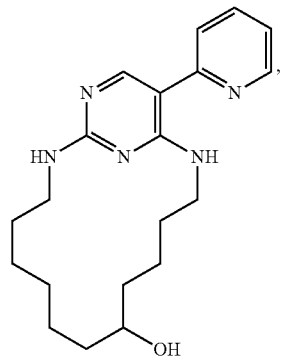 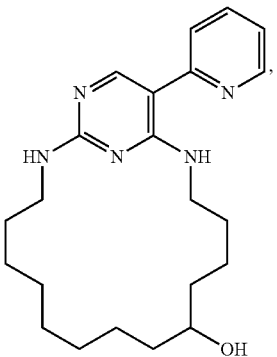
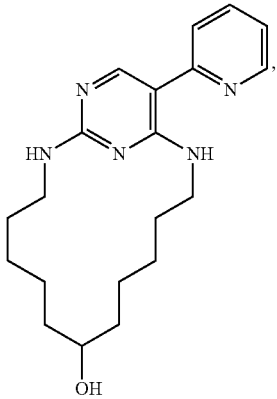

95
-continued
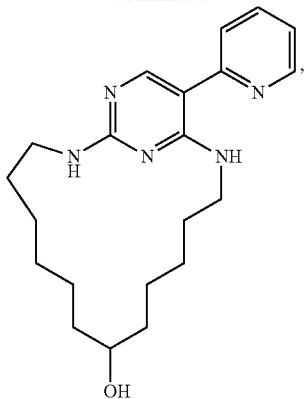
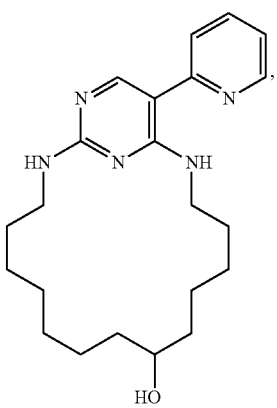
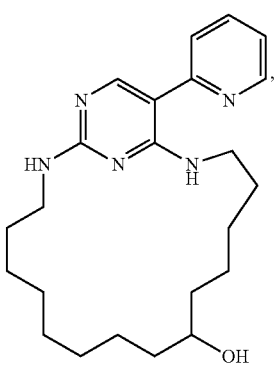
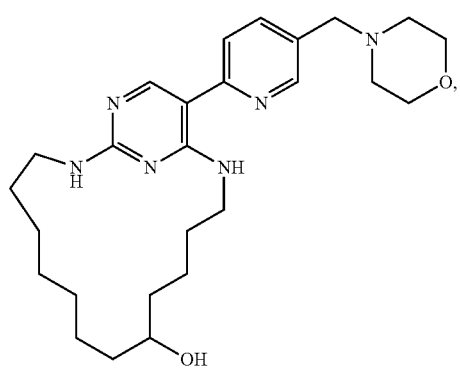
UNC3295A
96
-continued
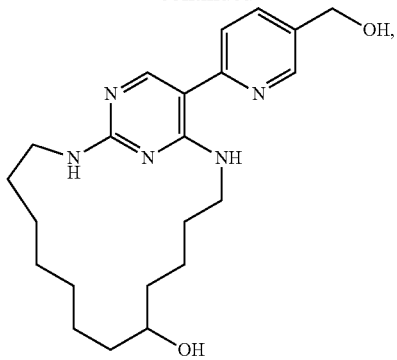
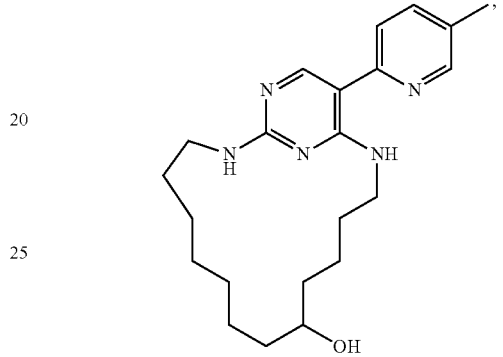
UNC3096A
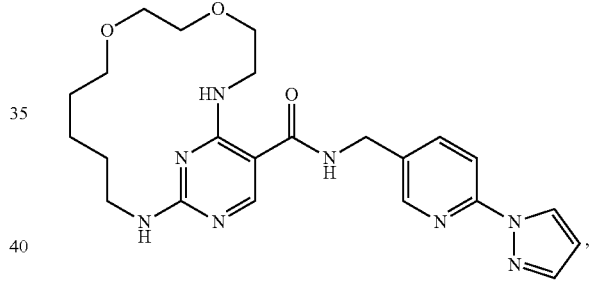
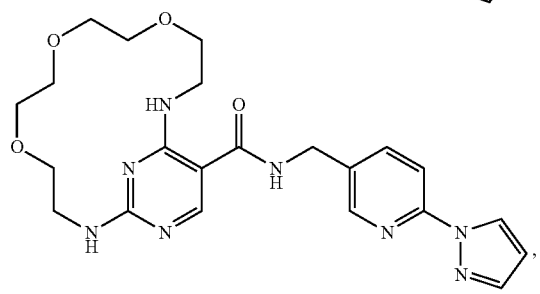
or
UNC3040A
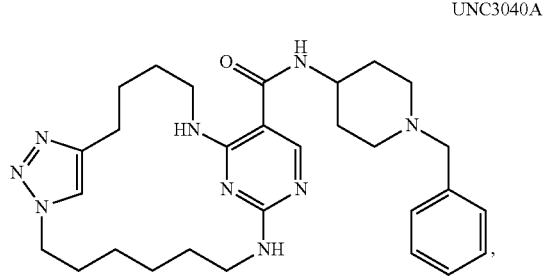
and pharmaceutically acceptable salts thereof.

2. A composition comprising the compound of claim 1 in a pharmaceutically acceptable carrier.

3. A method of improving the condition of a cancer in a subject in need thereof, comprising administering to said subject the compound of claim 1 in an amount effective to improve the condition of said cancer, wherein said cancer is selected from the group consisting of myeloid leukemia, lymphoblastic leukemia, melanoma, breast, and colon cancer.

* * * * *

UNITED STATES PATENT AND TRADEMARK OFFICE
CERTIFICATE OF CORRECTION

PATENT NO. : 9,771,330 B2
APPLICATION NO. : 14/647733
DATED : May 23, 2017
INVENTOR(S) : Wang et al.

Page 1 of 1

It is certified that error appears in the above-identified patent and that said Letters Patent is hereby corrected as shown below:

In the Specification

Column 1, Lines 21-24:
The paragraph that reads:
"This invention was made with government support under Grant No. HHSN261200800001E awarded by the National Institutes of Health. The government has certain rights in the invention."

Should read:
-- This invention was made with government support under Grant Number HHSN261200800001E awarded by the National Institutes of Health. The government has certain rights in the invention. --

Signed and Sealed this
Seventeenth Day of April, 2018

Andrei Iancu
*Director of the United States Patent and Trademark Office*